(12) United States Patent
Tasler et al.

(10) Patent No.: US 8,207,174 B2
(45) Date of Patent: Jun. 26, 2012

(54) ARYLOXYPROPANOLAMINES, METHODS OF PREPARATION THEROF AND USE OF ARYLOXYPROPANOLAMINES AS MEDICAMENTS

(75) Inventors: Stefan Tasler, Seefeld (DE); Daniel Vitt, Germering (DE); Kristina Wolf, Kottgeisering (DE); Andrea Aschenbrenner, Munich (DE); Peter Ney, Grevenbroich (DE)

(73) Assignee: 4SC AG, Martinsried (DE)

( * ) Notice: Subject to any disclaimer, the term of this patent is extended or adjusted under 35 U.S.C. 154(b) by 914 days.

(21) Appl. No.: 12/017,724

(22) Filed: Jan. 22, 2008

(65) Prior Publication Data
US 2008/0249114 A1  Oct. 9, 2008

Related U.S. Application Data

(60) Provisional application No. 60/886,020, filed on Jan. 22, 2007.

(30) Foreign Application Priority Data

Jan. 22, 2007 (EP) .................................... 07001347

(51) Int. Cl.
C07D 401/04 (2006.01)
C07D 495/04 (2006.01)
A61K 31/4545 (2006.01)

(52) U.S. Cl. ..................... 514/260.1; 514/275; 544/278; 544/332

(58) Field of Classification Search .................. 544/278, 544/332; 514/260.1, 275
See application file for complete search history.

(56) References Cited

U.S. PATENT DOCUMENTS 5,451,677 A   9/1995  Fisher et al.
2003/0040530 A1  2/2003  Cecchi

FOREIGN PATENT DOCUMENTS

WO   WO 01/07025 A     2/2001
WO   WO 01/44227 A     6/2001
WO   WO 2004/014850  *  2/2004

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, pp. 1-7, Aug. 2002.*
Fenning, Dysmenorrhoea, Current Obstetrics & Gynaecology (2005) 15, pp. 394-401.*
Sawa, M., et al., Recent Developments in the Design of Orally Bioavailable beta 3 Adrenergic Receptor Agonists, Current Medicinal Chemistry, vol. 13, 2006, pp. 25-37—XP0024844049.
Hu, B., et al., "2,4-Thiazolidinediones as Potent and Selective Human beta 3 Agonists," Biorganic and Medicinal Chemistry Letters, vol. 11, 2001, pp. 757-760—XP002484050.

* cited by examiner

*Primary Examiner* — Deepak Rao
(74) *Attorney, Agent, or Firm* — Millen, White, Zelano & Branigan, P.C.

(57) ABSTRACT

This invention relates to novel aryloxypropanolamines. The invention also relates to the pharmaceutically acceptable salts and solvates containing said compounds, methods for the preparation thereof and to respective synthetic intermediates. Said compounds have agonistic activity at β3 adrenergic receptors and are useful for treatment of ailments influenced by activation of β3 adrenergic receptors.

31 Claims, No Drawings

ARYLOXYPROPANOLAMINES, METHODS OF PREPARATION THEROF AND USE OF ARYLOXYPROPANOLAMINES AS MEDICAMENTS

This application claims the benefit of the filing date of U.S. Provisional Application Ser. No. 60/886,020 filed Jan. 22, 2007, which is incorporated by reference herein.

TECHNICAL FIELD

The present invention relates to novel aryloxypropanolamines and pharmaceutically acceptable salts thereof which are useful as medicaments. The aryloxypropanolamines of the present invention have β3-adrenoceptor agonistic activities and can be used for the treatment or prophylaxis of ailments associated with β3-adrenoceptor activity such as overactive bladder, neurogenic detrusor overactivity, urinary incontinence, benign prostatic hyperplasia, lower urinary tract symptoms, gastrointestinal disorders, dysmenorrhea, tocolysis, obesity, diabetes, anxiety and depression.

BACKGROUND ART

Beta adrenergic receptors, or β-adrenoceptors, are sites on effector tissues or organs that are innervated by post-ganglionic adrenergic fibers of the sympathetic nervous system. The β-adrenoceptors are subclassified in β1-, β2- and β3-adrenoceptors. In general, stimulation of β1-adrenoceptors in the heart causes an increase in heart rate and cardiac contractility, whereas stimulation of β2-adrenoceptors in the smooth muscles of the trachea, of blood vessels and of the uterus leads to bronchodilation, vasodilation and inhibition of uterine contraction.

The β3-adrenoceptor is mainly present in adipocytes, the gall bladder and in the intestinal tract, and it can also be found in the brain, liver, stomach and prostate. Stimulation of these receptors leads to an increase in lipolysis and glucose uptake, inhibition of intestinal motility and anti-depression and anti-anxiety.

Moreover, it has recently been reported that the β3-adrenoceptor is the predominant β-adrenoceptor in the human bladder and that the human bladder is relaxed by β3-adrenoceptor stimulation.

In consequence, it has been found that β3-adrenoceptor stimulating agents are useful for the treatment or prevention of obesity, hyperglycemia, diseases caused by intestinal hypermobility, diseases caused by hypermobility of the biliary tract or by biliary calculi, depression and anxiety, overactive bladder and urinary incontinence, and so on. Efforts are ongoing to develop β3-adrenoceptor stimulating agents for the to treatment or prevention of such diseases but currently no such agent has been marketed yet.

Therefore, it has been desired to develop novel agents with activity at the β3-adrenoceptor and especially with a stimulating effect at this receptor.

Compounds of the 1-aryloxy-2-propanol-3-amine scaffold, in the following simply named aryloxypropanolamine, have been reported as agonists of the β3-adrenoceptor (WO02006221, WO02006230, WO02006235, WO02006255, WO02006258, WO-0100726, WO01036411, WO01017989, WO01044227, WO02094820, WO02006276, WO02038544, WO03024948, WO99051564, WO98041497, WO98037056, WO95004047, WO98022480, WO98007445, U.S. Pat. No. 5,480,908, US20050222247, U.S. Pat. No. 5,451,677, UA20030040530, FR02780057) and also as antagonists of the tachykinin receptor NK1 (WO04014850).

The preparation of a certain β3-receptor construct can be deduced from WO90008775. β3-adrenoceptor agonists were also combined with alpha-adrenoceptor and/or 5-alpha reductase inhibitors, with a serotonin and/or norepinephrine reuptake inhibitor or an agent intervening in the prostaglandin metabolism for treatment of bladder dysfunction (US20050101607, WO05042021, WO04047830, WO05060955).

For an overview of aryloxypropanolamines as β3-ligands, see also M. Sawa et al., Curr. Med. Chem. 2006, 13, 25.

It has now been found that certain novel aryloxypropanolamines are effective as β3-adrenoceptor agonists and are useful in the treatment of medical conditions mediated by β3-adrenoceptors.

According to the present invention compounds are provided having the formula I

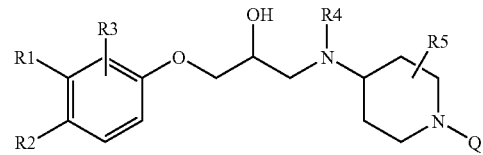

and the pharmaceutically acceptable salt or solvate thereof, wherein

Q is a pyrimidinyl or dihydropyrimidinyl residue that may be unsubstituted or substituted with one or more residues R13, R14, or R15, or Q is a pyrimidin-4-yl or dihydropyrimidin-4-yl ring which is substituted with a group R8 and which may be anellated in the 5,6-position of the pyrimidin-4-yl or dihydropyrimidin-4-yl ring (resulting in a new ringsystem that is anellated in the 2,3-position according to IUPAC) to a five-membered heterocycle, preferably selected from among thiophenyl, furanyl and pyrollyl, which 5-membered heterocycle may be unsubstituted or substituted with one or two substituents selected from R9, R10, R11 or R12;

A person skilled in the art would understand a thiophenyl to be a 5-membered heteroaromatic ring with a sulphur incorporated, also described as thienyl, which might, if not anellated, also be named thiophen-2-yl or thiophen-3-yl being the same as 2-thienyl and 3-thienyl, respectively.

In another embodiment of the invention, Q is a pyrimidinyl or dihydropyrimidinyl residue that might be unsubstituted or substituted with one or more residues R13, R14, or R15, or Q is a pyrimidin-4-yl or dihydropyrimidin-4-yl ring which is substituted with a group R8 and which may be anellated in the 5,6-position of the pyrimidin-4-yl or dihydropyrimidin-4-yl ring (resulting in a new ringsystem that is anellated in the 2,3-position according to IUPAC) to a five-membered heterocycle, preferably thiophenyl, which might be unsubstituted or substituted with one or two substituents selected from R9, R10, R11 or R12;

R1 and R2 are selected from hydrogen, halogen, hydroxyl, carboxy, carbamoyl, sulfamoyl, cyano, nitro, NR6R7, alkyl, alkenyl, alkinyl, alkoxy, alkylcarbonyl, alkoxycarbonyl, alkylcarbonylamino, alkylaminocarbonyl, dialkylaminocarbonyl, arylsulfonylaminomethyl, heteroarylsulfonylaminomethyl, alkylaminosulfonyl, and dialkylaminosulfonyl wherein each alkyl, alkenyl or alkinyl may be unsubstituted or substituted with one or more residues selected from among hydroxyl, alkoxy, fluoro, and NR6R7; and wherein each aryl or heteroaryl is a monocyclic aromatic or heteroaromatic ring, respectively, which can be unsubstituted or substituted with one or more residues selected from among hydroxyl, alkoxy, halogen, alkyl, carboxy, NR6R7, cyano and nitro; provided that if R1 is different from hydroxyl or hydroxymethyl, then R2 must represent hydroxyl or hydroxymethyl;

In another embodiment of the invention, R1 and R2 are selected from hydrogen, halogen, hydroxyl, carboxy, carbamoyl, sulfamoyl, cyano, nitro, NR6R7, alkyl, alkenyl, alkinyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl; provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, alkyl, alkenyl, alkinyl, alkoxy, alkylcarbonyl, and alkoxycarbonyl, wherein each alkyl, alkenyl or alkinyl might be unsubstituted or substituted with one or more residues selected from among hydroxyl, alkoxy, fluoro, and NR6R7;

In another embodiment of the invention, R3 is selected from hydrogen, halogen, hydroxyl, carboxy, carbamoyl, sulfamoyl, cyano, nitro, NR6R7, alkyl, alkenyl, alkinyl, alkoxy, alkylcarbonyl, and alkoxycarbonyl;

R4 is hydrogen, alkylcarbonyl, or alkyl;

R5 is selected from hydrogen, alkyl, wherein alkyl might be unsubstituted or substituted with one or more residues selected from among hydroxyl, alkoxy, fluoro, and NR6R7;

R6 and R7 are independently selected from hydrogen, alkyl, aryl, alkylsulfonyl, arylsulfonyl, heteroarylsulfonyl, alkylcarbonyl, alkoxycarbonyl, aminocarbonyl, alkylaminocarbonyl, arylcarbonyl, and heteroarylcarbonyl; wherein each alkyl might be unsubstituted or substituted with one or more residues selected from among hydroxyl, alkoxy, phenyl, fluoro, carboxy, and NR16R17; and wherein R6 and R7 might form a 5-7 membered cycle; and wherein each aryl or heteroaryl is a monocyclic aromatic or heteroaromatic ring, respectively, which can be unsubstituted or substituted with one or more residues selected from among hydroxyl, alkoxy, halogen, alkyl, carboxy, NR16R17, cyano and nitro;

R8 is selected from among hydrogen, alkyl, hydroxyl, alkoxy;

R9, R10, R11 and R12 are independently selected from hydrogen, carboxy, NR6R7, alkyl and a mono- or bicyclic aromatic or heteroaromatic ring, wherein each alkyl may be unsubstituted or substituted with one or more residues selected from among hydroxyl, alkoxy, fluoro, NR6R7, and carboxy, and wherein each mono- or bicyclic aromatic or heteroaromatic ring can be unsubstituted or substituted with one or more residues selected from among alkyl, hydroxyl, alkoxy, alkylthio, alkylcarbonyl, alkylaminocarbonyl, dialkylaminocarbonyl, alkoxycarbonyl, carboxymethoxy, alkoxy-carbonylalkoxy, halogen, carboxy, carbamoyl, sulfamoyl, alkylaminosulfonyl, dialkylaminosulfonyl, alkylsulfonyl, sulfo, alkylsulfinyl, NR6R7, cyano and nitro, wherein two of these residues might form a 5-7 membered non-aromatic ring.

Alternatively, R9, R10, R11 and R12 are defined as above wherein each mono- or bicyclic aromatic or heteroaromatic ring can additionally be substituted with one or more carboxyalkoxy residues;

In another embodiment of the invention, R9, R10, R11 and R12 are independently selected from hydrogen, carboxy, NR6R7, alkyl and a mono- or bicyclic aromatic or heteroaromatic ring;

R13, R14 and R15 are independently selected from hydrogen, alkyl, carboxy, NR6R7, aryl, heteroaryl, hydroxyl, alkoxy, alkoxycarbonyl, arylaminocarbonyl, heteroarylaminocarbonyl, halogen and nitro, wherein each alkyl might be unsubstituted or substituted with one or more residues selected from among hydroxyl, alkoxy, fluoro and aryl; and wherein two of these residues (selected from R13, R14, R15) might form a 5-7 membered non-aromatic or aromatic ring;

and wherein each aryl or heteroaryl is a monocyclic aromatic or heteroaromatic ring, respectively, which can be unsubstituted or substituted with one or more residues selected from among hydroxyl, alkoxy, halogen, carboxy, alkoxycarbonyl, NR6R7, cyano and nitro; wherein two of these residues might form a 5-7 membered non-aromatic ring.

R16 and R17 are independently selected from among hydrogen, C1-C8 alkyl, phenyl, thiophenyl, pyridyl C1-C8 alkylsulfonyl, phenylsulfonyl, thiophenylsulfonyl, pyridylsulfonyl C1-C8 alkylcarbonyl, C1-C8 alkoxycarbonyl, aminocarbonyl, C1-C8 alkylaminocarbonyl, thiophenylcarbonyl, pyridylcarbonyl, and phenylcarbonyl and wherein R16 and R17 may form a 5-7 membered cycle.

In the context of the present invention, an alkyl group, if not stated otherwise, denotes a linear or branched $C_1$-$C_6$-alkyl, preferably a linear or branched chain of one to six carbon atoms; an alkenyl group, if not stated otherwise, denotes a linear or branched $C_2$-$C_6$-alkenyl; and an alkinyl group, if not stated otherwise, denotes a linear or branched $C_2$-$C_6$-alkinyl group, which may be substituted by one or more substituents R'.

To keep the definitions as short as possible, in the following paragraphs "alkyl" is to be understood to encompass alkyl, alkenyl and alkinyl.

In another embodiment of the invention, an alkyl group, if not stated otherwise, denotes a linear or branched $C_1$-$C_{12}$ alkyl, $C_2$-$C_6$-alkenyl and $C_2$-$C_6$-alkinyl group, which may be substituted by one or more substituents R'.

In another embodiment of the invention, in the context of the present invention, an alkyl group, if not stated otherwise, denotes a linear or branched $C_1$-$C_6$-alkyl and preferably a $C_1$-$C_3$ alkyl; $C_2$-$C_6$-alkenyl and $C_2$-$C_6$-alkinyl group, which might be optionally substituted by one or more substituents R'.

The $C_1$-$C_6$-alkyl, $C_2$-$C_6$-alkenyl and $C_2$-$C_6$-alkinyl residue may be selected from the group consisting of —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C(R')$_3$, —$C_2$(R')$_5$, —$CH_2$—C(R')$_3$, —$C_3$(R')$_7$, —$C_2H_4$—C(R')$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—CH=C($CH_3$)$_2$, —C($CH_3$)=C($CH_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=CH—C($CH_3$)=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH $(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_4H_8$—$CH$═$CH_2$, —$CH$═$CH$—$C_4H_9$, —$C_3H_6$—$CH$═$CH$—$CH_3$, —$CH_2$—$CH$═$CH$—$C_3H_7$, $C_2H_4$—$CH$═$CH$—$C_2H_5$, —$CH_2$—$C(CH_3)$═$C(CH_3)_2$, —$C_2H_4$—$CH$═$C(CH_3)_2$, —$C_4H_8$—$C$═$CH$, —$C$═$C$—$C_4H_9$, —$C_3H_6$—$C$═$C$—$CH_3$, —$CH_2$—$C$═$C$—$C_3H_7$, and —$C_2H_4$—$C$═$C$—$C_2H_5$;

R' independently represents H, —$CO_2R''$, —$CONHR''$, —$CR''O$, —$SO_2NHR''$, —$NR''$-CO-haloalkyl, —$NO_2$, —$NR''$—$SO_2$-haloalkyl, —$NR''$-$SO_2$-alkyl, —$SO_2$-alkyl, —$NR''$-CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, aryl, arylalkyl or heteroaryl;

R'' independently represents H, haloalkyl, hydroxyalkyl, alkyl, cycloalkyl, aryl, heteroaryl or aminoalkyl;

In another embodiment of the invention, R' independently represents H, —$CO_2R''$, —$CONR''R'''$, —$CR''O$, —$SO_2NR''R'''$, —$NR''$-CO-haloalkyl, —$NO_2$, —$NR''$-$SO_2$-haloalkyl, —$NR''$-$SO_2$-alkyl, —$NR''$-$SO_2$-aryl, —$NR''$-$SO_2$-heteroaryl, —$SO_2$-alkyl, —$SO_2$-aryl, —$SO_2$-heteroaryl, —SO-alkyl, NR''-CO-alkyl, —NR''-CO-aryl, —NR''-CO-heteroaryl, —NR''—CO—NR'''R$^{iv}$, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, aryl, arylalkyl, heteroaryl, aryloxy or heteroaryloxy; wherein two R' can form ═O;

in this other embodiment of the invention, R'', R''', R$^{iv}$ independently represent H, haloalkyl, hydroxyalkyl, alkoxyalkyl, alkyl, cycloalkyl, aryl, heteroaryl or aminoalkyl;

a cycloalkyl group denotes a non-aromatic ring system containing three to eight carbon atoms, preferably four to eight carbon atoms, wherein one or more of the carbon atoms in the ring may be substituted by a group E, E being O, S, SO, $SO_2$, N, or NR'', R'' being as defined above; the $C_3$-$C_8$-cycloalkyl residue may be selected from the group consisting of -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperidinyl, piperazinyl, and 1-alkylpiperazine-4-yl;

a heterocyclyl group denotes a 3 to 8-membered heterocyclic non-aromatic group which contains at least one heteroatom selected from O, N, and S, wherein the heterocyclyl group may be fused to another non-aromatic ring and may be substituted by one or more substituents R', wherein R' is as defined above;

A person skilled in the art would understand that in the context of this invention, heterocyclyl might be a representative of cycloalkyl as defined above;

In another embodiment of the invention, a cycloalkyl group denotes a non-aromatic ring system containing three to eight carbon atoms, preferably five to seven carbon atoms, which might be optionally substituted by one or more substituents R', and wherein one or more of the carbon atoms in the ring may be replaced by a group E, E being O, S, SO, $SO_2$, N, or NR'', R' and R'' being as defined above; the $C_3$-$C_8$-cycloalkyl residue might be selected from the group consisting of -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperidinyl, piperazinyl, and 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group; alternatively, an alkoxy group is defined as above but might likewise preferably be abenzyloxy group;

an alkylthio group denotes a S-alkyl group, the alkyl group being as defined above;

a haloalkyl group denotes an alkyl group which is substituted by one to five halogen atoms, the alkyl group being as defined above; the haloalkyl group is preferably a —$C(R18)_3$, —$CR18(R18')_2$, —$CR18(R18)R18''$, —$C_2(R18)_5$, —$CH_2$—$C(R18)_3$, —$CH_2$—$CR18(R18')_2$, —$CH_2$—$CR18(R18')R18''$, —$C_3(R18)_7$, or —$C_2H_4$—$C(R18)_3$, wherein R18, R18', R18'' represent F, Cl, Br or I, preferably F;

alternatively, a haloalkyl group denotes an alkyl group which is substituted by one to seven halogen atoms, which is preferably chosen as defined above but might also represent —$CH(R18)_2$;

a hydroxyalkyl group denotes a HO-alkyl group, the alkyl group being as defined above;

a haloalkoxy group denotes an alkoxy group which is substituted by one to seven halogen atoms, the alkyl group being as defined above; the haloalkoxy group is preferably a —$OC(R18)_3$, —$OCR18(R18')_2$, —$OCR18(R18')R18''$, —$OC_2(R18)_5$, —$OCH_2$—$C(R18)_3$, —$OCH_2$—$CR18(R18')_2$, —$OCH_2$—$CR18(R18')R18''$, —$OC_3(R18)_7$, —$OC_2H_4$—$C(R18)_3$, wherein R18, R18', R18'' represent F, Cl, Br or I, preferably F;

alternatively, a haloalkoxyl group denotes an alkoxyl group which is substituted by one to seven halogen atoms, which is preferably chosen as defined above but might also represent —$OCH(R18)_2$, $OC2H4(R18)$, —$OC_2(R18)$, $OC_2(R18)_3$, —$OC(R18)$═$C(R18)$-, or —$OCH$═$C(R18)$-;

a hydroxyalkylamino group denotes a (HO-alkyl)$_2$-N— group or HO-alkyl-NH— group, the alkyl group being as defined above;

an alkylamino group denotes a HN-alkyl or N-dialkyl group, the alkyl group being as defined above;

Alternatively, an alkylamino group denotes a HN-alkyl or N-dialkyl group, the alkyl group being as defined above and might be defined independently from each other;

a halogen group is fluorine, chlorine, bromine, or iodine;

an aryl group denotes an aromatic group having five to fifteen carbon atoms, which may be substituted by one or more substituents R', and may be fused to another aromatic ring, where R' is as defined above; the aryl group is preferably a phenyl group, -o-$C_6H_4$—R', -m-$C_6H_4$—R', -p-$C_6H_4$—R', 1-naphthyl, 2-naphthyl, 1-anthracenyl or 2-anthracenyl;

In another embodiment of the invention, an aryl group denotes an aromatic group having five to fifteen carbon atoms, preferably having five to ten carbon atoms, which might be optionally substituted by one or more substituents R', and might be fused to another aromatic ring, where R' is as defined above; the aryl group is preferably a phenyl group, -o-$C_6H_4$—R', -m-$C_6H_4$—R', -p-$C_6H_4$—R', —$C_6H_3R'_2$, —$C_6H_2R'_3$, 1-naphthyl or 2-naphthyl, R' groups might be defined independently from each other; R' groups might form a 5-7 membered non-aromatic ring;

a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, benzooxazol-2-yl, benzooxazol-4-yl, benzooxazol-5-yl, benzoisooxazol-3-yl, benzoisooxazol-4-yl, benzoisooxazol-5-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, benzoisothiazol-3-yl, benzoisothiazol-4-yl, benzoisothiazol-5-yl, 1,2,5-thiadiazol-3-yl, 1-imidazolyl, 2-imidazolyl, 1,2,5-thiadiazol-4-yl, 4-imidazolyl, benzoimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, 6-pyrimidinyl, 2,4-dimethoxy-6-pyrimidinyl, benzimidazol-2-yl, 1H-benzimidazolyl, benzimidazol-4-yl, benz-imidazol-5-yl, benzimidazol-6-yl, benzimidazol-7-yl, tetrahydro-thieno[3,4-d]imidazol-2-one, pyrazolo[5,1-c][1,2,4]triazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, or triazolopyridazine group. This heterocyclic group may be substituted by one or more substituents R', wherein R' is as defined above;

The compositions might take suitable forms for oral administration such as solid dosage forms (e.g. tablets, pills, capsules, granulates, pellets, powders, multi-particulate formulations such as beads, granules or crystals and dragees) or oral liquid forms (e.g. solutions, droplets syrups, emulsions, suspensions).

The compositions described herein can be administered transdermally, e.g. in the form of transdermal therapeutic systems (e.g. patches) or topical formulations (e.g. powder, liposomes, crèmes, ointment, lotion, gels, dispersion, suspension, spray, solution). Topical formulations can also be administered via the buccal, vaginal, ocular, pulmonary or nasal route.

The compositions might take suitable sterile forms for parenteral administration (for instance intravenous, intramuscular or subcutaneous application) such as solutions, suspension, dispersion of colloidal drug carriers, or lyophilized form of the above mentioned sterile lipid forms for re-constitution with a suitable vehicle, e.g. sterile, pyrogen-free water, before use.

The compositions described herein can also be administered rectal or vaginal as semisolid therapeutic systems (e.g. ovula or suppository).

"Pharmaceutically acceptable" means being approved by a regulatory agency of the Federal or a state government or being listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. These salts are selected but not limited to the group consisting of acetate, 2,2-dichloroacetate, tert-butylacetate, trimethylacetate, adipate, alginate, ascorbate, aspartate, benzoate, 3-(4-hydroxybenzoyl)benzoate, benzenesulfonate, 4-chlorobenzenesulfonate, 2-acetamidobenzoate, caproate, caprate, camphorate, camphorsulfonate, cinnamate, citrate, cyclamate, cyclopentanepropionate, laurylsulfate, edisilate, esylate or ethanesulfonate, 1,2-ethanedisulfonate, 2-hydroxyethanesulfonate, isetionate, formate, fumarate, galactarate, gentisate, gluceptate, glucoheptonate, gluconate, glucuronate, glutamate, oxoglutarate, glycolate, hexanoate, hippurate, bromide or hydrobromide, chloride or hydrochloride, hydroxynaphthoate, lactate, lactobionate, lauryl sulfate, malate, maleate, malonate, mandelate, mesylate, 4-methylbicyclo-[2.2.2]-oct-2-ene-1-carboxylate, muconate, napsilate or naphthalene-2-sulfonate, napadisilate, xinafoate, nicotinate, nitrate, oleate, orotate, oxalate, palmitate, pyruvate, embonate, phosphate, hydrogenphosphate or dihydrogenphosphate, pidolate, propionate, 3-phenylpropionate, salicilate, p-aminosalicylate, sebacate, stearate, succinate, sulfate or hydrogensulfate, tannate, tartrate, rhodanide, tosylate, undecylenate, ammonia, arginine, benethamine, benzathine, calcium, choline, deanol, diethanolamine, diethylammonium, ethanolamine, ethylendiamine, meglumine, hydrabamine, imidazole, lysine, magnesium, hydroxyethylmorpholine, piperazine, potassium, epolamine, sodium, trolamine, tromethamine or zinc [Handbook of Pharmaceutical Salts, Ed. P. H. Stahl, C. G. Wermuth, Zurich 2002].

The term "salt" as used in the present application is meant to encompass crystalline as well as amorphous forms. It is clear to the skilled artisan that various polymorphs of a given salt can exist. The term "salt" in this application encompasses the particular polymorphs as well as mixtures of various polymorphs.

The term "solvate" hereby includes stoichiometric as well as non-stoichiometric inclusions of solvents such as e.g. ethanol or isobutylacetate into the crystal structure. The term "solvate" also includes hydrates wherein water is included in the crystal structure.

According to the present invention compounds are preferred according to formula I, wherein

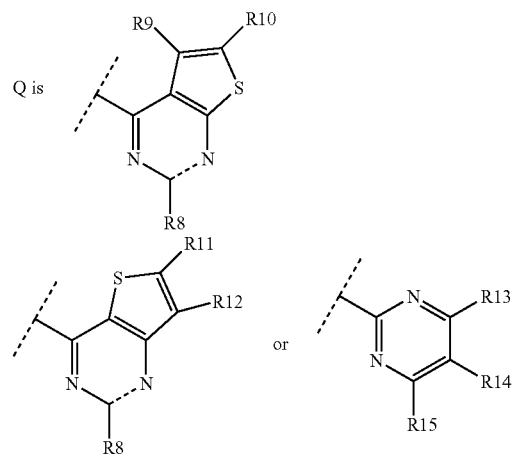

wherein the dotted bond represents a single or a double bond;

R1 and R2 are selected from hydrogen, halogen, hydroxyl, carboxy, carbamoyl, sulfamoyl, cyano, nitro, NR6R7, C1-C6 alkyl, C2-C6 alkenyl, C2-C6 alkinyl, C1-C6 alkoxy, C1-C6 alkylcarbonyl, C1-C6 alkoxycarbonyl, C1-C6 alkylcarbonylamino, C1-C6 alkylaminocarbonyl, di(C1-C6)alkylaminocarbonyl, phenylsulfonylaminomethyl, thiophenylsulfonylaminomethyl, alkylaminosulfonyl, and dialkylaminosulfonyl, wherein each alkyl, alkenyl or alkinyl might be unsubstituted or substituted with one or more residues selected from among hydroxyl, C1-C6 alkoxy, fluoro, and NR6R7; and wherein each phenyl or thiophenyl may be unsubstituted or substituted with one or more residues selected from among hydroxyl, C1-C6 alkoxy, halogen, C1-C6 alkyl, carboxy, NR6R7, cyano and nitro, provided that if R1 is different from hydroxyl or hydroxymethyl, then R2 must represent hydroxyl or hydroxymethyl;

In another preferred embodiment, R1 and R2 are selected from hydrogen, halogen, hydroxyl, carboxy, carbamoyl, sulfamoyl, cyano, nitro, NR6R7, C1-C6 alkyl, C2-C6 alkenyl, C2-C6 alkinyl, C1-C6 alkoxy, C1-C6 alkylcarbonyl, C1-C6 alkoxycarbonyl, C1-C6 alkylcarbonylamino, C1-C6 alkylaminocarbonyl, to phenylsulfonylaminomethyl, thiophenylsulfonylaminomethyl and C1-C6 alkylaminosulfonyl, wherein each alkyl might be unsubstituted or substituted with one or more residues preferably selected from among hydroxyl, C1-C6 alkoxy, fluoro, and NR6R7; and wherein each phenyl or thiophenyl might be unsubstituted or substituted with one or more residues preferably selected from among hydroxyl, C1-C6 alkoxy, halogen, C1-C6 alkyl, carboxy, NR6R7, cyano and nitro, provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, C1-C6 alkyl, C2-C6 alkenyl, C2-C6 alkinyl, C1-C6 alkoxy, C1-C6 alkylcarbonyl, and C1-C6 alkoxycarbonyl, wherein each alkyl, alkenyl or alkinyl may be unsubstituted or substituted with one or more residues selected from among hydroxyl, C1-C6 alkoxy, fluoro, and NR6R7;

R4 is hydrogen, C1-C3 alkylcarbonyl, or C1-C3 alkyl;

R5 is selected from hydrogen, C1-C3 alkyl, which might be unsubstituted or substituted with one or more residues selected from among hydroxyl, C1-C3 alkoxy, fluoro, and NR6R7;

R6 and R7 are independently selected from hydrogen, C1-C8 alkyl, phenyl, C1-C8 alkylsulfonyl, phenylsulfonyl, thiophenylsulfonyl, C1-C8 alkylcarbonyl, C1-C6 alkoxycarbonyl, aminocarbonyl, C1-C8 alkylaminocarbonyl, phenylcarbonyl, and thiophenylcarbonyl; wherein each alkyl might be unsubstituted or substituted with one or more residues selected from among hydroxyl, C1-C6 alkoxy, phenyl, fluoro, carboxy, and NR16R17; and wherein R6 and R7 might form a 5-7 membered cycle; and wherein each phenyl or thiophenyl might be unsubstituted or substituted with one or more residues selected from among hydroxyl, C1-C6 alkoxy, halogen, C1-C6 alkyl, carboxy, NR16R17, cyano and nitro;

R8 is selected from hydrogen, methyl, hydroxyl, and methoxy;

R9, R10, R11 and R12 are independently selected from hydrogen, carboxy, NR6R7, C1-C6 alkyl and a mono- or bicyclic aromatic or heteroaromatic ring selected from phenyl, furanyl, thiophenyl, pyrollyl, thiazolyl, oxazolyl, imidazolyl, pyrazolyl, isoxazolyl, isothiazolyl, triazolyl, oxydiazolyl, thiadiazolyl, pyranyl, pyridinyl, pyridazinyl, pyrimidinyl, pyrazinyl, triazinyl and tetrazinyl, or a bicyclic aromatic or heteroaromatic ring selected from quinolinyl, quinoxalinyl, indolyl, benzofuranyl, benzothiophenyl, benzooxazolyl, benzothiazolyl and naphthalyl wherein each alkyl may be unsubstituted or substituted with one or more residues selected from among hydroxyl, C1-C6 alkoxy, fluoro, NR6R7, and carboxy; and wherein each mono- or bicyclic aromatic or heteroaromatic ring can be unsubstituted or substituted with one or more residues selected from among C1-C6 alkyl, hydroxyl, C1-C4 alkoxy, C1-C4 alkylthio, C1-C4 alkylcarbonyl, C1-C6 alkylaminocarbonyl, di(C1-C6)alkylaminocarbonyl, C1-C4 alkoxycarbonyl, carboxymethoxy, C1-C4 alkoxycarbonyl(C1-C4)alkoxy, halogen, carboxy, carbamoyl, sulfamoyl, C1-C4 alkylaminosulfonyl, di(C1-C4)alkylaminosulfonyl, C1-C4 alkylsulfonyl, sulfo, C1-C4 alkylsulfinyl, NR6R7, cyano and nitro; wherein two of these residues might form a 5-7 membered non-aromatic ring;

Alternatively, R9, R10, R11 and R12 are defined as above wherein each mono- or bicyclic aromatic or heteroaromatic ring can additionally be substituted with one or more carboxy(C1-C4)alkoxy residues;

R13, R14 and R15 are independently selected from hydrogen, C1-C4 alkyl, carboxy, NR6R7, phenyl, hydroxyl, C1-C4 alkoxy, C1-C4 alkoxycarbonyl, phenylaminocarbonyl, thiophenylaminocarbonyl, halogen and nitro, wherein each alkyl might be unsubstituted or substituted with one or more residues selected from among hydroxyl, C1-C4 alkoxy, fluoro and phenyl; wherein two of these residues selected from R13, R14 and R15 might form a 5-7 membered non-aromatic or aromatic ring;

and wherein phenyl or thiophenyl can be unsubstituted or substituted with one or more residues selected from among hydroxyl, C1-C4 alkoxy, halogen, carboxy, C1-C4 alkoxycarbonyl, NR6R7, cyano and nitro; wherein two of these residues might form a 5-7 membered non-aromatic ring.

Alternatively, R13, R14 and R15 are defined as above and can additionally be selected from C1-C3 haloalkyl;

R16 and R17 are independently selected from among hydrogen, C1-C6 alkyl, phenyl, C1-C6 alkylsulfonyl, phenylsulfonyl, thiophenylsulfonyl, C1-C6 alkylcarbonyl, C1-C6 alkoxycarbonyl, aminocarbonyl, C1-C6 alkylaminocarbonyl, phenylcarbonyl, and thiophenylcarbonyl wherein R16 and R17 might form a 5-7 membered cycle.

Especially preferred are compounds according to formula I, wherein

Q is

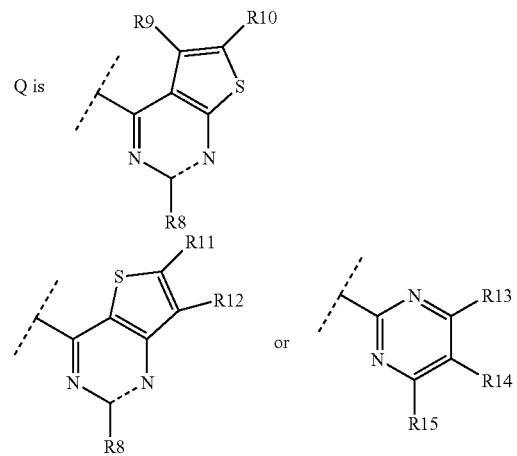

wherein the dotted bond represents a single or a double bond;

R1 and R2 are selected from hydrogen, halogen, hydroxyl, carboxy, cyano, nitro, sulfamoyl, NR6R7, C1-C3 alkyl, C2-C3 alkenyl, ethinyl, C1-C3 alkoxy, C1-C3 alkylcarbonyl, C1-C3 alkoxycarbonyl, C1-C4 alkylaminocarbonyl, morpholinocarbonyl, thiophen-2-ylsulfonylaminomethyl, wherein each alkyl or alkenyl might be unsubstituted or substituted with one or more residues selected from among hydroxyl, C1-C3 alkoxy, fluoro, and NR6R7; and wherein the thiophenyl can be unsubstituted or substituted with one or more residues selected from among hydroxyl, C1-C3 alkoxy, halogen, C1-C3 alkyl, carboxy, NR6R7, cyano and nitro, provided that if R1 is different from hydroxyl or hydroxymethyl, then R2 must represent hydroxyl or hydroxymethyl;

In another especially preferred embodiment, R1 and R2 are selected from hydrogen, halogen, hydroxyl, carboxy, carbamoyl, cyano, nitro, sulfamoyl, NR6R7, C1-C3 alkyl, C2-C3 alkenyl, ethinyl, C1-C3 alkoxy, C1-C3 alkylcarbonyl, C1-C3 alkoxycarbonyl, C1-C4 alkylaminocarbonyl, morpholinocarbonyl, thiophen-2-ylsulfonylaminomethyl, wherein each alkyl might be unsubstituted or substituted with one or more residues preferably selected from among hydroxyl, C1-C3 alkoxy, fluoro, and NR6R7; and wherein the thiophenyl can be unsubstituted or substituted with one or more residues preferably selected from among hydroxyl, C1-C3 alkoxy, halogen, C1-C3 alkyl, carboxy, NR6R7 and cyano, provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, C1-C3 alkyl, C2-C3 alkenyl, ethinyl, C1-C3 alkoxy, C1-C3 alkylcarbonyl, and C1-C3 alkoxycarbonyl, wherein each alkyl or alkenyl may be unsubstituted or substituted with one or more residues selected from among hydroxyl, C1-C3 alkoxy, fluoro, and NR6R7;

R4 is hydrogen or methyl;

R5 is selected from hydrogen and methyl, wherein methyl might be unsubstituted or substituted with a residue selected from among hydroxyl, methoxy, ethoxy, fluoro, and NR6R7;

Alternatively, R5 is selected from hydrogen and methyl, wherein methyl might be unsubstituted or substituted with one or more residues selected from among hydroxyl, methoxy, ethoxy, fluoro, and NR6R7;

R6 and R7 are independently selected from hydrogen, C1-C3 alkyl, C1-C8 alkylsulfonyl, thiophen-2-ylsulfonyl, C1-C8 alkylcarbonyl, C1-C4 alkoxycarbonyl, aminocarbonyl, and C1-C8 alkylaminocarbonyl; wherein each alkyl might be unsubstituted or substituted with one or more residues selected from among hydroxyl, alkoxy preferred, C1-C3 alkoxy, carboxy, and NR16R17; and wherein R6 and R7 might form a 5-7 membered cycle; and wherein the thiophenyl might be unsubstituted or substituted with one or more residues selected from among hydroxyl, C1-C3 alkoxy, halogen, C1-C3 alkyl, carboxy, NR16R17 and cyano;

R8 is selected from hydrogen and methyl;

R9, R10, R11 and R12 are independently selected from hydrogen, NR6R7, C1-C6 alkyl, phenyl, thiophenyl, pyridinyl, wherein each alkyl may be unsubstituted or substituted with one or more residues selected from among hydroxyl, C1-C3 alkoxy, fluoro, NR6R7, and carboxy; and wherein each monocyclic aromatic or heteroaromatic ring can be unsubstituted or substituted with one or more residues selected from among C1-C3 alkyl, hydroxyl, C1-C4 alkoxy, C1-C4 alkoxycarbonyl, carboxymethoxy, C1-C3 alkoxycarbonyl(C1-C2) alkoxy, preferably 2-alkoxy-2-oxoethoxy, halogen, carboxy, NR6R7 and cyano; wherein two of these residues might form a 5-7 membered non-aromatic ring;

Alternatively, R9, R10, R11 and R12 are defined as above and can additionally be selected from furanyl; wherein each monocyclic aromatic or heteroaromatic ring can additionally be substituted with one or more residues selected from C1-C4 alkylaminocarbonyl and carboxy (C1-C2)alkoxy;

R13, R14 and R15 are independently selected from hydrogen, C1-C3 alkyl, carboxy, NR6R7, phenyl, hydroxyl, C1-C3 alkoxy, C1-C3 alkoxycarbonyl, phenylaminocarbonyl, halogen and nitro, wherein each alkyl may be unsubstituted or substituted with one or more residues selected from among hydroxyl, C1-C3 alkoxy, fluoro and phenyl; and wherein phenyl can be unsubstituted or substituted with one or more residues selected from among hydroxyl, C1-C3 alkoxy, halogen, carboxy, C1-C3 alkoxycarbonyl, NR6R7 and cyano; wherein two of these residues might form a 5-7 membered non-aromatic ring.

Alternatively, R13, R14 and R15 are defined as above and can additionally be selected from CF3;

R16 and R17 are independently selected from among hydrogen, C1-C3 alkyl, C1-C4 alkylsulfonyl, thiophen-2-ylsulfonyl, C1-C4 alkylcarbonyl, C1-C4 alkoxycarbonyl, aminocarbonyl, and C1-C4 alkylaminocarbonyl wherein R16 and R17 may form a 5-7 membered cycle.

Another preferred embodiment according to the present invention are compounds according to formula I, wherein R1 is selected from hydrogen, hydroxyl, hydroxymethyl, methoxycarbonyl, ethoxycarbonyl, methyl, ethyl, carboxy, and methoxymethyl;

R2 is selected from hydrogen, hydroxyl, methoxycarbonyl, and hydroxymethyl;

R3 is selected from hydrogen, methyl, ethyl, methoxycarbonyl, ethoxycarbonyl, carboxy, hydroxymethyl;

R4 is hydrogen or methyl;

R5 is hydrogen or methy;

R8 is hydrogen or methyl;

R9, if present, is hydrogen, methyl, unsubstituted phenyl, halophenyl, preferably para-fluoro phenyl, or thiophenyl;

R10, if present, is hydrogen, methyl, unsubstituted phenyl, or halophenyl;

R11 and R12, if present, are both hydrogen;

R13, R14 and R15, if present, are independently selected from hydrogen and methyl.

Another preferred embodiment according to the present invention are compounds according to formula I, wherein the dotted bond represents a single or a double bond; and wherein R1 is selected from hydrogen, halogen, hydroxyl, hydroxymethyl, methoxycarbonyl, ethoxycarbonyl, methyl, ethyl, carboxy, and methoxymethyl;

R2 is selected from hydrogen, hydroxyl, methoxycarbonyl, carboxy, and hydroxymethyl;

R3 is selected from hydrogen, halogen, methyl, ethyl, methoxycarbonyl, ethoxycarbonyl, carboxy, hydroxymethyl;

R4 is hydrogen or methyl;

R5 is hydrogen or methyl;

R8 is hydrogen or methyl;

R9, if present, is hydrogen, methyl, unsubstituted phenyl, halophenyl, preferably para-fluorophenyl, or thiophenyl;

R10, if present, is hydrogen, methyl, unsubstituted phenyl, or halophenyl;

R11 and R12, if present, are both hydrogen;

R13, R14 and R15, if present, are independently selected from hydrogen and methyl.

According to the present invention compounds according to formula I are preferred, or the pharmaceutically acceptable salt or solvate thereof, in the form of a racemate or as a substantially pure enantiomer or diastereomer or mixtures of the optical isomers, and having the formula II

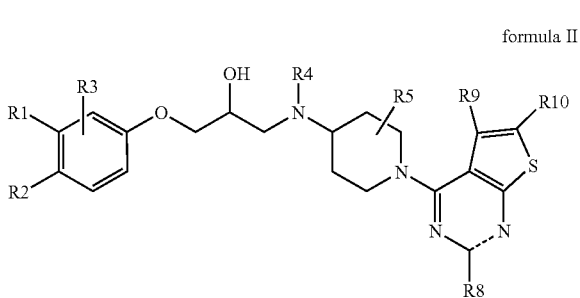

formula II wherein R1, R2, R3, R4, R5, R8, R9 and R10 are as defined as above for formula I.

Another preferred embodiment of the present invention encompass the above described compounds whereas R9 is hydrogen, carboxy, NR6R7, C1-C6 alkyl and a mono- or bicyclic aromatic or heteroaromatic ring selected from phenyl, furanyl, thiophenyl, pyrollyl, thiazolyl, oxazolyl, imidazolyl, pyrazolyl, isoxazolyl, isothiazolyl, triazolyl, oxydiazolyl, thiadiazolyl, pyranyl, pyridinyl, pyridazinyl, pyrimidinyl, pyrazinyl, triazinyl and tetrazinyl, or a bicyclic aromatic or heteroaromatic ring selected from quinolinyl, quinoxalinyl, indolyl, benzofuranyl, benzothiophenyl, benzooxazolyl, benzothiazolyl and naphthalyl, wherein each alkyl may be unsubstituted or substituted with one or more residues selected from among hydroxyl, C1-C6 alkoxy, fluoro, NR6R7, and carboxy; and wherein each mono- or bicyclic aromatic or heteroaromatic ring can be unsubstituted or substituted with one or more residues selected from among C1-C6 alkyl, hydroxyl, C1-C4 alkoxy, C1-C4 alkylthio, C1-C4 alkylcarbonyl, C1-C6 alkylaminocarbonyl, di(C1-C6)alkylaminocarbonyl, C1-C4 alkoxycarbonyl, carboxymethoxy, C1-C4 alkoxycarbonyl(C1-C4)alkoxy, halogen, carboxy, carbamoyl, sulfamoyl, C1-C4 alkylaminosulfonyl, di(C1-C4)alkylaminosulfonyl, C1-C4 alkylsulfonyl, sulfo, C1-C4 alkylsulfinyl, NR6R7, cyano and nitro; wherein two of these residues might form a 5-7 membered non-aromatic ring; and R10 is hydrogen or C1-C6 alkyl, wherein the C1-C6 alkyl may be unsubstituted or substituted with one or more residues selected from among hydroxyl, C1-C3 alkoxy, or fluoro;

Another preferred embodiment of the present invention are compounds according to formula II, wherein R9 is hydrogen or C1-C6 alkyl, wherein the C1-C6 alkyl may be unsubstituted or substituted with one or more residues selected from among hydroxyl, C1-C3 alkoxy, or fluoro;

and

R10 is hydrogen, carboxy, NR6R7, C1-C6 alkyl and a mono- or bicyclic aromatic or heteroaromatic ring selected from phenyl, furanyl, thiophenyl, pyrollyl, thiazolyl, oxazolyl, imidazolyl, pyrazolyl, isoxazolyl, isothiazolyl, triazolyl, oxydiazolyl, thiadiazolyl, pyranyl, pyridinyl, pyridazinyl, pyrimidinyl, pyrazinyl, triazinyl and tetrazinyl, or a bicyclic aromatic or heteroaromatic ring selected from quinolinyl, quinoxalinyl, indolyl, benzofuranyl, benzothiophenyl, benzooxazolyl, benzothiazolyl and naphthalyl, wherein each alkyl may be unsubstituted or substituted with one or more residues selected from among hydroxyl, C1-C6 alkoxy, fluoro, NR6R7, and carboxy; and wherein each mono- or bicyclic aromatic or heteroaromatic ring can be unsubstituted or substituted with one or more residues selected from among C1-C6 alkyl, hydroxyl, C1-C4 alkoxy, C1-C4 alkylthio, C1-C4 alkylcarbonyl, C1-C6 alkylaminocarbonyl, di(C1-C6)alkylaminocarbonyl, C1-C4 alkoxycarbonyl, carboxymethoxy, C1-C4 alkoxycarbonyl(C1-C4)alkoxy, halogen, carboxy, carbamoyl, sulfamoyl, C1-C4 alkylaminosulfonyl, di(C1-C4)alkylaminosulfonyl, C1-C4 alkylsulfonyl, sulfo, C1-C4 alkylsulfinyl, NR6R7, cyano and nitro; wherein two of these residues might form a 5-7 membered non-aromatic ring.

Another preferred embodiment of the present invention are compounds according to formula II, wherein the dotted bond represents a single or a double bond; and wherein R1 and R2 are selected from hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, provided that if R1 is different from hydroxyl or hydroxymethyl, then R2 must represent hydroxyl or hydroxymethyl;

In another embodiment of the invention, R1 and R2 are selected from hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, wherein each alkyl, may be unsubstituted or substituted with one or more residues, which are preferably selected from among hydroxyl, alkoxy, fluoro, and NR6R7; and wherein each aryl or heteroaryl is a monocyclic aromatic or heteroaromatic ring, respectively, which can be unsubstituted or substituted with one or more residues, which are preferably selected from among hydroxyl, alkoxy, halogen, alkyl, carboxy, NR6R7, cyano and nitro; provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, alkyl, alkoxy, alkylcarbonyl, and alkoxycarbonyl;

In another embodiment of the invention, R3 is selected from hydrogen, halogen, hydroxyl, carboxy, carbamoyl, sulfamoyl, cyano, nitro, NR6R7, alkyl, alkoxy, alkylcarbonyl, and alkoxycarbonyl, wherein each alkyl, might be unsubstituted or substituted with one or more residues, which are preferably selected from among hydroxyl, alkoxy, fluoro, and NR6R7;

R4 is hydrogen, alkylcarbonyl, or alkyl;

R5 is selected from hydrogen, alkyl, wherein alkyl might be unsubstituted or substituted with one or more residues, which are preferably selected from among hydroxyl, alkoxy, fluoro, and NR6R7;

R6 and R7 are independently selected from hydrogen, alkyl, aryl, alkylsulfonyl, arylsulfonyl, heteroarylsulfonyl, alkylcarbonyl, alkoxycarbonyl, aminocarbonyl, alkylaminocarbonyl, arylcarbonyl, and heteroarylcarbonyl; wherein each alkyl might be unsubstituted or substituted with one or more residues, which are preferably selected from among hydroxyl, alkoxy, phenyl, fluoro, carboxy, and NR16R17; and wherein R6 and R7 might form a 5-7 membered cycle; and wherein each aryl or heteroaryl is a monocyclic aromatic or heteroaromatic ring, respectively, which can be unsubstituted or substituted with one or more residues, which are preferably selected from among hydroxyl, alkoxy, halogen, alkyl, carboxy, NR16R17, cyano and nitro;

R8 is selected from among hydrogen, alkyl, hydroxyl, alkoxy;

R9 and R10 are independently selected from hydrogen, carboxy, NR6R7, alkyl and a mono- or bicyclic aromatic or heteroaromatic ring, In another embodiment of the invention, R9 and R10 are independently selected from hydrogen, carboxy, NR6R7, alkyl and a mono- or bicyclic aromatic or heteroaromatic ring, wherein each alkyl might be unsubstituted or substituted with one or more residues, which are preferably selected from among hydroxyl, alkoxy, fluoro, NR6R7, and carboxy, and wherein each mono- or bicyclic aromatic or heteroaromatic ring can be unsubstituted or substituted with one or more residues, which are preferably selected from among alkyl, hydroxyl, alkoxy, alkylthio, alkylcarbonyl, alkylaminocarbonyl, alkoxycarbonyl, carboxyalkoxy, alkoxycarbonylalkoxy, halogen, carboxy, carbamoyl, sulfamoyl, alkylaminosulfonyl, alkylsulfonyl, sulfo, alkylsulfinyl, NR6R7, cyano and nitro, wherein two of these residues might form a 5-7 membered non-aromatic ring.

R16 and R17 are independently selected from among hydrogen, C1-C8 alkyl, phenyl, thienyl, pyridyl, C1-C8 alkylsulfonyl, phenylsulfonyl, thienylsulfonyl, pyridylsulfonyl, C1-C8 alkylcarbonyl, C1-C8 alkoxycarbonyl, aminocarbonyl, C1-C8 alkylaminocarbonyl, thienylcarbonyl, pyridylcarbonyl, and phenylcarbonyl and wherein R16 and R17 might form a 5-7 membered cycle.

Also preferred are compounds according to formula II, wherein
  the dotted bond represents a single or a double bond; and wherein
  R1 and R2 are selected from hydrogen, halogen, hydroxyl, carboxy, carbamoyl, sulfamoyl, cyano, nitro, NR6R7, C1-C6 alkyl, C1-C6 alkoxy, C1-C6 alkylcarbonyl, C1-C6 alkoxycarbonyl, C1-C6 alkylcarbonylamino, C1-C6 alkylaminocarbonyl, phenylsulfonylaminomethyl, thienylsulfonylaminomethyl and C1-C6 alkylaminosulfonyl, wherein each alkyl might be unsubstituted or substituted with one or more residues preferably selected from among hydroxyl, C1-C6 alkoxy, fluoro, and NR6R7; and wherein each phenyl or thienyl might be unsubstituted or substituted with one or more residues preferably selected from among hydroxyl, C1-C6 alkoxy, halogen, C1-C6 alkyl, carboxy, NR6R7, cyano and nitro, provided that if R1 is different from hydroxyl or hydroxymethyl, then R2 must represent hydroxyl or hydroxymethyl;
  R3 is selected from hydrogen, halogen, hydroxyl, carboxy, carbamoyl, sulfamoyl, cyano, nitro, NR6R7, C1-C6 alkyl, C1-C6 alkoxy, C1-C6 alkylcarbonyl, and C1-C6 alkoxycarbonyl, wherein each alkyl might be unsubstituted or substituted with one or more residues preferably selected from among hydroxyl, C1-C6 alkoxy, fluoro, and NR6R7;

R4 is hydrogen, C1-C3 alkylcarbonyl, or C1-C3 alkyl;

R5 is selected from hydrogen, C1-C3 alkyl, which might be unsubstituted or substituted with one or more residues preferably selected from among hydroxyl, C1-C3 alkoxy, fluoro, and NR6R7;

R6 and R7 are independently selected from hydrogen, C1-C8 alkyl, phenyl, C1-C8 alkylsulfonyl, phenylsulfonyl, thienylsulfonyl, C1-C8 alkylcarbonyl, C1-C6 alkoxycarbonyl, aminocarbonyl, C1-C8 alkylaminocarbonyl, phenylcarbonyl, and thienylcarbonyl; wherein each alkyl might be unsubstituted or substituted with one or more residues preferably selected from among hydroxyl, C1-C6 alkoxy, phenyl, fluoro, carboxy, and NR16R17; and wherein R6 and R7 might form a 5-7 membered cycle; and wherein each phenyl or thienyl might be unsubstituted or substituted with one or more residues preferably selected from among hydroxyl, C1-C6 alkoxy, halogen, C1-C6 alkyl, carboxy, NR16R17, cyano and nitro;

R8 is selected from hydrogen, methyl, hydroxyl, and methoxy;

R9 and R10 are independently selected from hydrogen, carboxy, NR6R7, C1-C6 alkyl and a mono- or bicyclic aromatic or heteroaromatic ring selected from phenyl, furanyl, thienyl, pyrollyl, thiazolyl, oxazolyl, imidazolyl, pyrazolyl, isoxazolyl, isothiazolyl, triazolyl, oxydiazolyl, thiadiazolyl, pyranyl, pyridinyl, pyridazinyl, pyrimidinyl, pyrazinyl, triazinyl and tetrazinyl, quinolinyl, quinoxalinyl, indolyl, benzofuranyl, benzothienyl, benzooxazolyl, benzothiazolyl and naphthalyl;

wherein each alkyl might be unsubstituted or substituted with one or more residues preferably selected from among hydroxyl, C1-C6 alkoxy, fluoro, NR6R7, and carboxy;

and wherein each mono- or bicyclic aromatic or heteroaromatic ring can be unsubstituted or substituted with one or more residues preferably selected from among C1-C6 alkyl, hydroxyl, C1-C4 alkoxy, C1-C4 alkylthio, C1-C4 alkylcarbonyl, C1-C6 alkylaminocarbonyl, C1-C4 alkoxycarbonyl, carboxy(C1-C4)alkoxy, C1-C4 alkoxycarbonyl(C1-C4)alkoxy, halogen, carboxy, carbamoyl, sulfamoyl, C1-C4 alkylaminosulfonyl, C1-C4 alkylsulfonyl, sulfo, C1-C4 alkylsulfinyl, NR6R7, cyano and nitro; wherein two of these residues might form a 5-7 membered non-aromatic ring.

R16 and R17 are independently selected from among hydrogen, C1-C6 alkyl, phenyl, C1-C6 alkylsulfonyl, phenylsulfonyl, thienylsulfonyl, C1-C6 alkylcarbonyl, C1-C6 alkoxycarbonyl, aminocarbonyl, C1-C6 alkylaminocarbonyl, phenylcarbonyl, and thienylcarbonyl wherein R16 and R17 might form a 5-7 membered cycle.

Especially preferred are compounds according to the present invention, wherein
  R9 is hydrogen, NR6R7, C1-C3 alkyl, phenyl, thiophen-2-yl, pyridinyl, wherein each alkyl may be unsubstituted or substituted with one or more residues selected from among hydroxyl, C1-C4 alkoxy, NR6R7, and carboxy; and wherein each monocyclic aromatic or heteroaromatic ring can be unsubstituted or substituted with one or more residues selected from among C1-C3 alkyl, hydroxyl, C1-C4 alkoxy, C1-C4 alkoxycarbonyl, carboxymethoxy, C0-C2 alkoxycarbonyl(C1-C2)alkoxy, preferably 2-alkoxy-2-oxoethoxy, fluoro, chloro, bromo, carboxy, NR6R7, cyano and nitro; and R10 is hydrogen or C1-C3 alkyl, wherein the C1-C3 alkyl may be unsubstituted or substituted with one or more residues selected from among hydroxyl, methoxy, or fluoro;

and the dotted bond represents a double bond.

Another especially preferred embodiment of the present invention are compounds according to formula II, wherein R9 is hydrogen or C1-C3 alkyl, wherein the C1-C3 alkyl may be unsubstituted or substituted with one or more residues selected from among hydroxyl, methoxy, or fluoro;
and R10 is hydrogen, NR6R7, C1-C3 alkyl, phenyl, thiophen-2-yl, pyridinyl, wherein each alkyl may be unsubstituted or substituted with one or more residues selected from among hydroxyl, C1-C4 alkoxy, NR6R7, and carboxy; and wherein each monocyclic aromatic or heteroaromatic ring can be unsubstituted or substituted with one or more residues selected from among C1-C3 alkyl, hydroxyl, C1-C4 alkoxy, C1-C4 alkoxycarbonyl, carboxymethoxy, C0-C2 alkoxycarbonyl(C1-C2)alkoxy, preferably 2-alkoxy-2-oxoethoxy, fluoro, chloro, bromo, carboxy, NR6R7, cyano and nitro and the dotted bond represents a double bond.

Especially preferred are compounds according to formula II, wherein
the dotted bond represents a single or a double bond; and wherein R1 and R2 are selected from hydrogen, halogen, hydroxyl, carboxy, carbamoyl, cyano, nitro, sulfamoyl, NR6R7, C1-C3 alkyl, C1-C3 alkoxy, C1-C3 alkylcarbonyl, C1-C3 alkoxycarbonyl, C1-C4 alkylaminocarbonyl, morpholinocarbonyl, 2-thienylsulfonylaminomethyl, wherein each alkyl might be unsubstituted or substituted with one or more residues preferably selected from among hydroxyl, C1-C3 alkoxy, fluoro, and NR6R7; and wherein the thienyl can be unsubstituted or substituted with one or more residues preferably selected from among hydroxyl, C1-C3 alkoxy, halogen, C1-C3 alkyl, carboxy, NR6R7 and cyano, provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, C1-C3 alkyl, C1-C3 alkoxy, C1-C3 alkylcarbonyl, and C1-C3 alkoxycarbonyl, wherein each alkyl might be unsubstituted or substituted with one or more residues preferably selected from among hydroxyl, C1-C3 alkoxy, fluoro, and NR6R7;

R4 is hydrogen or methyl;

R5 is selected from hydrogen and methyl, wherein methyl might be unsubstituted or substituted with one or more residues selected from among hydroxyl, methoxy, ethoxy, fluoro, and NR6R7;

R6 and R7 are independently selected from hydrogen, C1-C3 alkyl, C1-C8 alkylsulfonyl, 2-thienylsulfonyl, C1-C8 alkylcarbonyl, C1-C4 alkoxycarbonyl, aminocarbonyl, and C1-C8 alkylaminocarbonyl; wherein each alkyl might be unsubstituted or substituted with one or more residues preferably selected from among hydroxyl, C1-C3 alkoxy, carboxy, and NR16R17; and wherein R6 and R7 might form a 5-7 membered cycle; and wherein the thienyl might be unsubstituted or substituted with one or more residues selected from among hydroxyl, C1-C3 alkoxy, halogen, C1-C3 alkyl, carboxy, NR16R17 and cyano;

R8 is selected from hydrogen and methyl;

R9 and R10 are independently selected from hydrogen, NR6R7, C1-C6 alkyl, phenyl, thienyl, furanyl, pyridinyl, wherein each alkyl might be unsubstituted or substituted with one or more residues preferably selected from among hydroxyl, C1-C3 alkoxy, fluoro, NR6R7, and carboxy; and wherein each monocyclic aromatic or heteroaromatic ring can be unsubstituted or substituted with one or more residues preferably selected from among C1-C3 alkyl, hydroxyl, C1-C4 alkoxy, C1-C4 alkoxycarbonyl, C1-C4 alkylaminocarbonyl, carboxy (C1-C2)alkoxy, C1-C3 alkoxycarbonyl(C1-C2)alkoxy preferably 2-alkoxy-2-oxoethoxy, halogen, carboxy, NR6R7 and cyano; wherein two of these residues might form a 5-7 membered non-aromatic ring;

R16 and R17 are independently selected from among hydrogen, C1-C3 alkyl, C1-C4 alkylsulfonyl, 2-thienylsulfonyl, C1-C4 alkylcarbonyl, C1-C4 alkoxycarbonyl, aminocarbonyl, and C1-C4 alkylaminocarbonyl wherein R16 and R17 might form a 5-7 membered cycle.

Another especially preferred embodiment of the present invention are compounds according to formula II, wherein
the dotted bond represents a single or a double bond; and wherein R1 is selected from hydrogen, halogen, hydroxyl, hydroxymethyl, methoxycarbonyl, ethoxycarbonyl, methyl, ethyl, carboxy, and methoxymethyl;

R2 is selected from hydrogen, hydroxyl, methoxycarbonyl, carboxy, and hydroxymethyl;

R3 is selected from hydrogen, halogen, methyl, ethyl, methoxycarbonyl, ethoxycarbonyl, carboxy, hydroxymethyl;

R4 is hydrogen or methyl;

R5 is hydrogen or methyl;

R8 is hydrogen or methyl;

R9 is hydrogen, methyl, unsubstituted phenyl, halophenyl, preferably para-fluorophenyl, or thienyl;

R10 is hydrogen, methyl, unsubstituted phenyl, or halophenyl;

Another preferred embodiment of the present invention are compounds according to formula I and the pharmaceutically acceptable salt or solvate thereof, in the form of a racemate or as a substantially pure enantiomer or diastereomer or mixtures of the optical isomers, having the formula III

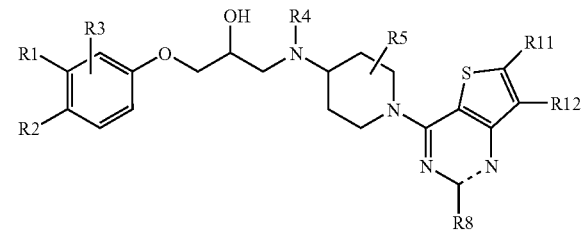

formula III wherein R1, R2, R3, R4, R5, R8, R11 and R12 are defined as above for formula I.

Also preferred are compounds according to formula III, wherein
one of R11 and R12 is hydrogen, carboxy, NR6R7, C1-C6 alkyl and a mono- or bicyclic aromatic or heteroaromatic ring selected from phenyl, furanyl, thiophenyl, pyrollyl, thiazolyl, oxazolyl, imidazolyl, pyrazolyl, isoxazolyl, isothiazolyl, triazolyl, oxydiazolyl, thiadiazolyl, pyranyl, pyridinyl, pyridazinyl, pyrimidinyl, pyrazinyl, triazinyl and tetrazinyl, or a bicyclic aromatic or heteroaromatic ring selected from quinolinyl, quinoxalinyl, indolyl, benzofuranyl, benzothiophenyl, benzooxazolyl, benzothiazolyl and naphthalyl; wherein each alkyl may be unsubstituted or substituted with one or more residues selected from among hydroxyl, C1-C6 alkoxy, fluoro, NR6R7, and carboxy; and wherein each mono- or bicyclic aromatic or heteroaromatic ring can be unsubstituted or substituted with one or more residues selected from among C1-C6 alkyl, hydroxyl, C1-C4 alkoxy, C1-C4 alkylthio, C1-C4 alkylcarbonyl, C1-C6 alkylaminocarbonyl, di(C1-C6)alkylaminocarbonyl, C1-C4 alkoxycarbonyl, carboxymethoxy, C1-C4 alkoxycarbonyl(C1-C4)alkoxy, halogen, carboxy, carbamoyl, sulfamoyl, C1-C4 alkylaminosulfonyl, di(C1-C4)alkylaminosulfonyl, C1-C4 alkylsulfonyl, sulfo, C1-C4 alkylsulfinyl, NR6R7, cyano and nitro; wherein two of these residues selected from R11 and R12 might form a 5-7 membered non-aromatic ring;

and the other one of R11 and R12 is hydrogen or C1-C6 alkyl; wherein the C1-C6 alkyl may be unsubstituted or substituted with one or more residues selected from among hydroxyl, C1-C3 alkoxy, or fluoro.

Another preferred embodiment of the present invention are compounds according to formula III, wherein the dotted bond represents a single or a double bond; and wherein R1 and R2 are selected from hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, provided that if R1 is different from hydroxyl or hydroxymethyl, then R2 must represent hydroxyl or hydroxymethyl;

In another embodiment of the invention, R1 and R2 are selected from hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, wherein each alkyl, may be unsubstituted or substituted with one or more residues, which are preferably selected from among hydroxyl, alkoxy, fluoro, and NR6R7; and wherein each aryl or heteroaryl is a monocyclic aromatic or heteroaromatic ring, respectively, which can be unsubstituted or substituted with one or more residues, which are preferably selected from among hydroxyl, alkoxy, halogen, alkyl, carboxy, NR6R7, cyano and nitro; provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, alkyl, alkoxy, alkylcarbonyl, and alkoxycarbonyl;

In another embodiment of the invention, R3 is selected from hydrogen, halogen, hydroxyl, carboxy, carbamoyl, sulfamoyl, cyano, nitro, NR6R7, alkyl, alkoxy, alkylcarbonyl, and alkoxycarbonyl, wherein each alkyl, might be unsubstituted or substituted with one or more residues, which are preferably selected from among hydroxyl, alkoxy, fluoro, and NR6R7;

R4 is hydrogen, alkylcarbonyl, or alkyl;

R5 is selected from hydrogen, alkyl, wherein alkyl might be unsubstituted or substituted with one or more residues, which are preferably selected from among hydroxyl, alkoxy, fluoro, and NR6R7;

R6 and R7 are independently selected from hydrogen, alkyl, aryl, alkylsulfonyl, arylsulfonyl, heteroarylsulfonyl, alkylcarbonyl, alkoxycarbonyl, aminocarbonyl, alkylaminocarbonyl, arylcarbonyl, and heteroarylcarbonyl; wherein each alkyl might be unsubstituted or substituted with one or more residues, which are preferably selected from among hydroxyl, alkoxy, phenyl, fluoro, carboxy, and NR16R17; and wherein R6 and R7 might form a 5-7 membered cycle; and wherein each aryl or heteroaryl is a monocyclic aromatic or heteroaromatic ring, respectively, which can be unsubstituted or substituted with one or more residues, which are preferably selected from among hydroxyl, alkoxy, halogen, alkyl, carboxy, NR16R17, cyano and nitro;

R8 is selected from among hydrogen, alkyl, hydroxyl, alkoxy;

R11 and R12 are independently selected from hydrogen, carboxy, NR6R7, alkyl and a mono- or bicyclic aromatic or heteroaromatic ring, In another embodiment of the invention, R11 and R12 are independently selected from hydrogen, carboxy, NR6R7, alkyl and a mono- or bicyclic aromatic or heteroaromatic ring, wherein each alkyl might be unsubstituted or substituted with one or more residues, which are preferably selected from among hydroxyl, alkoxy, fluoro, NR6R7, and carboxy, and wherein each mono- or bicyclic aromatic or heteroaromatic ring can be unsubstituted or substituted with one or more residues, which are preferably selected from among alkyl, hydroxyl, alkoxy, alkylthio, alkylcarbonyl, alkylaminocarbonyl, alkoxycarbonyl, carboxyalkoxy, alkoxycarbonylalkoxy, halogen, carboxy, carbamoyl, sulfamoyl, alkylaminosulfonyl, alkylsulfonyl, sulfo, alkylsulfinyl, NR6R7, cyano and nitro, wherein two of these residues might form a 5-7 membered non-aromatic ring.

R16 and R17 are independently selected from among hydrogen, C1-C8 alkyl, phenyl, thienyl, pyridyl, C1-C8 alkylsulfonyl, phenylsulfonyl, thienylsulfonyl, pyridylsulfonyl, C1-C8 alkylcarbonyl, C1-C8 alkoxycarbonyl, aminocarbonyl, C1-C8 alkylaminocarbonyl, thienylcarbonyl, pyridylcarbonyl, and phenylcarbonyl and wherein R16 and R17 might form a 5-7 membered cycle.

Also preferred are compounds according to formula III, wherein the dotted bond represents a single or a double bond; and wherein R1 and R2 are selected from hydrogen, halogen, hydroxyl, carboxy, carbamoyl, sulfamoyl, cyano, nitro, NR6R7, C1-C6 alkyl C1-C6 alkoxy, C1-C6 alkylcarbonyl, C1-C6 alkoxycarbonyl, C1-C6 alkylcarbonylamino, C1-C6 alkylaminocarbonyl, phenylsulfonylaminomethyl, thienylsulfonylaminomethyl and C1-C6 alkylaminosulfonyl, wherein each alkyl might be unsubstituted or substituted with one or more residues preferably selected from among hydroxyl, C1-C6 alkoxy, fluoro, and NR6R7; and wherein each phenyl or thienyl might be unsubstituted or substituted with one or more residues preferably selected from among hydroxyl, C1-C6 alkoxy, halogen, C1-C6 alkyl, carboxy, NR6R7, cyano and nitro, provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, C1-C6 alkyl, C1-C6 alkoxy, C1-C6 alkylcarbonyl, and C1-C6 alkoxycarbonyl, wherein each alkyl might be unsubstituted or substituted with one or more residues preferably selected from among hydroxyl, C1-C6 alkoxy, fluoro, and NR6R7;

R4 is hydrogen, C1-C3 alkylcarbonyl, or C1-C3 alkyl;

R5 is selected from hydrogen, C1-C3 alkyl, which might be unsubstituted or substituted with one or more residues preferably selected from among hydroxyl, C1-C3 alkoxy, fluoro, and NR6R7;

R6 and R7 are independently selected from hydrogen, C1-C8 alkyl, phenyl, C1-C8 alkylsulfonyl, phenylsulfonyl, thienylsulfonyl, C1-C8 alkylcarbonyl, C1-C6 alkoxycarbonyl, aminocarbonyl, C1-C8 alkylaminocarbonyl, phenylcarbonyl, and thienylcarbonyl; wherein each alkyl might be unsubstituted or substituted with one or more residues preferably selected from among hydroxyl, C1-C6 alkoxy, phenyl, fluoro, carboxy, and NR16R17; and wherein R6 and R7 might form a 5-7 membered cycle; and wherein each phenyl or thienyl might be unsubstituted or substituted with one or more residues preferably selected from among hydroxyl, C1-C6 alkoxy, halogen, C1-C6 alkyl, carboxy, NR16R17, cyano and nitro;

R8 is selected from hydrogen, methyl, hydroxyl, and methoxy;

R11 and R12 are independently selected from hydrogen, carboxy, NR6R7, C1-C6 alkyl and a mono- or bicyclic aromatic or heteroaromatic ring selected from phenyl, furanyl, thienyl, pyrollyl, thiazolyl, oxazolyl, imidazolyl, pyrazolyl, isoxazolyl, isothiazolyl, triazolyl, oxydiazolyl, thiadiazolyl, pyranyl, pyridinyl, pyridazinyl, pyrimidinyl, pyrazinyl, triazinyl and tetrazinyl, quinolinyl, quinoxalinyl, indolyl, benzofuranyl, benzothienyl, benzooxazolyl, benzothiazolyl and naphthalyl;

wherein each alkyl might be unsubstituted or substituted with one or more residues preferably selected from among hydroxyl, C1-C6 alkoxy, fluoro, NR6R7, and carboxy;

and wherein each mono- or bicyclic aromatic or heteroaromatic ring can be unsubstituted or substituted with one or more residues preferably selected from among C1-C6 alkyl, hydroxyl, C1-C4 alkoxy, C1-C4 alkylthio, C1-C4 alkylcarbonyl, C1-C6 alkylaminocarbonyl, C1-C4 alkoxycarbonyl, carboxy(C1-C4)alkoxy, C1-C4 alkoxycarbonyl(C1-C4)alkoxy, halogen, carboxy, carbamoyl, sulfamoyl, C1-C4 alkylaminosulfonyl, C1-C4 alkylsulfonyl, sulfo, C1-C4 alkylsulfinyl, NR6R7, cyano and nitro; wherein two of these residues might form a 5-7 membered non-aromatic ring.

R16 and R17 are independently selected from among hydrogen, C1-C6 alkyl, phenyl, C1-C8 alkylsulfonyl, phenylsulfonyl, thienylsulfonyl, C1-C6 alkylcarbonyl, C1-C6 alkoxycarbonyl, aminocarbonyl, C1-C6 alkylaminocarbonyl, phenylcarbonyl, and thienylcarbonyl wherein R16 and R17 might form a 5-7 membered cycle.

An especially preferred embodiment of the present invention are compounds according to formula III, wherein
one of R11 and R12 is hydrogen, NR6R7, C1-C3 alkyl, phenyl, thiophen-2-yl, wherein alkyl may be unsubstituted or substituted with one or more residues selected from among C1-C4 alkoxy, NR6R7, and carboxy; and wherein the phenyl or thiophen-2-yl may be unsubstituted or substituted with one or more residues selected from among C1-C3 alkyl, hydroxyl, C1-C4 alkoxy, C1-C4 alkoxycarbonyl, carboxymethoxy, C0-C2 alkoxycarbonyl(C1-C2)alkoxy, preferably 2-alkoxy-2-oxoethoxy, fluoro, chloro, bromo, carboxy, NR6R7, cyano and nitro; wherein two of these residues may form a 5-7 membered non-aromatic ring the other one of R11 and R12 is hydrogen or C1-C3 alkyl, wherein the C1-C3 alkyl may be unsubstituted or substituted with one or more residues selected from among hydroxyl, methoxy, or fluoro;

and the dotted bond represents a double bond.

Also especially preferred are compounds according to formula III, wherein
the dotted bond represents a single or a double bond; and wherein R1 and R2 are selected from hydrogen, halogen, hydroxyl, carboxy, carbamoyl, cyano, nitro, sulfamoyl, NR6R7, C1-C3 alkyl, C1-C3 alkoxy, C1-C3 alkylcarbonyl, C1-C3 alkoxycarbonyl, C1-C4 alkylaminocarbonyl, morpholinocarbonyl, 2-thienylsulfonylaminomethyl, wherein each alkyl might be unsubstituted or substituted with one or more residues preferably selected from among hydroxyl, C1-C3 alkoxy, fluoro, and NR6R7; and wherein the thienyl can be unsubstituted or substituted with one or more residues preferably selected from among hydroxyl, C1-C3 alkoxy, halogen, C1-C3 alkyl, carboxy, NR6R7 and cyano, provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, C1-C3 alkyl, C1-C3 alkoxy, C1-C8 alkylcarbonyl, and C1-C3 alkoxycarbonyl, wherein each alkyl might be unsubstituted or substituted with one or more residues preferably selected from among hydroxyl, C1-C3 alkoxy, fluoro, and NR6R7;

R4 is hydrogen or methyl;

R5 is selected from hydrogen and methyl, wherein methyl might be unsubstituted or substituted with one or more residues selected from among hydroxyl, methoxy, ethoxy, fluoro, and NR6R7;

R6 and R7 are independently selected from hydrogen, C1-C3 alkyl, C1-C8 alkylsulfonyl, 2-thienylsulfonyl, C1-C8 alkylcarbonyl, C1-C4 alkoxycarbonyl, aminocarbonyl, and C1-C8 alkylaminocarbonyl; wherein each alkyl might be unsubstituted or substituted with one or more residues preferably selected from among hydroxyl, C1-C3 alkoxy, carboxy, and NR16R17; and wherein R6 and R7 might form a 5-7 membered cycle; and wherein the thienyl might be unsubstituted or substituted with one or more residues selected from among hydroxyl, C1-C3 alkoxy, halogen, C1-C3 alkyl, carboxy, NR16R17 and cyano;

R8 is selected from hydrogen and methyl;

R11 and R12 are independently selected from hydrogen, NR6R7, C1-C6 alkyl, phenyl, thienyl, furanyl, pyridinyl, wherein each alkyl might be unsubstituted or substituted with one or more residues preferably selected from among hydroxyl, C1-C3 alkoxy, fluoro, NR6R7, and carboxy; and wherein each monocyclic aromatic or heteroaromatic ring can be unsubstituted or substituted with one or more residues preferably selected from among C1-C3 alkyl, hydroxyl, C1-C4 alkoxy, C1-C4 alkoxycarbonyl, C1-C4 alkylaminocarbonyl, carboxy (C1-C2)alkoxy, C1-C3 alkoxycarbonyl(C1-C2)alkoxy preferably 2-alkoxy-2-oxoethoxy, halogen, carboxy, NR6R7 and cyano; wherein two of these residues might form a 5-7 membered non-aromatic ring;

R16 and R17 are independently selected from among hydrogen, C1-C3 alkyl, C1-C4 alkylsulfonyl, 2-thienylsulfonyl, C1-C4 alkylcarbonyl, C1-C4 alkoxycarbonyl, aminocarbonyl, and C1-C4 alkylaminocarbonyl wherein R16 and R17 might form a 5-7 membered cycle.

Another especially preferred embodiment of the present invention are compounds according to formula III, wherein the dotted bond represents a single or a double bond; and wherein R1 is selected from hydrogen, halogen, hydroxyl, hydroxymethyl, methoxycarbonyl, ethoxycarbonyl, methyl, ethyl, carboxy, and methoxymethyl;

R2 is selected from hydrogen, hydroxyl, methoxycarbonyl, carboxy, and hydroxymethyl;

R3 is selected from hydrogen, halogen, methyl, ethyl, methoxycarbonyl, ethoxycarbonyl, carboxy, hydroxymethyl;

R4 is hydrogen or methyl;

R5 is hydrogen or methyl

R8 is hydrogen or methyl;

R11 is hydrogen, methyl, unsubstituted phenyl, halophenyl, preferably para-fluorophenyl, or thienyl;

R12 is hydrogen, methyl, unsubstituted phenyl, or halophenyl;

According to the present invention especially preferred is a compound according to formula I, or the pharmaceutically acceptable salts or solvates thereof, in the form of a racemate or as a substantially pure enantiomer or diastereomer or mixtures of the optical isomers, and having the formula IV

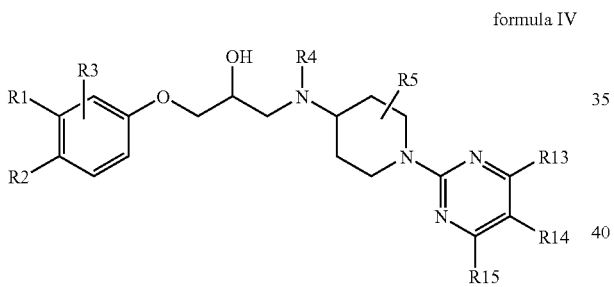

formula IV wherein R1, R2, R3, R4, R5, R13, R14 and R15 are defined as above for formula I.

Especially preferred are compounds according to the present invention according to formula IV, wherein R13, R14 and R15 are selected from hydrogen and C1-C3 alkyl, which may be unsubstituted or substituted with one or more residues selected from among hydroxyl, methoxy, ethoxy or NR6R7.

Another preferred embodiment of the present invention encompass compounds of formula IV, wherein R1 and R2 are selected from hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, provided that if R1 is different from hydroxyl or hydroxymethyl, then R2 must represent hydroxyl or hydroxymethyl;

In another embodiment of the invention, R1 and R2 are selected from hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, wherein each alkyl, may be unsubstituted or substituted with one or more residues, which are preferably selected from among hydroxyl, alkoxy, fluoro, and NR6R7; and wherein each aryl or heteroaryl is a monocyclic aromatic or heteroaromatic ring, respectively, which can be unsubstituted or substituted with one or more residues, which are preferably selected from among hydroxyl, alkoxy, halogen, alkyl, carboxy, NR6R7 cyano and nitro; provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, alkyl, alkoxy, alkylcarbonyl, and alkoxycarbonyl;

In another embodiment of the invention, R3 is selected from hydrogen, halogen, hydroxyl, carboxy, carbamoyl, sulfamoyl, cyano, nitro, NR6R7, alkyl, alkoxy, alkylcarbonyl, and alkoxycarbonyl, wherein each alkyl, might be unsubstituted or substituted with one or more residues, which are preferably selected from among hydroxyl, alkoxy, fluoro, and NR6R7;

R4 is hydrogen, alkylcarbonyl, or alkyl;

R5 is selected from hydrogen, alkyl, wherein alkyl might be unsubstituted or substituted with one or more residues, which are preferably selected from among hydroxyl, alkoxy, fluoro, and NR6R7;

R6 and R7 are independently selected from hydrogen, alkyl, aryl, alkylsulfonyl, arylsulfonyl, heteroarylsulfonyl, alkylcarbonyl, alkoxycarbonyl, aminocarbonyl, alkylaminocarbonyl, arylcarbonyl, and heteroarylcarbonyl; wherein each alkyl might be unsubstituted or substituted with one or more residues, which are preferably selected from among hydroxyl, alkoxy, phenyl, fluoro, carboxy, and NR16R17; and wherein R6 and R7 might form a 5-7 membered cycle; and wherein each aryl or heteroaryl is a monocyclic aromatic or heteroaromatic ring, respectively, which can be unsubstituted or substituted with one or more residues, which are preferably selected from among hydroxyl, alkoxy, halogen, alkyl, carboxy, NR16R17, cyano and nitro;

R13, R14 and R11 are independently selected from hydrogen, alkyl, haloalkyl, carboxy, NR6R7, aryl, heteroaryl, hydroxyl, alkoxy, alkoxycarbonyl, arylaminocarbonyl, heteroarylaminocarbonyl, halogen and nitro, wherein each alkyl might be unsubstituted or substituted with one or more residues, which are preferably selected from among hydroxyl, alkoxy, fluoro and aryl; and wherein two of these residues (selected from R13, R14, R15) might form a 5-7 membered non-aromatic or aromatic ring and wherein each aryl or heteroaryl is a monocyclic aromatic or heteroaromatic ring, respectively, which can be unsubstituted or substituted with one or more residues, which are preferably selected from among hydroxyl, alkoxy, halogen, carboxy, alkoxycarbonyl, NR6R7, cyano and nitro; wherein two of these residues might form a 5-7 membered non-aromatic ring.

R16 and R17 are independently selected from among hydrogen, C1-C8 alkyl, phenyl, thienyl, pyridyl, C1-C8 alkylsulfonyl, phenylsulfonyl, thienylsulfonyl, pyridylsulfonyl, C1-C8 alkylcarbonyl, C1-C8 alkoxycarbonyl, aminocarbonyl, C1-C8 alkylaminocarbonyl, thienylcarbonyl, pyridylcarbonyl, and phenylcarbonyl and wherein R16 and R17 might form a 5-7 membered cycle.

According to the present invention compounds are also preferred according to formula IV, wherein R1 and R2 are selected from hydrogen, halogen, hydroxyl, carboxy, carbamoyl, sulfamoyl, cyano, nitro, NR6R7, C1-C6 alkyl, C1-C6 alkoxy, C1-C6 alkylcarbonyl, C1-C6 alkoxycarbonyl, C1-C6 alkylcarbonylamino, C1-C6 alkylaminocarbonyl, phenylsulfonylaminomethyl, thienylsulfonylaminomethyl and C1-C6 alkylaminosulfonyl, wherein each alkyl might be unsubstituted or substituted with one or more residues preferably selected from among hydroxyl, C1-C6 alkoxy, fluoro, and NR6R7; and wherein each phenyl or thienyl might be unsubstituted or substituted with one or more residues preferably selected from among hydroxyl, C1-C6 alkoxy, halogen, C1-C6 alkyl, carboxy, NR6R7, cyano and nitro, provided that if R1 is different from hydroxyl or hydroxymethyl, then is R2 must represent hydroxyl or hydroxymethyl;

R3 is selected from hydrogen, halogen, hydroxyl, carboxy, carbamoyl, sulfamoyl, cyano, nitro, NR6R7, C1-C6 alkyl, C1-C6 alkoxy, C1-C6 alkylcarbonyl, and C1-C6 alkoxycarbonyl, wherein each alkyl might be unsubstituted or substituted with one or more residues preferably selected from among hydroxyl, C1-C6 alkoxy, fluoro, and NR6R7;

R4 is hydrogen, C1-C3 alkylcarbonyl, or C1-C3 alkyl;

R5 is selected from hydrogen, C1-C3 alkyl, which might be unsubstituted or substituted with one or more residues preferably selected from among hydroxyl, C1-C3 alkoxy, fluoro, and NR6R7;

R6 and R7 are independently selected from hydrogen, C1-C8 alkyl, phenyl, C1-C8 alkylsulfonyl, phenylsulfonyl, thienylsulfonyl, C1-C8 alkylcarbonyl, C1-C6 alkoxycarbonyl, aminocarbonyl, C1-C8 alkylaminocarbonyl, phenylcarbonyl, and thienylcarbonyl; wherein each alkyl might be unsubstituted or substituted with one or more residues preferably selected from among hydroxyl, C1-C6 alkoxy, phenyl, fluoro, carboxy, and NR16R17; and wherein R6 and R7 might form a 5-7 membered cycle; and wherein each phenyl or thienyl might be unsubstituted or substituted with one or more residues preferably selected from among hydroxyl, C1-C6 alkoxy, halogen, C1-C6 alkyl, carboxy, NR16R17, cyano and nitro;

R13, R14 and R15 are independently selected from hydrogen, C1-C4 alkyl, C1-C3 haloalkyl, carboxy, NR6R7, phenyl, hydroxyl, C1-C4 alkoxy, C1-C4 alkoxycarbonyl, phenylaminocarbonyl, thienylaminocarbonyl, halogen and nitro, wherein each alkyl might be unsubstituted or substituted with one or more residues preferably selected from among hydroxyl, C1-C4 alkoxy, fluoro and phenyl; wherein two of these residues selected from R13, R14 and R15 might form a 5-7 membered non-aromatic or aromatic ring;

and wherein phenyl or thienyl can be unsubstituted or substituted with one or more residues preferably selected from among hydroxyl, C1-C4 alkoxy, halogen, carboxy, C1-C4 alkoxycarbonyl, NR6R7, cyano and nitro; wherein two of these residues might form a 5-7 membered non-aromatic ring.

R16 and R17 are independently selected from among hydrogen, C1-C6 alkyl, phenyl, C1-C6 alkylsulfonyl, phenylsulfonyl, thienylsulfonyl, C1-C6 alkylcarbonyl, C1-C6 alkoxycarbonyl, aminocarbonyl, C1-C6 alkylaminocarbonyl, phenylcarbonyl, and thienylcarbonyl wherein R16 and R17 might form a 5-7 membered cycle.

Especially preferred are compounds according to formula IV, wherein

R1 and R2 are selected from hydrogen, halogen, hydroxyl, carboxy, carbamoyl, cyano, nitro, sulfamoyl, NR6R7, C1-C3 alkyl, C1-C3 alkoxy, C1-C3 alkylcarbonyl, C1-C3 alkoxycarbonyl, C1-C4 alkylaminocarbonyl, morpholinocarbonyl, 2-thienylsulfonylaminomethyl, wherein each alkyl might be unsubstituted or substituted with one or more residues preferably selected from among hydroxyl, C1-C3 alkoxy, fluoro, and NR6R7; and wherein the thienyl can be unsubstituted or substituted with one or more residues preferably selected from among hydroxyl, C1-C3 alkoxy, halogen, C1-C3 alkyl, carboxy, NR6R7 and cyano, provided that if R1 is different from hydroxyl or hydroxymethyl, then R2 must represent hydroxyl or hydroxymethyl;

R3 is selected from hydrogen, halogen, hydroxyl, carboxy, carbamoyl, sulfamoyl, cyano, nitro, NR6R7, C1-C3 alkyl, C1-C3 alkoxy, C1-C3 alkylcarbonyl, and C1-C3 alkoxycarbonyl, wherein each alkyl might be unsubstituted or substituted with one or more residues preferably selected from among hydroxyl, C1-C3 alkoxy, fluoro, and NR6R7;

R4 is hydrogen or methyl;

R5 is selected from hydrogen and methyl, wherein methyl might be unsubstituted or substituted with one or more residues selected from among hydroxyl, methoxy, ethoxy, fluoro, and NR6R7;

R6 and R7 are independently selected from hydrogen, C1-C3 alkyl, C1-C8 alkylsulfonyl, 2-thienylsulfonyl, C1-C8 alkylcarbonyl, C1-C4 alkoxycarbonyl, aminocarbonyl, and C1-C8 alkylaminocarbonyl; wherein each alkyl might be unsubstituted or substituted with one or more residues preferably selected from among hydroxyl, C1-C3 alkoxy, carboxy, and NR16R17; and wherein R6 and R7 might form a 5-7 membered cycle; and wherein the thienyl might be unsubstituted or substituted with one or more residues selected from among hydroxyl, C1-C3 alkoxy, halogen, C1-C3 alkyl, carboxy, NR16R17 and cyano;

R13, R14 and R15 are independently selected from hydrogen, C1-C3 alkyl, CF3, carboxy, NR6R7, phenyl, hydroxyl, C1-C3 alkoxy, C1-C3 alkoxycarbonyl, phenylaminocarbonyl, halogen and nitro, wherein each alkyl might be unsubstituted or substituted with one or more residues preferably selected from among hydroxyl, C1-C3 alkoxy, fluoro and phenyl;

and wherein phenyl can be unsubstituted or substituted with one or more residues preferably selected from among hydroxyl, C1-C3 alkoxy, halogen, carboxy, C1-C3 alkoxycarbonyl, NR6R7 and cyano; wherein two of these residues might form a 5-7 membered non-aromatic ring.

R16 and R17 are independently selected from among hydrogen, C1-C3 alkyl, C1-C4 alkylsulfonyl, 2-thienylsulfonyl C1-C4 alkylcarbonyl, C1-C4 alkoxycarbonyl, aminocarbonyl, and C1-C4 alkylaminocarbonyl wherein R16 and R17 might form a 5-7 membered cycle.

Another especially preferred embodiment of the present invention are compounds to according to formula IV, wherein R1 is selected from hydrogen, halogen, hydroxyl, hydroxymethyl, methoxycarbonyl, ethoxycarbonyl, methyl, ethyl, carboxy, and methoxymethyl;

R2 is selected from hydrogen, hydroxyl, methoxycarbonyl, carboxy, and hydroxymethyl;

R3 is selected from hydrogen, halogen, methyl, ethyl, methoxycarbonyl, ethoxycarbonyl, carboxy, hydroxymethyl;

R4 is hydrogen or methyl;

R5 is hydrogen or methyl;

R13 is hydrogen or methyl;

R14 is hydrogen

R15 is hydrogen or methyl;

Most preferred are compounds of formula I to IV, wherein R1 is hydroxyl or hydroxymethyl.

Further most preferred compounds according to the present invention are compounds according to formula I to IV, wherein R1 is hydroxyl or hydroxymethyl, and R2 is hydroxyl or hydrogen.

Further most preferred compounds according to the present invention are compounds according to formula I to IV, wherein R2 is hydroxyl.

Further most preferred compounds according to the present invention are compounds according to formula I to IV, wherein R2 is hydroxyl and R1 is hydroxymethyl, hydroxyl or hydrogen.

Further most preferred compounds according to the present invention are compounds according to formula I to IV, wherein R4 is hydrogen.

Further most preferred compounds according to the present invention are compounds according to formula I to IV, wherein R5 is hydrogen.

Further most preferred compounds according to the present invention are compounds according to formula I to IV, wherein R1 is hydrogen, hydroxyl or hydroxymethyl, R2 is hydroxyl, and R4 and R5 are both hydrogen.

Further most preferred compounds according to the present invention are compounds according to formula I, wherein the dotted bond represents a double bond.

Further most preferred compounds according to the present invention are compounds according to formula I to IV, wherein the doffed bond represents a double bond.

Further most preferred compounds according to the present invention are compounds according to formula I and the pharmaceutically acceptable salts or solvates thereof, in the form of a racemate or as a substantially pure enantiomer or diastereomer or mixtures of the optical isomers, selected from the group comprising 4-(2-hydroxy-3-(1-(5-phenylthieno[2,3-d]pyrimidin-4-yl)piperidin-4-ylamino)propoxy)phenol
(R)-4-(2-hydroxy-3-(1-(5-phenylthieno[2,3-d]pyrimidin-4-yl)piperidin-4-ylamino)propoxy)phenol
(S)-4-(2-hydroxy-3-(1-(5-phenylthieno[2,3-d]pyrimidin-4-yl)piperidin-4-ylamino)propoxy)phenol
4-(2-hydroxy-3-(1-(5-methylthieno[2,3-d]pyrimidin-4-yl)piperidin-4-ylamino)propoxy)phenol
4-(2-hydroxy-3-(1-(2-methylthieno[2,3-d]pyrimidin-4-yl)piperidin-4-ylamino)propoxy)phenol
4-(2-hydroxy-3-(1-(5-methyl-6-phenylthieno[2,3-d]pyrimidin-4-yl)piperidin-4-ylamino)propoxy)phenol
4-(2-hydroxy-3-(1-(5-(thiophen-2-yl)thieno[2,3-d]pyrimidin-4-yl)piperidin-4-ylamino)propoxy)phenol
4-(3-(1-(5-(4-fluorophenyl)thieno[2,3-d]pyrimidin-4-yl)piperidin-4-ylamino)-2-hydroxypropoxy)phenol
4-(3-((1-(5-(4-fluorophenyl)thieno[2,3-d]pyrimidin-4-yl)piperidin-4-yl)(methyl)amino)-2-hydroxypropoxy)phenol
Ethyl 2-hydroxy-5-(2-hydroxy-3-(1-(5-phenylthieno[2,3-d]pyrimidin-4-yl)piperidin-4-ylamino)propoxy)benzoate
4-(2-hydroxy-3-(1-(5-phenylthieno[2,3-d]pyrimidin-4-yl)piperidin-4-ylamino)propoxy)-2-(hydroxymethyl)phenol
2-hydroxy-5-(2-hydroxy-3-(1-(5-phenylthieno[2,3-d]pyrimidin-4-yl)piperidin-4-ylamino)propoxy)benzoic acid
Ethyl 2-hydroxy-5-(2-hydroxy-3-(1-(5-methylthieno[2,3-d]pyrimidin-4-yl)piperidin-4-ylamino)propoxy)benzoate
4-(2-hydroxy-3-(1-(5-methylthieno[2,3-d]pyrimidin-4-yl)piperidin-4-ylamino)propoxy)-2-(hydroxymethyl)phenol
4-(2-hydroxy-3-(1-(2-methylthieno[2,3-d]pyrimidin-4-yl)piperidin-4-ylamino)propoxy)-2-(hydroxymethyl)phenol
Ethyl 2-hydroxy-5-(2-hydroxy-3-(1-(5-methyl-6-phenylthieno[2,3-d]pyrimidin-4-yl)piperidin-4-ylamino)propoxy)benzoate
4-(2-hydroxy-3-(1-(5-methyl-6-phenylthieno[2,3-d]pyrimidin-4-yl)piperidin-4-ylamino)propoxy)-2-(hydroxymethyl)phenol
Ethyl 2-hydroxy-5-(2-hydroxy-3-(1-(5-(thiophen-2-yl)thieno[2,3-d]pyrimidin-4-yl)piperidin-4-ylamino)propoxy)benzoate
4-(2-hydroxy-3-(1-(5-(thiophen-2-yl)thieno[2,3-d]pyrimidin-4-yl)piperidin-4-ylamino)propoxy)-2-(hydroxymethyl)phenol
3-(2-Hydroxy-3-(1-(5-phenyl-thieno[2,3-d]pyrimidin-4-yl)-piperidin-4-ylamino)-propoxy)-phenol
Methyl 2-hydroxy-4-(2-hydroxy-3-(1-(5-phenylthieno[2,3-d]pyrimidin-4-yl)piperidin-4-ylamino)propoxy)benzoate
5-(2-hydroxy-3-(1-(5-phenylthieno[2,3-d]pyrimidin-4-yl)piperidin-4-ylamino)propoxy)-2-(hydroxymethyl)phenol
3-Ethyl-4-(2-hydroxy-3-(1-(5-phenylthieno[2,3-d]pyrimidin-4-yl)piperidin-4-ylamino)propoxy)phenol
2-Ethyl-4-(2-hydroxy-3-(1-(5-phenylthieno[2,3-d]pyrimidin-4-yl)piperidin-4-ylamino)propoxy)phenol
Ethyl 5-hydroxy-2-(2-hydroxy-3-(1-(5-phenylthieno[2,3-d]pyrimidin-4-yl)piperidin-4-ylamino)propoxy)benzoate
4-(2-hydroxy-3-(1-(5-phenylthieno[2,3-d]pyrimidin-4-yl)piperidin-4-ylamino)propoxy)-3-(hydroxymethyl)phenol
4-(2-hydroxy-3-(1-(thieno[3,2-d]pyrimidin-4-yl)piperidin-4-ylamino)propoxy)phenol
Ethyl 2-hydroxy-5-(2-hydroxy-3-(1-(thieno[3,2-d]pyrimidin-4-yl)piperidin-4-ylamino)propoxy)benzoate
4-(2-hydroxy-3-(1-(thieno[3,2-d]pyrimidin-4-yl)piperidin-4-ylamino)propoxy)-2-(hydroxymethylphenol
4-(3-(1-(4,6-dimethylpyrimidin-2-yl)piperidin-4-ylamino)-2-hydroxypropoxy)phenol
1-(4-(hydroxymethyl)phenoxy)-3-(1-(5-phenylthieno[2,3-d]pyrimidin-4-yl)piperidin-4-ylamino)propan-2-ol
1-(3-(hydroxymethyl)phenoxy)-3-(methyl(1-(5-methyl-6-phenylthieno[2,3-d]pyrimidin-4-yl)piperidin-4-yl)amino)propan-2-ol
1-(3-(hydroxymethyl)phenoxy)-3-(methyl(1-(5-phenylthieno[2,3-d]pyrimidin-4-yl)piperidin-4-yl)amino)propan-2-ol
1-(1-(5-(4-fluorophenyl)thieno[2,3-d]pyrimidin-4-yl)piperidin-4-ylamino)-3-(3-(hydroxymethyl)phenoxy)propan-2-ol
1-(3-(hydroxymethyl)phenoxy)-3-(1-(5-methyl-6-phenylthieno[2,3-d]pyrimidin-4-yl)piperidin-4-ylamino)propan-2-ol
1-(3-(hydroxymethyl)phenoxy)-3-(1-(2-methylthieno[2,3-d]pyrimidin-4-yl)piperidin-4-ylamino)propan-2-ol
1-(3-(hydroxymethyl)phenoxy)-3-(1-(5-methylthieno[2,3-d]pyrimidin-4-yl)piperidin-4-ylamino)propan-2-ol
1-(3-(hydroxymethyl)phenoxy)-3-(1-(5-phenylthieno[2,3-d]pyrimidin-4-yl)piperidin-4-ylamino)propan-2-ol
4-hydroxy-2-(2-hydroxy-3-(1-(5-phenylthieno[2,3-d]pyrimidin-4-yl)piperidin-4-ylamino)propoxy)benzoic acid
Methyl 4-hydroxy-2-(2-hydroxy-3-(1-(5-phenylthieno[2,3-d]pyrimidin-4-yl)piperidin-4-ylamino)propoxy)benzoate
4-(2-hydroxy-3-(1-(5-phenylthieno[2,3-d]pyrimidin-4-yl)piperidin-4-ylamino)propoxy)-2-(methoxymethyl)phenol
4-(2-hydroxy-3-(1-(5-phenyl-1,2-dihydrothieno[2,3-d]pyrimidin-4-yl piperidin-4-ylamino)propoxy)-2-(hydroxymethyl)phenol
4-(3-(1-(4,6-dimethylpyrimidin-2-yl)piperidin-4-ylamino)-2-hydroxypropoxy)-2-(hydroxymethyl)phenol 1-(1-(5-(4-fluorophenyl)thieno[2,3-d]pyrimidin-4-yl)piperidin-4-ylamino)-3-(4-(hydroxymethyl)phenoxy)propan-2-ol 2,3-difluoro-4-(2-hydroxy-3-(1-(5-phenylthieno[2,3-d]pyrimidin-4-yl)piperidin-4-ylamino)propoxy)phenol 4-(2-hydroxy-3-(1-(5-phenylthieno[2,3-d]pyrimidin-4-yl)piperidin-4-ylamino)propoxy)benzene-1,2-diol 3-fluoro-4-(2-hydroxy-3-(1-(5-phenylthieno[2,3-d]pyrimidin-4-yl)piperidin-4-ylamino)propoxy)phenol 3-(3-(1-(4,6-dimethylpyrimidin-2-yl)piperidin-4-ylamino)-2-hydroxypropoxy)phenol 1-(1-(4,6-dimethylpyrimidin-2-yl)piperidin-4-ylamino)-3-(3-(hydroxymethyl)phenoxy)propan-2-ol Further most preferred compounds according to the present invention are compounds according to formulas II and III, and the pharmaceutically acceptable salts or solvates thereof, in the form of a racemate or as a substantially pure enantiomer or diastereomer or mixtures of the optical isomers, selected from the group comprising:

4-(2-hydroxy-3-(1-(5-phenylthieno[2,3-d]pyrimidin-4-yl)piperidin-4-ylamino)propoxy)phenol (R)-4-(2-hydroxy-3-(1-(5-phenylthieno[2,3-d]pyrimidin-4-yl)piperidin-4-ylamino)propoxy)phenol (S)-4-(2-hydroxy-3-(1-(5-phenylthieno[2,3-d]pyrimidin-4-yl)piperidin-4-ylamino)propoxy)phenol 4-(2-hydroxy-3-(1-(5-methylthieno[2,3-d]pyrimidin-4-yl)piperidin-4-ylamino)propoxy)phenol 4-(2-hydroxy-3-(1-(2-methylthieno[2,3-d]pyrimidin-4-yl)piperidin-4-ylamino)propoxy)phenol 4-(2-hydroxy-3-(1-(5-methyl-6-phenylthieno[2,3-d]pyrimidin-4-yl)piperidin-4-ylamino)propoxy)phenol 4-(2-hydroxy-3-(1-(5-(2-thienyl)thieno[2,3-d]pyrimidin-4-yl)piperidin-4-ylamino)propoxy)phenol 4-(3-(1-(5-(4-fluorophenyl)thieno[2,3-d]pyrimidin-4-yl)piperidin-4-ylamino)-2-hydroxypropoxy)phenol 4-(3-((1-(5-(4-fluorophenyl)thieno[2,3-d]pyrimidin-4-yl)piperidin-4-yl)(methyl)amino)-2-hydroxypropoxy)phenol Ethyl 2-hydroxy-5-(2-hydroxy-3-(1-(5-phenylthieno[2,3-d]pyrimidin-4-yl)piperidin-4-ylamino)propoxy)benzoate 4-(2-hydroxy-3-(1-(5-phenylthieno[2,3-d]pyrimidin-4-yl)piperidin-4-ylamino)propoxy)-2-(hydroxymethyl)phenol 2-hydroxy-5-(2-hydroxy-3-(1-(5-phenylthieno[2,3-d]pyrimidin-4-yl)piperidin-4-ylamino)propoxy)benzoic acid Ethyl 2-hydroxy-5-(2-hydroxy-3-(1-(5-methylthieno[2,3-d]pyrimidin-4-yl)piperidin-4-ylamino)propoxy)benzoate 4-(2-hydroxy-3-(1-(5-methylthieno[2,3-d]pyrimidin-4-yl)piperidin-4-ylamino)propoxy)-2-(hydroxymethyl)phenol 4-(2-hydroxy-3-(1-(2-methylthieno[2,3-d]pyrimidin-4-yl)piperidin-4-ylamino)propoxy)-2-(hydroxymethyl)phenol Ethyl 2-hydroxy-5-(2-hydroxy-3-(1-(5-methyl-6-phenylthieno[2,3-d]pyrimidin-4-yl)piperidin-4-ylamino)propoxy)benzoate 4-(2-hydroxy-3-(1-(5-methyl-6-phenylthieno[2,3-d]pyrimidin-4-yl)piperidin-4-ylamino)propoxy)-2-(hydroxymethyl)phenol Ethyl 2-hydroxy-5-(2-hydroxy-3-(1-(5-(2-thienyl)thieno[2,3-d]pyrimidin-4-ylpiperidin-4-ylamino)propoxy)benzoate 4-(2-hydroxy-3-(1-(5-(2-thienyl)thieno[2,3-d]pyrimidin-4-yl)piperidin-4-ylamino)propoxy)-2-(hydroxymethyl)phenol 3-(2-Hydroxy-3-(1-(5-phenyl-thieno[2,3-d]pyrimidin-4-yl)-piperidin-4-ylamino)-propoxy)-phenol Methyl 2-hydroxy-4-(2-hydroxy-3-(1-(5-phenylthieno[2,3-d]pyrimidin-4-yl)piperidin-4-ylamino)propoxy)benzoate 5-(2-hydroxy-3-(1-(5-phenylthieno[2,3-d]pyrimidin-4-yl)piperidin-4-ylamino)propoxy)-2-(hydroxymethyl)phenol 3-Ethyl-4-(2-hydroxy-3-(1-(5-phenylthieno[2,3-d]pyrimidin-4-yl)piperidin-4-ylamino)propoxy)phenol 2-Ethyl-4-(2-hydroxy-3-(1-(5-phenylthieno[2,3-d]pyrimidin-4-yl)piperidin-4-ylamino)propoxy)phenol Ethyl 5-hydroxy-2-(2-hydroxy-3-(1-(5-phenylthieno[2,3-d]pyrimidin-4-yl)piperidin-4-ylamino)propoxy)benzoate 4-(2-hydroxy-3-(1-(5-phenylthieno[2,3-d]pyrimidin-4-yl)piperidin-4-ylamino)propoxy)-3-(hydroxymethyl)phenol 4-(2-hydroxy-3-(1-(thieno[3,2-d]pyrimidin-4-yl)piperidin-4-ylamino)propoxy)phenol Ethyl 2-hydroxy-5-(2-hydroxy-3-(1-(thieno[3,2-d]pyrimidin-4-yl piperidin-4-ylamino)propoxy)benzoate 4-(2-hydroxy-3-(1-(thieno[3,2-d]pyrimidin-4-yl)piperidin-4-ylamino)propoxy)-2-(hydroxymethyl)phenol 1-(4-(hydroxymethyl)phenoxy)-3-(1-(5-phenylthieno[2,3-d]pyrimidin-4-yl)piperidin-4-ylamino)propan-2-ol 1-(3-(hydroxymethyl)phenoxy)-3-(methyl(1-(5-methyl-6-phenylthieno[2,3-d]pyrimidin-4-yl)piperidin-4-yl)amino)propan-2-ol 1-(3-(hydroxymethyl)phenoxy)-3-(methyl(1-(5-phenylthieno[2,3-d]pyrimidin-4-yl)piperidin-4-yl)amino)propan-2-ol 1-(1-(5-(4-fluorophenyl)thieno[2,3-d]pyrimidin-4-yl)piperidin-4-ylamino)-3-(3-(hydroxymethyl)phenoxy)propan-2-ol 1-(3-(hydroxymethyl)phenoxy)-3-(1-(5-methyl-6-phenylthieno[2,3-d]pyrimidin-4-yl)piperidin-4-ylamino)propan-2-ol 1-(3-(hydroxymethyl)phenoxy)-3-(1-(2-methylthieno[2,3-d]pyrimidin-4-yl)piperidin-4-ylamino)propan-2-ol 1-(3-(hydroxymethyl)phenoxy)-3-(1-(5-methylthieno[2,3-d]pyrimidin-4-yl)piperidin-4-ylamino)propan-2-ol 1-(3-(hydroxymethyl)phenoxy)-3-(1-(5-phenylthieno[2,3-d]pyrimidin-4-yl)piperidin-4-ylamino)propan-2-ol 4-hydroxy-2-(2-hydroxy-3-(1-(5-phenylthieno[2,3-d]pyrimidin-4-yl)piperidin-4-ylamino)propoxy)benzoic acid Methyl 4-hydroxy-2-(2-hydroxy-3-(1-(5-phenylthieno[2,3-d]pyrimidin-4-yl)piperidin-4-ylamino)propoxy)benzoate 4-(2-hydroxy-3-(1-(5-phenylthieno[2,3-d]pyrimidin-4-yl)piperidin-4-ylamino)propoxy)-2-(methoxymethyl)phenol 4-(2-hydroxy-3-(1-(5-phenyl-1,2-dihydrothieno[2,3-d]pyrimidin-4-yl)piperidin-4-ylamino)propoxy)-2-(hydroxymethyl)phenol 1-(1-(5-(4-fluorophenyl)thieno[2,3-d]pyrimidin-4-yl)piperidin-4-ylamino)-3-(4-(hydroxymethyl)phenoxy)propan-2-ol 2,3-difluoro-4-(2-hydroxy-3-(1-(5-phenylthieno[2,3-d]pyrimidin-4-yl)piperidin-4-ylamino)propoxy)phenol 4-(2-hydroxy-3-(1-(5-phenylthieno[2,3-d]pyrimidin-4-yl)piperidin-4-ylamino)propoxy)benzene-1,2-diol 3-fluoro-4-(2-hydroxy-3-(1-(5-phenylthieno[2,3-d]pyrimidin-4-yl)piperidin-4-ylamino)propoxy)phenol Especially preferred compounds according to the present invention are compounds according to formula I-IV and the pharmaceutically acceptable salts or solvates thereof, in the form of a racemate or as a substantially pure enantiomer or diastereomer or mixtures of the optical isomers, selected from the group comprising 4-(2-hydroxy-3-(1-(5-phenylthieno[2,3-d]pyrimidin-4-yl)piperidin-4-ylamino)propoxy)phenol;

(S)-4-(2-hydroxy-3-(1-(5-phenylthieno[2,3-d]pyrimidin-4-yl)piperidin-4-ylamino)propoxy)phenol;

4-(3-(1-(5-(4-fluorophenyl)thieno[2,3-d]pyrimidin-4-yl)piperidin-4-ylamino)-2-hydroxypropoxy)phenol;

4-(2-hydroxy-3-(1-(5-phenylthieno[2,3-d]pyrimidin-4-yl)piperidin-4-ylamino)propoxy)-2-(hydroxymethyl)phenol;

4-(2-hydroxy-3-(1-(5-methylthieno[2,3-d]pyrimidin-4-yl)
piperidin-4-ylamino)propoxy)-2-(hydroxymethyl)phenol;
4-(2-hydroxy-3-(1-(2-methylthieno[2,3-d]pyrimidin-4-yl)
piperidin-4-ylamino)propoxy)-2-(hydroxymethyl)phenol;
4-(2-hydroxy-3-(1-(5-methyl-6-phenylthieno[2,3-d]pyrimidin-4-yl)piperidin-4-ylamino)propoxy)-2-(hydroxymethyl)phenol;
4-(2-hydroxy-3-(1-(5-(2-thienyl)thieno[2,3-d]pyrimidin-4-yl)piperidin-4-ylamino)propoxy)-2-(hydroxymethyl)phenol;
2-ethyl-4-(2-hydroxy-3-(1-(5-phenylthieno[2,3-d]pyrimidin-4-yl)piperidin-4-ylamino)propoxy)phenol;
4-(2-hydroxy-3-(1-(5-phenylthieno[2,3-d]pyrimidin-4-yl)
piperidin-4-ylamino)propoxy)-3-(hydroxymethyl)phenol;
4-(2-hydroxy-3-(1-(thieno[3,2-d]pyrimidin-4-yl)piperidin-4-ylamino)propoxy)-2-(hydroxymethyl)phenol;
1-(4-(hydroxymethyl)phenoxy)-3-(1-(5-phenylthieno[2,3-d]pyrimidin-4-yl)piperidin-4-ylamino)propan-2-ol;
4-(2-hydroxy-3-(1-(5-phenylthieno[2,3-d]pyrimidin-4-yl)
piperidin-4-ylamino)propoxy)-2-(methoxymethyl)phenol;
4-(2-hydroxy-3-(1-(5-phenyl-1,2-dihydrothieno[2,3-d]pyrimidin-4-yl)piperidin-4-ylamino)propoxy)-2-(hydroxymethyl)phenol;
4-(3-(1-(4,6-dimethylpyrimidin-2-yl)piperidin-4-ylamino)-2-hydroxypropoxy)-2-(hydroxymethyl)phenol;
3-(2-Hydroxy-3-(1-(5-phenyl-thieno[2,3-d]pyrimidin-4-yl)-piperidin-4-ylamino)-propoxy)-phenol
2,3-difluoro-4-(2-hydroxy-3-(1-(5-phenylthieno[2,3-d]pyrimidin-4-yl)piperidin-4-ylamino)propoxy)phenol
4-(2-hydroxy-3-(1-(5-phenylthieno[2,3-d]pyrimidin-4-yl)
piperidin-4-ylamino)propoxy)benzene-1,2-diol
3-fluoro-4-(2-hydroxy-3-(1-(5-phenylthieno[2,3-d]pyrimidin-4-yl)piperidin-4-ylamino)propoxy)phenol
3-(3-(1-(4,6-dimethylpyrimidin-2-yl)piperidin-4-ylamino)-2-hydroxypropoxy)phenol
1-(1-(4,6-dimethylpyrimidin-2-yl)piperidin-4-ylamino)-3-(3-(hydroxymethyl)phenoxy)propan-2-ol Especially preferred compounds according to the present invention are compounds according to formulas II and III, and the pharmaceutically acceptable salts or solvates thereof, in the form of a racemate or as a substantially pure enantiomer or diastereomer or mixtures of the optical isomers, selected from the group comprising:
4-(2-hydroxy-3-(1-(5-phenylthieno[2,3-d]pyrimidin-4-yl)
piperidin-4-ylamino)propoxy)phenol;
(S)-4-(2-hydroxy-3-(1-(5-phenylthieno[2,3-d]pyrimidin-4-yl)piperidin-4-ylamino)propoxy)phenol;
4-(3-(1-(5-(4-fluorophenyl)thieno[2,3-d]pyrimidin-4-yl)piperidin-4-ylamino)-2-hydroxypropoxy)phenol;
4-(2-hydroxy-3-(1-(5-phenylthieno[2,3-d]pyrimidin-4-yl)
piperidin-4-ylamino)propoxy)-2-(hydroxymethyl)phenol;
4-(2-hydroxy-3-(1-(5-methylthieno[2,3-d]pyrimidin-4-yl)
piperidin-4-ylamino)propoxy)-2-(hydroxymethyl)phenol;
4-(2-hydroxy-3-(1-(2-methylthieno[2,3-d]pyrimidin-4-yl)
piperidin-4-ylamino)propoxy)-2-(hydroxymethyl)phenol;
4-(2-hydroxy-3-(1-(5-methyl-6-phenylthieno[2,3-d]pyrimidin-4-yl)piperidin-4-ylamino)propoxy)-2-(hydroxymethyl)phenol;
4-(2-hydroxy-3-(1-(5-(2-thienyl)thieno[2,3-d]pyrimidin-4-yl)piperidin-4-ylamino)propoxy)-2-(hydroxymethyl)phenol;
2-ethyl-4-(2-hydroxy-3-(1-(5-phenylthieno[2,3-d]pyrimidin-4-yl)piperidin-4-ylamino)propoxy)phenol;
4-(2-hydroxy-3-(1-(5-phenylthieno[2,3-d]pyrimidin-4-yl)
piperidin-4-ylamino)propoxy)-3-(hydroxymethyl)phenol;
4-(2-hydroxy-3-(1-(thieno[3,2-d]pyrimidin-4-yl)piperidin-4-ylamino)propoxy)-2-(hydroxymethyl)phenol;
1-(4-(hydroxymethyl)phenoxy)-3-(1-(5-phenylthieno[2,3-d]pyrimidin-4-yl)piperidin-4-ylamino)propan-2-ol;
4-(2-hydroxy-3-(1-(5-phenylthieno[2,3-d]pyrimidin-4-yl)
piperidin-4-ylamino)propoxy)-2-(methoxymethyl)phenol;
4-(2-hydroxy-3-(1-(5-phenyl-1,2-dihydrothieno[2,3-d]pyrimidin-4-yl)piperidin-4-ylamino)propoxy)-2-(hydroxymethyl)phenol;
3-(2-Hydroxy-3-(1-(5-phenyl-thieno[2,3-d]pyrimidin-4-yl)-piperidin-4-ylamino)-propoxy)-phenol
2,3-difluoro-4-(2-hydroxy-3-(1-(5-phenylthieno[2,3-d]pyrimidin-4-yl)piperidin-4-ylamino)propoxy)phenol
4-(2-hydroxy-3-(1-(5-phenylthieno[2,3-d]pyrimidin-4-yl)
piperidin-4-ylamino)propoxy)benzene-1,2-diol
3-fluoro-4-(2-hydroxy-3-(1-(5-phenylthieno[2,3-d]pyrimidin-4-yl)piperidin-4-ylamino)propoxy)phenol One representative example out of the above mentioned compounds was tested in a to binding assay on tachykinin NK1, NK2 and NK3 receptors at a compound concentration of 10 μM and displayed inhibitions which would correlate into $IC_{50}$ values of around or above 10 μM on each receptor. Comparing these affinities with those described in WO2004014850, compounds of the invention do not show sufficient affinity to qualify as NK1 ligands. Binding assays for affinity at tachykinin receptors NK1, NK2 and NK3 were performed at MDS Pharma Services (Bothell, USA), methods have been adapted from the following scientific literature:
NK1 (Catalog No. 255510) and NK2 (Catalog No. 255600): R. Patacchini et al., *Arch. Int. Pharmacodyn.* 1995, 329, 161.
NK3 (Catalog No. 255710): J. E. Krause et al., *Proc. Natl. Acad. Sci. USA* 1997, 94, 310; S. Sadowski et al., Neuropeptides 1993, 24, 317.

Another subject of the present invention is the use of the compounds according to the present invention as a medicament.

Another subject of the present invention is a pharmaceutical composition comprising a compound according to the present invention and a pharmaceutically acceptable excipient.

A further subject of the present invention is the use of a compound according to the present invention for the preparation of a medicament for the treatment of a disease that is associated with the decreased activation and/or expression of adrenergic beta 3 receptors.

In another embodiment of the invention, a further subject of the present invention is the use of a compound according to the present invention for the preparation of a medicament for the treatment of a disease that is associated with modification of β3 adrenoceptor activity and/or expression.

A preferred subject of the present invention is the use of a compound according to the present invention for the preparation of a medicament for the treatment of an urinary tract disorder, the treatment of a gastrointestinal disorder, the prevention or treatment of dysmenorrhea, the induction and/or enhancement of tocolysis, or the treatment of depression or anxiety disorders.

Especially preferred is the use of any of the compounds according to the present invention, wherein the disorder is urinary incontinence.

Especially preferred is also the use of any of the compounds according to the present invention, wherein the disorder is urinary stress incontinence.

Especially preferred is further the use of any of the compounds according to the present invention, wherein the disorder is urinary urge incontinence.

Especially preferred is further the use of any of the compounds according to the present invention, for the preparation of a medicament for the treatment of obesity or diabetes.

Subject of the present invention is further a method of treating a patient suffering from a disease that improves on stimulation of the adrenergic beta 3 receptor, said method comprising the administration of a compound according to the present invention to said patient.

A preferred subject of the present invention is a method of treating a patient suffering from obesity, diabetes and/or incontinence, said method comprising the administration of a therapeutically effective amount of a compound according to the present invention to said patient.

β3-adrenoceptor agonists of the aryloxypropanolamine scaffold which combine high functional potency and decent selectivity over β1- and β2-adrenoceptors are still rare and thus required. Compounds according to the present invention exhibit high functional potency and decent selectivity over β1- and β2-adrenoceptors.

Alternatively, compounds according to the present invention exhibit high functional potency or decent selectivity over β1- and β2-adrenoceptors.

Preferred are compounds according to the present invention having an $EC_{50}(\beta3) \leq 100$ nM.

Also preferred are compounds according to the present invention having a selectivity of A×B>100. Selectivity has been defined as outlined below.

Most preferred are compounds according to the present invention with $EC_{50}(\beta3) \leq 100$ nM and selectivity A×B>100.

Further most preferred compounds according to the present invention exhibit $EC_{50}(\beta3) \leq 10$ nM.

Further most preferred are compounds with $EC_{50}(\beta3) \leq 10$ nM and selectivity A×B>100.

Another subject of the present invention is a method for producing a compound according to the present invention, comprising the steps
1) treatment of a phenol derivative with a methylene oxirane derivative selected from the group comprising epibromohydrin, epichlorohydrin and glycidyl tosylate under basic conditions
2) treatment of a chloropyrimidine derivative with an amine
3) nucleophilic ring opening of the oxirane as obtained by step (1) with the amine as obtained by step (2),
wherein the order of steps 1 or 2 is interchangeable.

A person skilled in the art would understand that these reaction steps might require incorporation of a protective group strategy for certain building blocks.

The present invention further comprises a method of producing a compound according to the present invention characterized by the following steps:

Decisive procedure for the construction of compounds has been the nucleophilic ring opening of an oxirane with amines simply by heating the reactants in an appropriate solvent. Aryloxymethyloxiranes themselves were usually generated by treatment of an appropriately substituted and/or protected phenol derivative with either epibromohydrine and an alkali carbonate or sodium hydride and glycidyl tosylate. The amine required for ring opening was prepared from chloropyrimidine derivatives, which were coupled with a protected aminopiperidine in ethyleneglycol under elevated temperature, followed by amine liberation by removal of the protective group. Final synthetic steps included removal of protective groups and/or functional group transformations. References of literature procedures are given below along with synthetic standard protocols.

EXAMPLES

Selectivity Criteria

Compounds were found to display agonistic activity at β3- and β1-adrenoceptors, but antagonistic activity at β2-receptors. Selectivity for β3 over the other two adrenoceptors was thus defined as:
A) selectivity factor for β3 over $\beta1 = K_i(\beta1)/K_i(\beta3)$;
B) selectivity factor for β3 over $\beta2 = K_i(\beta2)/EC_{50}(\beta3)$;
overall selectivity was determined as factor A) multiplied by factor B)

Assay systems are described below.

Biological Assay Systems

Radioligand Binding Assay (RBA):

Membrane preparations containing human β1-, β2- or β3-adrenergic receptors were purchased from Euroscreen. The radioligand for all three receptor subtypes was [125I]-Iodine cyanopindolol (125I-CYP).

Determination of $IC_{50}$ deployed a competition binding experiment where an unlabeled test compound competes with the radioligand for the receptor's binding site.

a) β3-Assay

For competition binding experiments 0.1 μg/μL β3 membranes were pre-incubated with the respective compounds at r.t. for 10 minutes. The binding buffer consisted of 25 mM Hepes, 1 mM EDTA, 0.5% BSA pH 7.4. All incubation steps were done in a 96 well Masterblock PP/1 mL (Greiner), the total assay volume was 100 μL. 125I-CYP (Amersham) was added to a final concentration of 1.5 nM to each well and the reaction mixture was incubated for 1.5 h at r.t. to reach equilibrium.

The reaction mixtures were transferred to a 96 well UnifilterGF/B filter plate (Millipore), pre-soaked in 0.5% BSA, using the PerkinElmer filtermate. Each well was washed with 8×1 mL ice cold binding buffer supplemented with 0.5M NaCl. The GF/B filter plates were dried for 5 min on the filtermate. To each well, 50 μL OptiPhase scintillation cocktail (PerkinElmer) was added and incubated at r.t. for 10 min.

Bound radioactivity was quantified in a Wallac-Microbeta plate reader (PerkinElmer). Each well was counted for 2 min in top-count mode.

b) β1/β2-Assay

For competition binding experiments 0.25 μg/well β1 or 0.5 μg/well β2 membranes were pre-incubated with the respective compounds at r.t. for 10 minutes. The binding buffer consisted of 25 mM Tris-HCl pH 7.4, 154 mM NaCl, 1 mM ascorbic acid, 0.01% saponine. All incubation steps were done in a 96 well Masterblock PP/1 mL (Greiner), the total assay volume was 250 μL. 125I-CYP (Amersham) was added to a final concentration of 0.05 nM to each well and the reaction mixture was incubated for 2 h at r.t. to reach equilibrium.

The reaction mixtures were transferred to a 96 well UnifilterGF/B filter plate (Millipore), pre-soaked in 0.5% PEI, using the PerkinElmer filtermate, Each well was wash with 8×1 mL ice cold binding buffer. The GF/B filter plates were dried for 5 min on the filtermate. To each well 50 μL OptiPhase scintillation cocktail (PerkinElmer) was added and incubated at r.t. for 10 min.

Bound radioactivity was quantified in a Wallac-Microbeta plate reader (PerkinElmer). Each well was counted for 2 min in top-count mode Functional Cell Assays:
(Cyclic Amp Accumulation Assay)

Functional response of cells (agonistic or antagonistic) to the test compounds was tested by measurement of cyclic AMP formation. Therefore cyclic AMP was quantitatively determined by HTRF® (Homogeneous Time-Resolved Fluorescence) technology (Cisbio International) using a stable cell line CHO-K1 β3 expressing the human recombinant adrenergic β3 receptor (Euroscreen).

The CHO-K1 β3 cell line was maintained in Ham's F12 medium containing 10% fetal bovine serum, 400 μg/ml geneticin (G418), 100 U/mL penicillin and 100 μg/mL streptomycin (all PAA) at 37° C. and 5% $CO_2$. Cells in mid-log phase, grown in media without antibiotics during 18 h prior to the experiment, were detached by gentle flushing with 2 ml PBS-EDTA pH 7.5 (Cambrex) and resuspended in 8 mL of medium without antibiotics. Cells were then counted, centrifuged in a 30 mL PP tube (Corning) at 2000 rpm for 1 min and resuspended in HBSS/20 mM HEPES/0.05% BSA buffer (all PAA) including 1 mM IBMX (Sigma). Cells were then dispensed at $3.2 \times 10^5$–$3.6 \times 10^5$ cells/well in black 96-half well microtiter plates (Corning). After addition of the test compounds for dose response curves the plates were incubated for 10 min at room temperature.

For the antagonist assay (−)-isoproterenol hydrochloride (Sigma) at a final concentration of 100 μM was added to the wells and incubated another 30 min.

cAMP HTRF® Kit reagents were then added as recommended by the manufacturer and plates were sealed with plate sealer. After 1 hour of incubation the plates were read in a Tecan Ultra Reader using the "multilabeling" option of Tecan Xfluor4 software with the following parameters, excitation filter 320 nm, mirror dichroic2, lag time 150 μs, integration time 500 μs, number of flashes 10, optimal gain and z-position. For measurement 1 an emission filter at 620 nm and for measurement 2 an emission filter at 665 nm was chosen.

$EC_{50}$ value calculation for the agonist assay and $IC_{50}$ value calculation for the antagonist assay, respectively, were performed with the MS Excel Solver function based on a four-parameter fit.

Agonist and antagonist activities on the human recombinant β1- and β2-adrenergic receptors were determined at Euroscreen (Brussels, Belgium) using a HTRF-cAMP Assay (Catalog No.: ES-033-C and ES-034-C). Cells (Euroscreen cell lines expressing the recombinant β3 or β2) in mid-log phase and grown for 20 hours in media without antibiotics are detached with PBS-EDTA. After centrifugation, cells are resuspended in KRH-IBMX (5 mM KCl, 1.25 mM $MgSO_4$, 124 mM NaCl, 25 mM HEPES pH 7.4, 13.3 mM Glucose, 1.25 mM $KH_2PO_4$, 1.45 mM $CaCl_2$, 0.5 g/L BSA supplemented with 1 mM IBMX).

96 well plates (Costar, cat. no. 3694) are then successively filled with KRH-IBMX, cells ($5 \times 10^3$ cells/well) and increasing concentrations of agonistic test compound (diluted in KRH-IBMX). For antagonist assay, cells are incubated with increasing concentrations of test compound for 10 min. before addition of the reference agonist at a concentration corresponding to the $EC_{80}$.

The plate is then incubated for 30 min. at room temperature. After addition of the lysis buffer, cAMP concentrations are estimated with an HTRF kit from Cis-Bio International (cat. no. 62AM2PEB).

Standard protocols
Syntheses of Building Blocks:
A) Oxiranes:

4-(tert-Butyl-dimethyl-silanyloxy)-phenol

4-Hydroxyphenyl benzoate (9.0 mmol) was dissolved in $CH_2Cl_2$ (9 mL/mmol), TBDMS-Cl (1.5 eq., 13.5 mmol) and imidazole (2.0 eq., 18.0 mmol) were added and the mixture was stirred at r.t. overnight. The mixture was diluted with MeOH (4.5 mL/mmol), and $NaBH_4$ (2.5 eq., 22.5 mmol) was added slowly over 5 min (attention: vigorous gas evolution). The mixture was concentrated by removing $CH_2Cl_2$ under reduced pressure and the suspension was heated to 65° C. for 15 h.

The reaction was quenched by adding satd aq. $NH_4Cl$, diluted with brine and 1.3 N aq. HCl (1:1). Extraction was performed with $CHCl_3$ (2×) and ethyl acetate (2×). Title compound was attained upon purification by Flash Master Personal (20 g silica gel cartridge, PE to PE/ethyl acetate 10:1) with 90% yield.

4-(adamantane-1-carbonyloxy)-2-ethylphenol

2-Ethylhydroquinone (1.85 mmol) and 1-adamantanecarbonyl chloride (1.4 eq.) were suspended in $CH_2Cl_2$ (3 mL/mmol), pyridine (1 mmol) was added, and the mixture stirred at r.t. for 48 h.

The mixture was diluted with ethyl acetate, which was extracted once with half satd aq. $NaHCO_3$ and brine (4:1) and twice with aq. $CuSO_4$ (6 g $CuSO_4 \cdot 5H_2O$ in 100 mL; 2×). Title compound was attained upon purification by prep. TLC (2 mm silica gel, PE/ethyl acetate 3:1) with 86% yield.

4-(methoxymethoxy)phenol

To a mixture of 4-hydroxyphenyl benzoate (8.0 mmol) and DIEA (1.5 eq.) in $CH_2Cl_2$ (2 mL/mmol) was added chloromethoxymethane (Aldrich, 1.2 eq.). After stirring for 5 h at r.t., aq. ammonia was added and the organic phase was separated. The aq phase was extracted with $CH_2Cl_2$ (2×), combined organic phases were washed with water, and dried over $MgSO_4$ to give a colorless oil which solidified on standing overnight (90% yield).

Crude product was dissolved in MeOH (2.5 mL/mmol) and $H_2O$ (1 mL/mmol) and was treated with LiOH×$H_2O$ (3.0 eq.) at refluxed for 3 h. The methanol was removed in vacuo, and the remaining aq. mixture was partitioned between half satd aq. $NaHCO_3$ and EtOAc (3×). The combined organic phases were washed with water and brine and dried over $MgSO_4$ to give the title compound with 81% yield (second step).

Standard Protocol 1
MOM-Protection of Phenols:
a) The respective phenol (1.0 eq.) was dissolved in butanone (10 mL/mmol), $Cs_2CO_3$ (2.5 eq.) and MOM-Cl (3.0 eq.) were added, and the mixture was stirred at 55° C. for 50 h.

$Cs_2CO_3$ was filtered off, the filter cake was washed extensively with acetone and the filtrate was concentrated. Product isolation was performed by 4-(adamantane-1-carbonyloxy)-2-ethyl-1-(methoxymethoxy)phenyl Synthesis followed SP1a, using 1.2 mmol 4-(adamantane-1-carbonyloxy)-2-ethylphenol to give the title compound upon purification by prep. TLC (2×2 mm silica gel, PE/CH$_2$Cl$_2$/MeOH 20:4:1) with 64% yield.

ethyl 2-hydroxy-5-(methoxymethoxy)benzoate

Synthesis followed SP1a, using 2.2 mmol ethyl 2,5-dihydroxybenzoate to give the title compound upon purification by prep. TLC (2×2 mm silica gel, PE/CH$_2$Cl$_2$/MeOH 20:4:1) with 60% yield.
b) The respective phenol (1.0 eq.) was dissolved in butanone (10 mL/mmol), K$_2$CO$_3$ (2.2 eq.) and MOM-Cl (2.0 eq.) were added, and the mixture was stirred at 60° C. for 48 h. Workup was in accordance to variant a).

methyl 2-hydroxy-4-(methoxymethoxy)benzoate

Synthesis followed SP1b, using 2.4 mmol methyl 2,4-dihydroxybenzoate to give the title compound upon purification by Flash Master Personal (20 g silica gel cartridge, PE/ethyl acetate 15:1 to 10:1) and prep. TLC (2 mm silica gel, PE/ethyl acetate 4:1) with 81% yield.
Standard Protocol 2
(in analogy to, e.g., S. Wagner et al., *Bioorg. Med. Chem.* 2004, 12, 4117; E. Elzein et al., *Bioorg. Med. Chem. Lett.* 2004, 14, 973).

General Synthesis of 2-(aryloxymethyl)oxiranes

The respective phenol (1.0 eq.) was dissolved in butanone (5 mL/mmol), K$_2$CO$_3$ (3.0 eq.) and epibromohydrine (2.5 eq.) were added and the mixture was heated to 80° C. for 42 h.
K$_2$CO$_3$ was filtered off, the filter cake was washed extensively with acetone and the filtrate was concentrated.

2-((4-(adamantane-1-carbonyloxy)-2-ethylphenoxy)methyl)oxirane

Synthesis followed SP2, using 0.39 mmol 4-(adamantane-1-carbonyloxy)-2-ethylphenol to give the title compound upon purification by prep. TLC (1 mm silica gel, PE/CH$_2$Cl$_2$/MeOH 20:4:1) with 45% yield.

2-((3-ethyl-4-(methoxymethoxy)phenoxy)methyl)oxirane 3-ethyl-4-(methoxymethoxy)phenol was synthesized from 4-(adamantane-1-carbonyloxy)-2-ethyl-1-(methoxymethoxy)phenyl (0.75 mmol) by ester saponification according to SP10. The reaction was quenched with aq. satd NH$_4$Cl solution and extracted with CH$_2$CO$_2$ (3×). Crude product was directly used in a conversion with epibromohydrine according to SP2 to give the title compound upon purification by prep. TLC (1 mm silica gel, PE/CH$_2$Cl$_2$/MeOH 20:4:1) with 15% yield.

3-(oxiran-2-ylmethoxy)phenyl benzoate

Synthesis followed SP2, using 8.0 mmol 3-hydroxyphenyl benzoate to give the title compound upon purification by Flash Master Personal (20 g silica gel cartridge, PE to PE/ethyl acetate 15:1) with 58% yield.

(3-(oxiran-2-ylmethoxy)phenyl)methanol

Synthesis followed SP2 (reaction time 24 h), using 5.0 mmol 3-(hydroxymethyl)phenol to give the title compound upon purification by Flash Master Personal (20 g silica gel cartridge, PE/ethyl acetate 12:1 to 2:1) with 86% yield.

(4-(oxiran-2-ylmethoxy)phenyl)methanol

Synthesis followed SP2 (reaction time 24 h), using 2.0 mmol 4-(hydroxymethyl)phenol to give the title compound upon purification by prep. TLC (2 mm silica gel, PE/CH$_2$Cl$_2$/MeOH 10:16:3) with 57% yield.

2-((3,4-dimethoxyphenoxy)methyl)oxirane

Synthesis followed SP2, using 3.0 mmol 3,4-dimethoxyphenol to give the title compound upon purification by prep. TLC (2 mm silica gel, PE/CH$_2$Cl$_2$/MeOH 4:6:1) with 80% yield.
Modification of Standard Protocol 2:
a) for hydroxyphenols with ester functionalities adjacent to the hydroxy group to stay non-alkylated:
Procedure in accordance to SP2, but acetone was used as solvent and mixtures were heated to 55° C. for 42 h.

ethyl 2-hydroxy-5-(oxiran-2-ylmethoxy)benzoate

Synthesis followed SP2a, using 1.4 mmol ethyl 2,5-dihydroxybenzoate to give the title compound upon purification by prep. TLC (2 mm silica gel, PE/CH$_2$Cl$_2$/MeOH 60:70:15) with 58% yield.

methyl 2-hydroxy-4-(oxiran-2-ylmethoxy)benzoate

Synthesis followed SP2a, using 4.0 mmol methyl 2,4-dihydroxybenzoate to give the title compound upon purification by Flash Master Personal (20 g silica gel cartridge, PE/ethyl acetate 12:1 to 9:1) with 73% yield.
b) for hydroxyphenols with ester functionalities adjacent to the hydroxy group to be alkylated or decreased reactivity towards alkylation following SP2:
Procedure in accordance to SP2, but Cs$_2$CO$_3$ was used as base.

ethyl 5-(methoxymethoxy)-2-(oxiran-2-ylmethoxy)benzoate

Synthesis followed SP2b, using 0.85 mmol ethyl 2-hydroxy-5-(methoxymethoxy)benzoate to give the title compound upon purification by prep. TLC (1 mm silica gel, PE/CH$_2$Cl$_2$/MeOH 20:4:1) with 77% yield.

methyl 4-(methoxymethoxy)-2-(oxiran-2-ylmethoxy)benzoate

Synthesis followed SP2b, using 1.5 mmol methyl 2-hydroxy-4-(methoxymethoxy)benzoate to give the title compound upon purification by prep. TLC (2 mm silica gel, PE/ethyl acetate 1:1) with 84% yield.

2-((2,3-difluoro-4-methoxyphenoxy)methyl)oxirane

Synthesis followed SP2b (reaction time 24 h), using 3.0 mmol 2,3-difluoro-4-methoxyphenol to give the title compound upon purification by prep. TLC (2 mm silica gel, PE/CH$_2$Cl$_2$/MeOH 4:6:1) with 69% yield.

Standard Protocol 3
(in analogy to, e.g., M. Satyanarayana et al., *Bioorg. Med. Chem.* 2004, 12, 883; L. G. Fisher et al., *Bioorg. Med. Chem. Lett.* 1996, 6, 2253; A. E. Weber et al., *Bioorg. Med. Chem. Lett.* 1998, 8, 1101)

General synthesis of 2-(aryloxymethyl)oxiranes

NaH (1.1 eq.) was dissolved in abs. THF (3 mL/mmol) and cooled to 0° C. The respective phenol (1.0 eq.) was added at 0° C., and the solution was stirred at r.t. for 30 min. Abs. DMF (2 mL/mmol) and (R)- or (S)-oxiran-2-yl 4-methylbenzenesulfonate (1.0 eq.) was added at 0° C. and the solution was stirred at r.t. for 22 h.

The solution was diluted with aq. NaHCO$_3$ (5%, 20 mL/mmol) and extracted with CH$_2$Cl$_2$ (2×20 mL/mmol) and ethyl acetate (1×20 ml/mmol). Combined org. phases were dried over MgSO$_4$.

(R)-2-((4-(methoxymethoxy)phenoxy)methyl)oxirane

Synthesis followed SP3, using 3.0 mmol 4-(methoxymethoxy)phenol and (R)-oxiran-2-yl 4-methylbenzenesulfonate to give the title compound upon purification by Flash Master Personal (20 g silica gel cartridge, PE/ethyl acetate 6:1 to 4:1) with 77% yield.

(S)-2-((4-(methoxymethoxy)phenoxy)methyl)oxirane

Synthesis followed SP3, using 6.0 mmol 4-(methoxymethoxy)phenol and (S)-oxiran-2-yl 4-methylbenzenesulfonate to give the title compound upon purification by Flash Master Personal (20 g silica gel cartridge, PE/ethyl acetate 6:1 to 4:1) with 72% yield.

Modification of Standard Protocol 3:
a) Procedure in accordance to SP3, but no DMF was added prior to the addition of epibromohydrine (3.0 eq.).
NaBr was filtered off, the filter cake was washed vigorously with acetone, and the is filtrate was fractionated by Flash Master Personal, 20 g silica gel cartridge.

tert-butyldimethyl(4-(oxiran-2-ylmethoxy)phenoxy)silane

Synthesis followed SP3a, using 4.1 mmol 4-(tert-Butyldimethyl-silanyloxy)-phenol and racemic epibromohydrine to give the title compound upon purification by Flash Master Personal (20 g silica gel cartridge, PE to PE/ethyl acetate 15:1) with 21% yield.

2-((2-fluoro-4-methoxyphenoxy)methyl)oxirane

Synthesis followed SP3a, using 3.5 mmol 2-fluoro-4-methoxyphenol and racemic epibromohydrine to give the title compound upon purification by Flash Master Personal (20 g silica gel cartridge, PE to PE/ethyl acetate 5:1) with 48% yield.

B) Amine:
Standard Protocol 4
(in analogy to T. Kumagai et al., *Bioorg. Med. Chem.* 2001, 9, 1349)

Amination of 4-chloroquinazolines and 2-chloropyrimidines

A mixture of the respective chloro-compound (1.0 eq.) and 4-(N-Boc-amino)piperidine (1.4 eq.) in ethylene glycol (2.5 mL/mmol) was heated to 110° C. for 6 h.

For Boc-removal, 4 M HCl/dioxane (2.5 mL/mmol) was added under cooling (ice bath) and the mixture was stirred at r.t. for 2 h.

The solution was partitioned between 1.3 N aq. NaOH/brine (2:1, 20 mL/mmol) and CHCl$_3$ (4×10 mL/mmol). Combined organic phases were dried over MgSO$_4$ to give crude product.

1-(5-(2-thienyl)thieno[2,3-d]pyrimidin-4-yl)piperidin-4-amine

Synthesis followed SP4, using 1.4 mmol 4-Chloro-5-(2-thienyl)thieno[2,3-d]pyrimidine to give the title compound quantitatively, containing around 25% water even upon extensive drying in high vacuum.

1-(5-(4-fluorophenyl)thieno[2,3-d]pyrimidin-4-yl)piperidin-4-amine

Synthesis followed SP4, using 2.0 mmol 4-chloro-5-(4-fluorophenyl)thieno[2,3-d]pyrimidine to give the title compound with 77% yield.

1-(5-methyl-6-phenylthieno[2,3-d]pyrimidin-4-yl)piperidin-4-amine

Synthesis followed SP4, using 1.8 mmol 4-chloro-5-methyl-6-phenylthieno[2,3-d]pyrimidine to give the title compound quantitatively, containing around 20% water even upon extensive drying in high vacuum.

1-(5-methylthieno[2,3-d]pyrimidin-4-yl)piperidin-4-amine

Synthesis followed SP4, using 1.0 mmol 4-chloro-5-methylthieno[2,3-d]pyrimidine to give the title compound quantitatively, containing around 10% water even upon extensive drying in high vacuum.

1-(4,6-dimethylpyrimidin-2-yl)piperidin-4-amine

Synthesis followed SP4, using 1.8 mmol 2-chloro-4,6-dimethylpyrimidine to give the title compound upon purification by prep. HPLC (reversed phase) with 91% yield.

1-(thieno[3,2-d]pyrimidin-4-yl)piperidin-4-amine

Synthesis followed SP4, using 2.3 mmol 4-chlorothieno[3,2-d]pyrimidine. Upon cooling of the reaction mixture to 4° C., a solid formed which was filtered off and washed with EtOH to give the title compound as HCl-salt with 84% yield.

1-(2-methylthieno[2,3-d]pyrimidin-4-yl)piperidin-4-amine

Synthesis followed SP4, using 2.3 mmol 4-chloro-2-methylthieno[2,3-d]pyrimidine. Upon cooling of the reaction mixture to 4° C., a solid formed which was filtered off and washed with EtOH to give the title compound as HCl-salt with 90% yield.

Standard Protocol 5
(in analogy to WO 2004/043472, p. 32, 3$^{rd}$ paragraph)

Amination of 4-hydroxyquinazolines (or Its Tautomer)

4-Hydroxyquinazoline (1.0 eq.) was suspended in thionylchloride (2 mL/mmol), three catalytic drops of DMF were added and the mixture was heated to 80° C. for 4 h.

Thionylchloride was removed in vacuum, toluene (0.5 mL/mmol) was added and removed again under reduced pressure. The remaining solid was dried at high vacuum over night, taken up in ethylene glycol (3 mL/mmol) and treated with 4-(N-Boc-amino)piperidine (1.4 eq.) and DIEA (1.0 eq). The mixture was heated to 110° for 3 h.

For Boc-removal, 4 M HCl/dioxane (3 mL/mmol) was added under cooling (ice bath) and the mixture was stirred at r.t. for 2 h.

The solution was partitioned between 1.3 N aq. NaOH/brine (2:1, 20 mL/mmol) and CHCl$_3$ (4×10 mL/mmol). Combined organic phases were dried over MgSO$_4$ to give a yellow-brownish oily solid as crude product.

1-(5-phenylthieno[2,3-d]pyrimidin-4-yl)piperidin-4-amine

Synthesis followed SP5, using 2.3 mmol 5-phenyl-3H-thieno[2,3-d]pyrimidin-4-one or 5-phenyl-thieno[2,3-d]pyrimidin-4-ol to give the title compound quantitatively, containing around 25% water even upon extensive drying in high vacuum.

Nucleophilic Opening of Oxiranes and Final Functional Group Transformations:

Standard Protocol 6

(in analogy to, e.g., W. Yang et al., *Bioorg. Med. Chem. Lett.* 2005, 15, 1225; R. Howe et al., *J. Med. Chem.* 1992, 35, 1751)

Conversion of oxiranes into 1-aryloxy-2-propanol-3-amines

Oxirane (1.0 eq.) and amine (1.2 eq.) were dissolved in iPrOH (ca. 5 mL/mmol, if no solution was attained upon heating, DMSO was added dropwise until all material got dissolved) and heated to 80° C. for 3-70 h.

Standard Protocol 7

Deprotection of Silylated Phenols

Silylated compound (1.0 eq.) was dissolved in DMF (ca. 10 mL/mmol) and treated with KF (3.0 eq.) at r.t. for 3 h.

Standard Protocol 8

Deprotection of MOM-Protected Phenols

MOM-protected phenol (1.0 eq.) was dissolved in iPrOH (ca. 20 mL/mmol) and treated with p-toluenesulfonic acid monohydrate (1.1 eq.) at 60° C. for 6 h. The mixture was partitioned between aq. satd NaHCO$_3$ and CH$_2$Cl$_2$ (3×).

Standard Protocol 9

Benzylic Alcohols from Benzoic Esters

Ester compound (1.0 eq.) was dissolved in abs. CH$_2$Cl$_2$ (25 mL/mmol) and cooled to 0° C. LiAlH$_4$ (1.0 M in THF, 1.5 eq.) were added, and the solution stirred for 30 min at 0° C. If immediate LCMS-control indicated major amounts of starting material or intermediary aldehyde to be present, additional LiAlH$_4$ (1.0 M in THF, 1.0 eq.) was repeatedly added and stirring continued at 0° C. for 30 min each time. Reaction mixtures were quenched at 0° C. with H$_2$O (0.5 mL/mmol), 15% aq. NaOH (0.5 mL/mmol) and again H$_2$O (1.5 mL/mmol). The mixture was stirred for 15 min at r.t. and acidified with 1 N aq. HCl until any precipitate got dissolved. Product was isolated by prep. HPLC (reversed phase), partition of product fractions between half satd. NaHCO$_3$ and CH$_2$Cl$_2$ (3×) and final chromatography by prep. TLC (silica gel, CH$_2$Cl$_2$/MeOH 85:15).

Standard Protocol 10

Ester Saponification

Ester compound was dissolved in dioxane (10 mL/mmol) and treated with 3 N aq. NaOH (2.5 mL/mmol) at 110° C. for 2 h. Product was purified by prep. HPLC (reversed phase).

Standard Protocol 11

N-Methylation of Aliphatic Amines

Secondary amine was dissolved in CH$_2$Cl$_2$ (0.1 mL/50 μmol), CH$_3$CN (0.7 mL/50 μmol), DIEA (2.0 eq.) and iodomethane (2.0 eq) were added, and the mixture stirred at 85° C. for 5-22 h. Purification was performed by prep. TLC (1 mm silica gel, PE/CH$_2$Cl$_2$/MeOH 4:6:1).

Standard Protocol 12

Transformation of Aryl Methylethers into Phenols

Aryl methyl ether (1.0 eq.) was dissolved in CH$_2$Cl$_2$ (ca. 20 mL/mmol) and treated with BBr$_3$ (1.2 eq. per methyl group to be removed) at 0° C. for 1-4 h. The mixture was partitioned between aq. 5% NaHCO$_3$ and CH$_2$Cl$_2$ (3×). Purification was performed by prep. TLC (1 mm silica gel, PE/CH$_2$Cl$_2$/MeOH 4:6:1).

Devices Used:

Analytical LC/ESI-MS: Waters 2700 Autosampler. Waters 600 Multisolvent Delivery System, Waters 600 Controller. 20 μL sample loop. Column, Onyx Monolithic C18 (Phenomenex), 50×4.6 mm, with stainless steel 2 μm prefilter. Eluent A, H$_2$O+0.1% HCO$_2$H; eluent B, MeCN. Gradient, 2% B to 100% B within 4 min (flow, 3 mL/min), then isocratic for 0.90 min (flow, 4 mL/min), then back to 2% B within 0.15 min (flow, 4 mL/min), then isocratic for 0.50 min (flow, 4 mL/min). Micromass LCZ single quadrupol mass spectrometer with electrospray source. MS method, MS5_30 minPM-80-800-25V; positive/negative ion mode scanning, m/z 80-800 or 80-900 in 1.3 s; capillary, 3.5 kV; cone voltage, 25 V; multiplier voltage, 500 V; probe and desolvation gas temperature, 120° C. and 350° C., respectively. Waters 2487 Dual λAbsorbance Detector, set to 254 nm. Software, Waters Masslynx V 4.0.

Preparative TLC: Merck PLC plates, silica gel 60 F$_{254}$, 0.5 mm, 1.0 mm or 2.0 mm.

Flash chromatography: Acros silica gel 60A, 0.035-0.070 mm. Flash Master Personal or Flash Master II, Jones Chromatography, UK.

Preparative HPLC-MS: Waters 2700 Autosampler, Waters 600 Multisolvent Delivery System with preparative pump heads, Waters 600 Controller, 5000 μL Sample loop. At-column dilution: Waters 600 Multisolvent Delivery System with analytical pump heads; Waters 600 Controller; solvent, MeCN-MeOH 80:20 (v/v); flow rate, 0.20 or is 1 mL/min. Column, Waters X-Terra RP18, 7 μm, 19×150 mm with X-Terra RP18 guard cartridge 7 μm, 19×10 mm, used at flow rate 20 mL/min. Eluent A, H$_2$O containing 0.1% (v/v) HCO$_2$H or H$_2$O containing 0.1% (v/v) NEt$_3$; eluent B, MeCN. Different linear gradients, individually adapted to sample. Injection volume, 0.5 mL-5 mL, depending on sample. Make-up solvent, MeOH-MeCN—H$_2$O—HCO$_2$H 80:15:4.95:0.05 (v/v/v/v). Make-up pump, Waters Reagent Manager, flow rate 0.5 mL/min. Waters ZQ single quadrupol mass spectrometer with electrospray source. Positive or negative ion mode scanning m/z 105-950 in 1 s; capillary, 4 kV; cone voltage, 20 V; multiplier voltage, 600 V; probe and desolvation gas temperature, 120° C. and 250° C., respectively. Waters Fraction Collector II with mass-triggered fraction collection. Waters 2487 Dual λAbsorbance Detector, set to 254 nm. Software, Waters Masslynx V4.0.

Examples

Example 1

4-(2-hydroxy-3-(1-(5-phenylthieno[2,3-d]pyrimidin-4-yl)piperidin-4-ylamino)propoxy)phenol

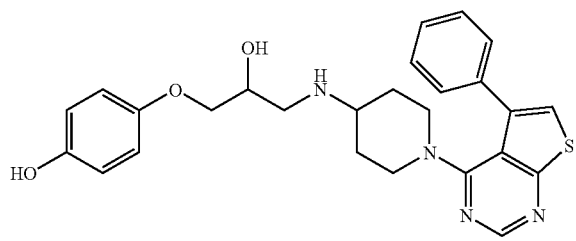

Synthesis followed SP6 (3 h), using 220 μmol tert-butyldimethyl(4-(oxiran-2-ylmethoxy)phenoxy)silane and 1-(5-phenylthieno[2,3-d]pyrimidin-4-yl)piperidin-4-amine to give O-silylated intermediate upon purification by prep. HPLC (reversed phase) with 21% yield. Product was obtained by deprotection according to SP7 and purification by prep. HPLC (reversed phase) with 70% yield.

Example 2

(R)-4-(2-hydroxy-3-(1-(5-phenylthieno[2,3-d]pyrimidin-4-yl)piperidin-4-ylamino)propoxy)phenol

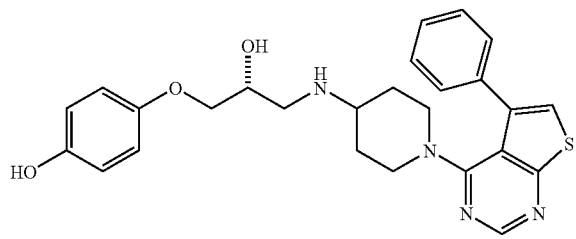

Synthesis followed SP6 (4 h), using 250 μmol (R)-2-((4-(methoxymethoxy)phenoxy)methyl)oxirane and 1-(5-phenylthieno[2,3-d]pyrimidin-4-yl)piperidin-4-amine to give O-MOM intermediate upon purification by prep. TLC (2 mm silica gel, PE/CH$_2$Cl$_2$/MeOH 4:6:1) with 57% yield. Product was obtained by MOM removal according to SP8 (1.5 eq. TosOH, 10 h) and purification by prep. TLC (1 mm silica gel, CH$_2$Cl$_2$/MeOH 90:10) with 55% yield.

Example 3

(S)-4-(2-hydroxy-3-(1-(5-phenylthieno[2,3-d]pyrimidin-4-yl)piperidin-4-ylamino)propoxy)phenol

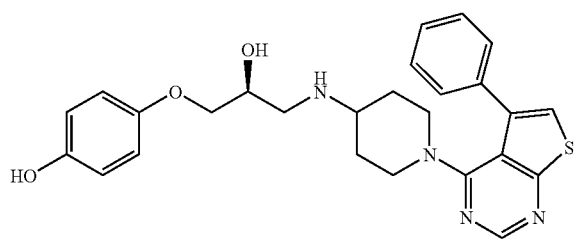

Synthesis followed SP6 (4 h), using 250 μmol (S)-2-((4-(methoxymethoxy)phenoxy)methyl)oxirane and 1-(5-phenylthieno[2,3-d]pyrimidin-4-yl)piperidin-4-amine to give O-MOM intermediate upon purification by prep. TLC (2 mm silica gel, PE/CH$_2$Cl$_2$/MeOH 4:6:1) with 58% yield. Product was obtained by MOM removal according to SP8 (1.5 eq. TosOH, 10 h) and purification by prep. TLC (1 mm silica gel, CH$_2$Cl$_2$/MeOH 90:10) with 61% yield.

Example 4

4-(2-hydroxy-3-(1-(5-methylthieno[2,3-d]pyrimidin-4-yl)piperidin-4-ylamino)propoxy)phenol

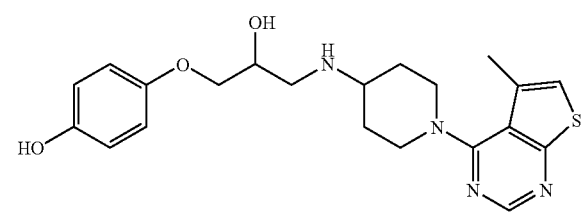

Synthesis followed SP6 (3 h), using 150 μmol tert-butyldimethyl(4-(oxiran-2-ylmethoxy)phenoxy)silane and 1-(5-methylthieno[2,3-d]pyrimidin-4-yl)piperidin-4-amine to give O-silylated intermediate upon purification by prep. HPLC (reversed phase) with 11% yield. Product was obtained by deprotection according to SP7 and purification by prep. HPLC (reversed phase) with 76% yield.

Example 5

4-(2-hydroxy-3-(1-(2-methylthieno[2,3-d]pyrimidin-4-yl)piperidin-4-ylamino)propoxy)phenol

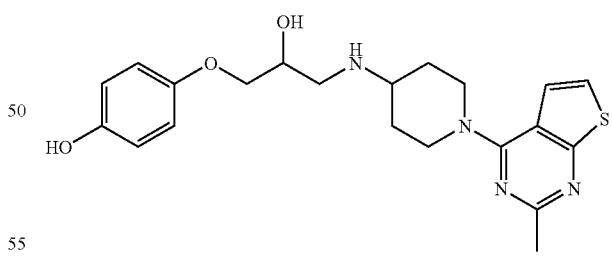

Synthesis followed SP6 (iPrOH:DMSO 1:1, 1.2 eq. DIEA, 120° C., 48 h), using 200 μmol tert-butyldimethyl(4-(oxiran-2-ylmethoxy)phenoxy)silane and 1-(2-methylthieno[2,3-d]pyrimidin-4-yl)piperidin-4-amine HCl-salt to give O-silylated intermediate upon purification by prep. HPLC (reversed phase) and prep. TLC (1 mm silica gel, PE/CH$_2$Cl$_2$/MeOH 6:4:1) with 22% yield. Product was obtained by deprotection according to SP7 and purification by prep. HPLC (reversed phase) and prep. TLC (1 mm silica gel, PE/CH$_2$Cl$_2$/MeOH 3:7:1.5) with 25% yield.

Example 6

4-(2-hydroxy-3-(1-(5-methyl-6-phenylthieno[2,3-d]pyrimidin-4-yl)piperidin-4-ylamino)propoxy)phenol

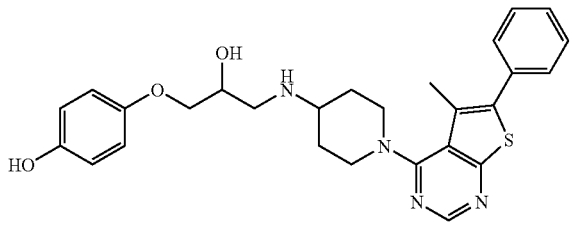

Synthesis followed SP6 (3 h), using 150 μmol tert-butyldimethyl(4-(oxiran-2-ylmethoxy)phenoxy)silane and 1-(5-methyl-6-phenylthieno[2,3-d]pyrimidin-4-yl)piperidin-4-amine to give O-silylated intermediate upon purification by prep. HPLC (reversed phase) with 17% yield. Product was obtained by deprotection according to SP7 and purification by prep. HPLC (reversed phase) with 14% yield.

Example 7

4-(2-hydroxy-3-(1-(thieno[3,2-d]pyrimidin-4-yl)piperidin-4-ylamino)propoxy)phenol

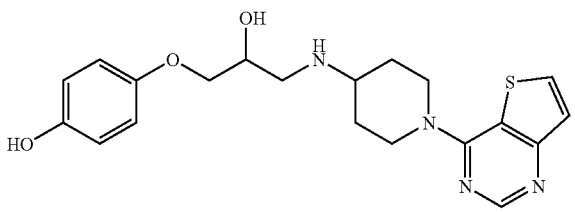

Synthesis followed SP6 (iPrOH:DMSO 1:1, 1.2 eq. DIEA, 120° C., 48 h), using 200 μmol tert-butyldimethyl(4-(oxiran-2-ylmethoxy)phenoxy)silane and 1-(thieno[3,2-d]pyrimidin-4-yl)piperidin-4-amine HCl-salt to give O-silylated intermediate upon purification by prep. HPLC (reversed phase) and prep. TLC (1 mm silica gel, PE/CH$_2$Cl$_2$/MeOH 6:4:1) with 13% yield. Product was obtained by deprotection according to SP7 and purification by prep. HPLC (reversed phase) with 37% yield.

Example 8

4-(3-(1-(4,6-dimethylpyrimidin-2-yl)piperidin-4-ylamino)-2-hydroxypropoxy)phenol

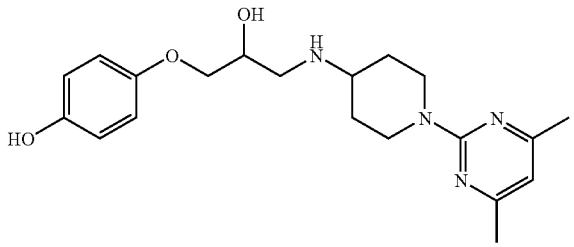

Synthesis followed SP6 (iPrOH:DMSO 1:1, 120° C., 35 h), using 200 μmol tert-butyldimethyl(4-(oxiran-2-ylmethoxy)phenoxy)silane and 1-(4,6-dimethylpyrimidin-2-yl)piperidin-4-amine to give O-silylated intermediate upon purification by prep. HPLC (reversed phase) and prep. TLC (1 mm silica gel, PE/CH$_2$Cl$_2$/MeOH 6:4:1) with 64% yield. Product was obtained by deprotection according to SP7 and purification by prep. HPLC (reversed phase) and prep. TLC (1 mm silica gel, PE/CH$_2$Cl$_2$/MeOH 3:7:1.5) with 10% yield.

Example 9

4-(2-hydroxy-3-(1-(5-(thiophen-2-yl)thieno[2,3-d]pyrimidin-4-yl)piperidin-4-ylamino)propoxy)phenol

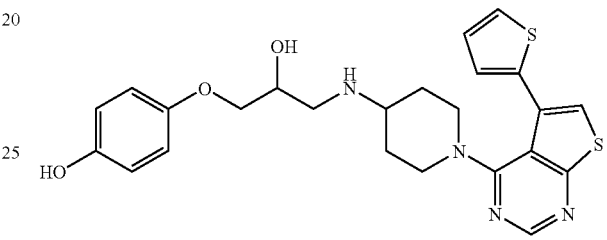

Synthesis followed SP6 (5 h), using 150 μmol tert-butyldimethyl(4-(oxiran-2-ylmethoxy)phenoxy)silane and 1-(5-(2-thienyl)thieno[2,3-d]pyrimidin-4-yl)piperidin-4-amine to give O-silylated intermediate upon purification by prep. HPLC (reversed phase) and prep. TLC (1 mm silica gel, CH$_2$Cl$_2$MeOH 95:5) with 27% yield. Product was obtained by deprotection according to SP7 and purification by prep. HPLC (reversed phase) with 27% yield.

Example 10

4-(3-(1-(5-(4-fluorophenyl)thieno[2,3-d]pyrimidin-4-yl)piperidin-4-ylamino)-2-hydroxypropoxy)phenol

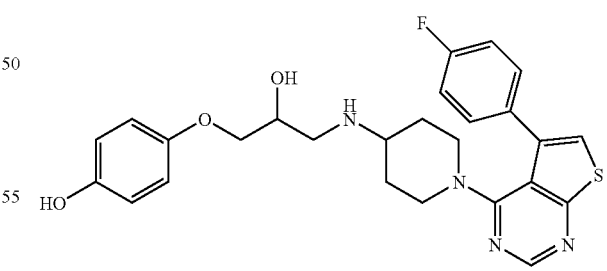

Synthesis followed SP6 (iPrOH:DMSO 1:1, 10 h), using 200 μmol tert-butyldimethyl(4-(oxiran-2-ylmethoxy)phenoxy)silane and 1-(5-(4-fluorophenyl)thieno[2,3-d]pyrimidin-4-yl)piperidin-4-amine to give O-silylated intermediate upon purification by prep. HPLC (reversed phase) with 45% yield. Product was obtained by deprotection according to SP7 and purification by prep. HPLC (reversed phase) with 74% yield.

Example 11

4-(3-((1-(5-(4-fluorophenyl)thieno[2,3-d]pyrimidin-4-yl)piperidin-4-yl)(methyl)amino)-2-hydroxypropoxy)phenol

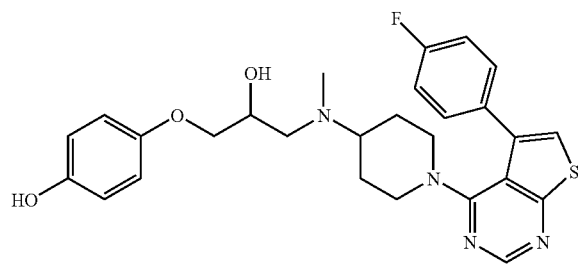

Product of example 10 (60 μmol) was converted into the title compound with 32% yield following SP11 (5 h).

Example 12 ethyl 2-hydroxy-5-(2-hydroxy-3-(1-(5-phenylthieno[2,3-d]pyrimidin-4-yl piperidin-4-ylamino)propoxy)benzoate

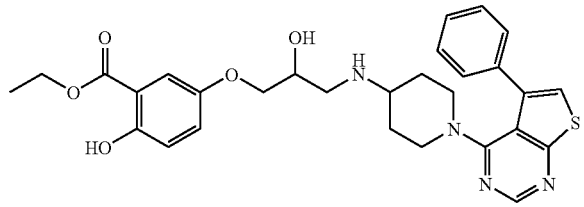

Synthesis followed SP6 (10 h), using 250 μmol ethyl 2-hydroxy-5-(oxiran-2-ylmethoxy)benzoate and 1-(5-phenylthieno[2,3-d]pyrimidin-4-yl)piperidin-4-amine to give benzoic ester intermediate upon purification by prep. TLC (2 mm silica gel, PE/CH$_2$Cl$_2$/MeOH 4:6:1) with 51% yield.

Example 13

4-(2-hydroxy-3-(1-(5-phenylthieno[2,3-d]pyrimidin-4-yl)piperidin-4-ylamino)propoxy)-2-(hydroxymethyl)phenol

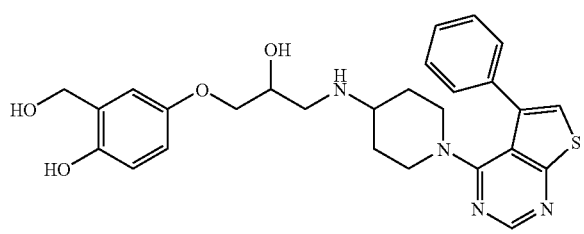

Product was obtained by ester reduction of example 12 according to SP9 (1.5 eq. LiAlH$_4$) with 39% yield.

Example 14

4-(2-hydroxy-3-(1-(5-phenyl-1,2-dihydrothieno[2,3-d]pyrimidin-4-yl)piperidin-4-ylamino)propoxy)-2-(hydroxymethyl)phenol

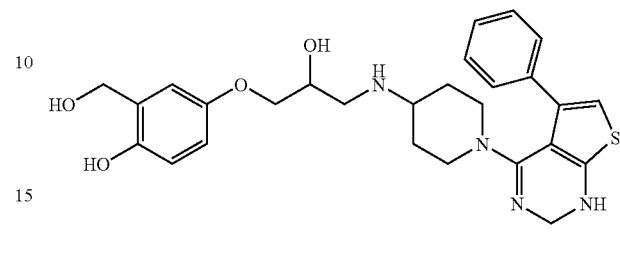

Product was obtained by ester reduction of example 12 according to SP9 with 19% yield using a larger excess of LiAlH$_4$ (4.0 eq.) and additional stirring at r.t. for 3 h.

Example 15

4-(2-hydroxy-3-(1-(5-phenylthieno[2,3-d]pyrimidin-4-yl)piperidin-4-ylamino)propoxy)-2-(methoxymethyl)phenol

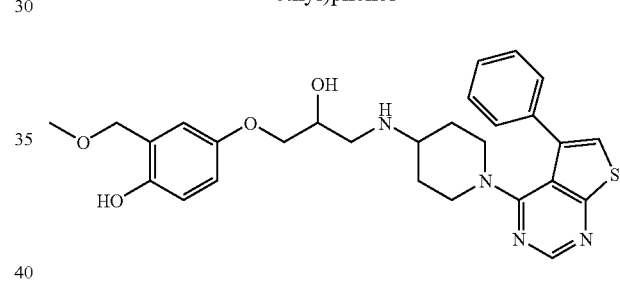

Example 13 (50 μmol) was dissolved in MeOH (1 mL) and treated with concd HCl (0.1 mL) at r.t. for 6 h. The mixture was partitioned between aq. satd NaHCO$_3$ and CH$_2$Cl$_2$ (3×) and purified by prep. TLC (1 mm silica gel, PE/CH$_2$Cl$_2$/MeOH 2:6:2) to give the title compound with 15% yield.

Example 16

2-hydroxy-5-(2-hydroxy-3-(1-(5-phenylthieno[2,3-d]pyrimidin-4-yl)piperidin-4-ylamino)propoxy)benzoic acid

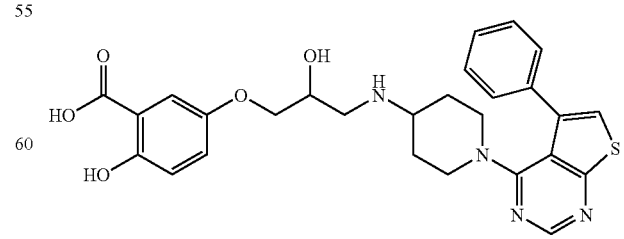

Product was obtained by ester saponification of example 12 (30 μmol) according to SP10 with 68% yield.

Example 17 ethyl 2-hydroxy-5-(2-hydroxy-3-(1-(5-methylthieno[2,3-d]pyrimidin-4-yl)piperidin-4-ylamino)propoxy)benzoate

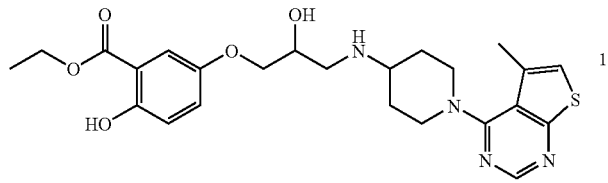

Synthesis followed SP6 (6 h), using 170 μmol ethyl 2-hydroxy-5-(oxiran-2-ylmethoxy)benzoate and 1-(5-methylthieno[2,3-d]pyrimidin-4-yl)piperidin-4-amine to give benzoic ester intermediate upon purification by prep. HPLC (reversed phase) with 23% yield.

Example 18

4-(2-hydroxy-3-(1-(5-methylthieno[2,3-d]pyrimidin-4-yl)piperidin-4-ylamino)propoxy)-2-(hydroxymethyl)phenol

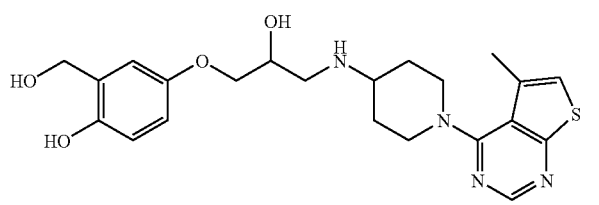

Product was obtained by ester reduction of example 17 according to SP9 (total 3.5 eq. LiAlH$_4$) with 25% yield.

Example 19

4-(2-hydroxy-3-(1-(2-methylthieno[2,3-d]pyrimidin-4-yl)piperidin-4-ylamino)propoxy)-2-(hydroxymethyl)phenol

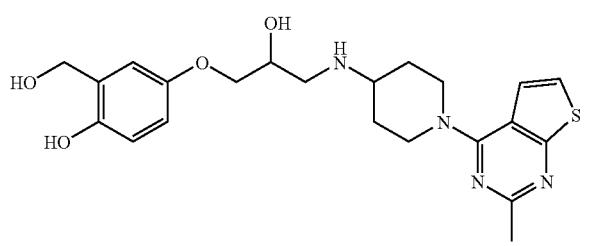

Synthesis followed SP6 (IPrOH:DMSO:H$_2$O 4:2:1, 1.2 eq. DIEA, 16 h), using 290 μmol ethyl 2-hydroxy-5-(oxiran-2-ylmethoxy)benzoate and 1-(2-methylthieno[2,3-d]pyrimidin-4-yl)piperidin-4-amine HCl-salt to give benzoic ester intermediate upon purification by prep. TLC (1 mm silica gel, PE/CH$_2$Cl$_2$/MeOH 4:6:1) with 20% yield. Product was obtained by ester reduction according to SP9 (total 2.5 eq. LiAlH$_4$) with 16% yield.

Example 20 ethyl 2-hydroxy-5-(2-hydroxy-3-(1-(5-methyl-6-phenylthieno[2,3-d]pyrimidin-4-yl)piperidin-4-ylamino)propoxy)benzoate

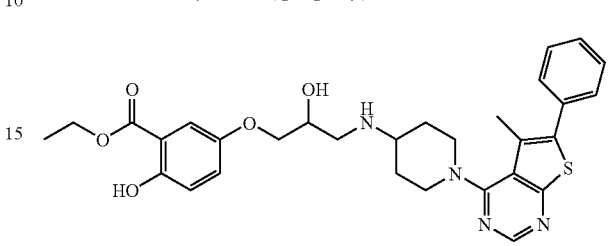

Synthesis followed SP6 (16 h), using 200 μmol ethyl 2-hydroxy-5-(oxiran-2-ylmethoxy)benzoate and 1-(5-methyl-6-phenylthieno[2,3-d]pyrimidin-4-yl)piperidin-4-amine to give benzoic ester intermediate upon purification by prep. TLC (1 mm silica gel, PE/CH$_2$Cl$_2$/MeOH 4:6:1) with 24% yield.

Example 21

4-(2-hydroxy-3-(1-(5-methyl-6-phenylthieno[2,3-d]pyrimidin-4-yl)piperidin-4-ylamino)propoxy)-2-(hydroxymethyl)phenol

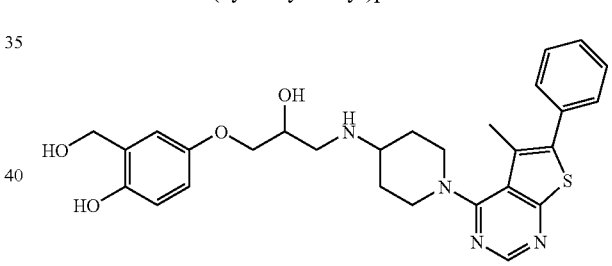

Product was obtained by ester reduction of example 20 according to SP9 (total 2.5 eq. LiAlH$_4$) with 5% yield.

Example 22 ethyl 2-hydroxy-5-(2-hydroxy-3-(1-(thieno[3,2-d]pyrimidin-4-yl)piperidin-4-ylamino)propoxy)benzoate

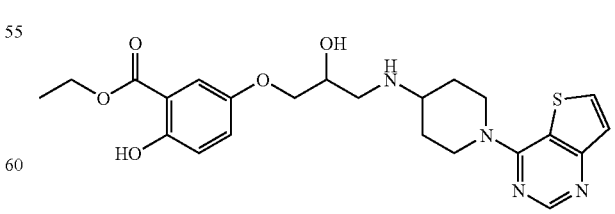

Synthesis followed SP6 (IPrOH:DMSO:H$_2$O 4:2:1, 1.2 eq. DIEA, 70 h), using 330 μmol ethyl 2-hydroxy-5-(oxiran-2-ylmethoxy)benzoate and 1-(thieno[3,2-d]pyrimidin-4-yl)piperidin-4-amine HCl-salt to give benzoic ester intermediate upon purification by prep. HPLC (reversed phase) and prep. TLC (1 mm silica gel, PE/CH$_2$Cl$_2$/MeOH 4:6:1) with 30% yield.

Example 23

4-(2-hydroxy-3-(1-(thieno[3,2-d]pyrimidin-4-yl)piperidin-4-ylamino)propoxy)-2-(hydroxymethyl)phenol

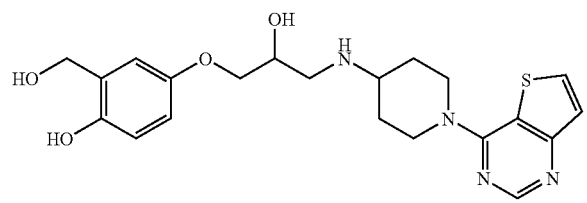

Product was obtained by ester reduction of example 22 according to SP9 (total 3.5 eq. LiAlH$_4$) with 21% yield.

Example 24

4-(3-(1-(4,6-dimethylpyrimidin-2-yl)piperidin-4-ylamino)-2-hydroxypropoxy)-2-(hydroxymethyl)phenol

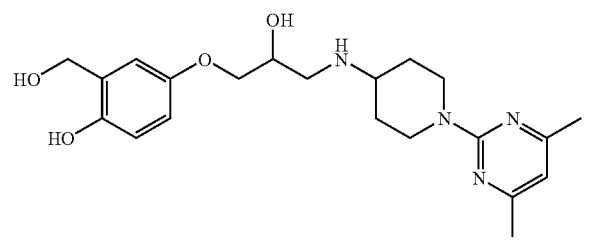

Synthesis followed SP6 (iPrOH:DMSO:H$_2$O 2:1:1, 24 h at 80° C., 24 h at 110° C.), using 250 µmol ethyl 2-hydroxy-5-(oxiran-2-ylmethoxy)benzoate and 1-(4,6-dimethylpyrimidin-2-yl)piperidin-4-amine to give benzoic ester intermediate upon partition between half satd. aq. NaHCO$_3$ and CH$_2$Cl$_2$ (3×) and purification by prep. TLC (1 mm silica gel, PE/CH$_2$Cl$_2$/MeOH 4:6:1) with 54% yield. Product was obtained by ester reduction according to SP9 (total 3.0 eq. LiAlH$_4$) with 8% yield.

Example 25 ethyl 2-hydroxy-5-(2-hydroxy-3-(1-(5-(thiophen-2-yl)thieno[2,3-d]pyrimidin-4-yl)piperidin-4-ylamino)propoxy)benzoate

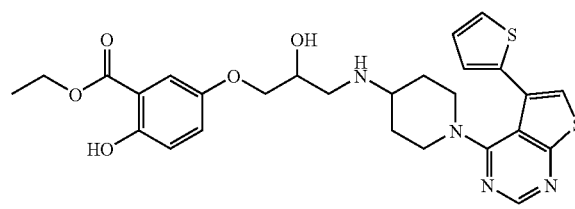

Synthesis followed SP6 (16 h), using 290 µmol ethyl 2-hydroxy-5-(oxiran-2-ylmethoxy)benzoate and 1-(5-(2-thienyl)thieno[2,3-d]pyrimidin-4-yl)piperidin-4-amine to give benzoic ester intermediate upon purification by prep. TLC (1 mm silica gel, PE/CH$_2$Cl$_2$/MeOH 4:6:1) with 22% yield.

Example 26

4-(2-hydroxy-3-(1-(5-(thiophen-2-yl)thieno[2,3-d]pyrimidin-4-yl)piperidin-4-ylamino)propoxy)-2-(hydroxymethyl)phenol

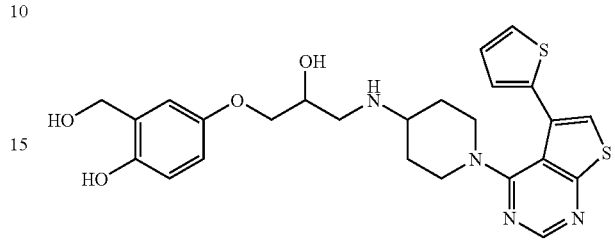

Product was obtained by ester reduction of example 25 according to SP9 (total 2.5 eq. LiAlH$_4$) with 10% yield.

Example 27

3-(2-Hydroxy-3-(1-(5-phenyl-thieno[2,3-d]pyrimidin-4-yl)-piperidin-4-ylamino)-propoxy)-phenol

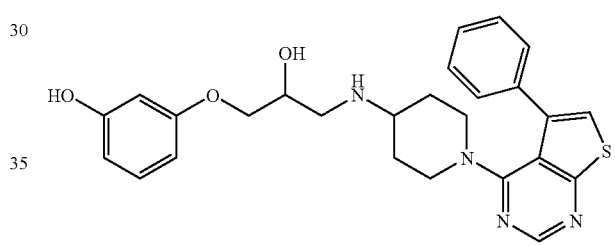

Synthesis followed SP6 (iPrOH:DMSO 3:1, 24 h), using 150 µmol 3-(oxiran-2-ylmethoxy)phenyl benzoate and 1-(5-phenylthieno[2,3-d]pyrimidin-4-yl)piperidin-4-amine. The benzoic acid moiety was already lost during purification by prep. TLC (1 mm silica gel, PE/CH$_2$Cl$_2$/MeOH 4:6:1) and subsequent prep. HPLC (reversed phase) to give the title compound with 20% yield.

Example 28 methyl 2-hydroxy-4-(2-hydroxy-3-(1-(5-phenylthieno[2,3-d]pyrimidin-4-yl)piperidin-4-ylamino)propoxy)benzoate

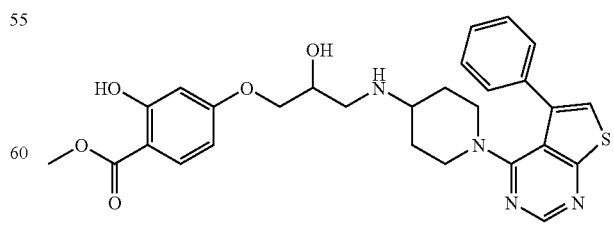

Synthesis followed SP6 (4 h), using 220 µmol methyl 2-hydroxy-4-(oxiran-2-ylmethoxy)benzoate and 1-(5-phenylthieno[2,3-d]pyrimidin-4-yl)piperidin-4-amine to give benzoic ester intermediate upon purification by prep. TLC (1 mm silica gel, PE/CH₂C₂/MeOH 4:6:1) with 70% yield.

Example 29

5-(2-hydroxy-3-(1-(5-phenylthieno[2,3-d]pyrimidin-4-yl)piperidin-4-ylamino)propoxy)-2-(hydroxymethyl)phenol

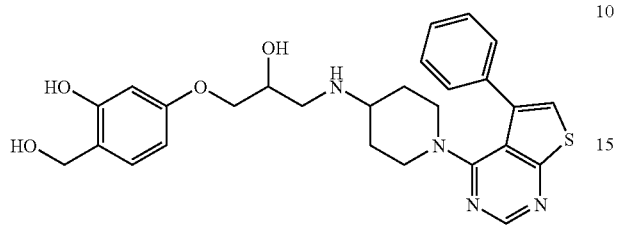

Product was obtained by ester reduction of example 28 according to SP9 (total 4.5 eq. LiAlH₄) with 11% yield.

Example 30

3-ethyl-4-(2-hydroxy-3-(1-(5-phenylthieno[2,3-d]pyrimidin-4-yl)piperidin-4-ylamino)propoxy)phenol

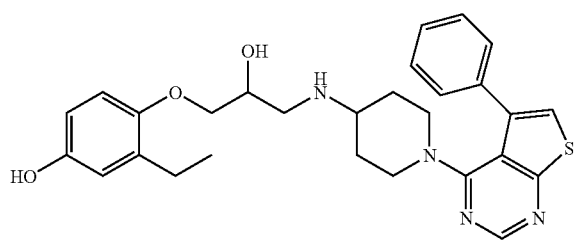

Synthesis followed SP6 (6 h), using 200 μmol 2-((4-(adamantane-1-carbonyloxy)-2-ethylphenoxy)methyl)oxirane and 1-(5-phenylthieno[2,3-d]pyrimidin-4-yl)piperidin-4-amine to give ester intermediate upon purification by prep. TLC (1 mm silica gel, PE/CH₂Cl₂/MeOH 60:70:15) with 48% yield. Product was obtained by ester saponification according to SP10 (3 h, 80° C.) with 46% yield upon following workup: the mixture was partitioned between aq. 1.3 N NaOH/brine (1:1) and CHCl₃ (2×) and ethyl acetate (1×). Purification was performed by prep. TLC (1 mm silica gel, PE/CH₂Cl₂/MeOH 60:90:15).

Example 31

2-ethyl-4-(2-hydroxy-3-(1-(5-phenylthieno[2,3-d]pyrimidin-4-yl)piperidin-4-ylamino)propoxy)phenol

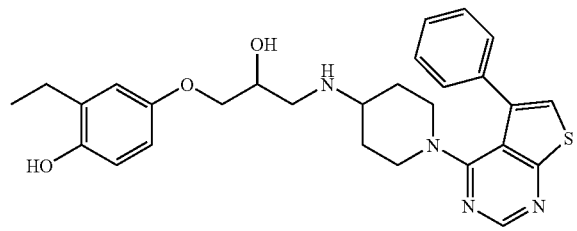

Synthesis followed SP6 (10 h), using 200 μmol 2-((4-(adamantane-1-carbonyloxy)-2-ethylphenoxy)methyl)oxirane and 1-(5-phenylthieno[2,3-d]pyrimidin-4-yl)piperidin-4-amine to give MOM intermediate upon purification by prep. TLC (1 mm silica gel, PE/CH₂Cl₂/MeOH 4:6:1) with 10% yield. Product was obtained by MOM-removal according to SP8 with 54% yield upon purification by prep. TLC (1 mm silica gel, PE/CH₂Cl₂/MeOH 8:4:1).

Example 32 ethyl 5-hydroxy-2-(2-hydroxy-3-(1-(5-phenylthieno[2,3-d]pyrimidin-4-yl)piperidin-4-ylamino)propoxy)benzoate

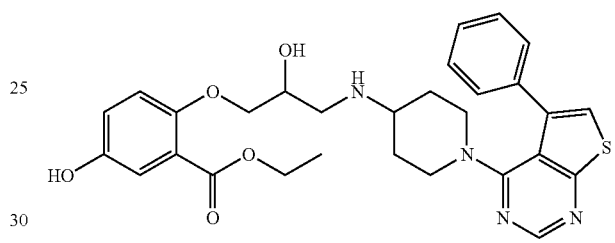

Synthesis followed SP6 (6 h), using 250 μmol ethyl 5-(methoxymethoxy)-2-(oxiran-2-ylmethoxy)benzoate and 1-(5-phenylthieno[2,3-d]pyrimidin-4-yl)piperidin-4-amine to give MOM intermediate upon purification by prep. TLC (2 mm silica gel, PE/CH₂Cl₂/MeOH 4:6:1) with 48% yield. Product was obtained by MOM-removal according to SP8 with 32% yield upon purification by prep. TLC (1 mm silica gel, PE/CH₂Cl₂/MeOH 2:5:1).

Example 33

4-(2-hydroxy-3-(1-(5-phenylthieno[2,3-d]pyrimidin-4-yl)piperidin-4-ylamino-propoxy)-3-(hydroxymethyl)phenol

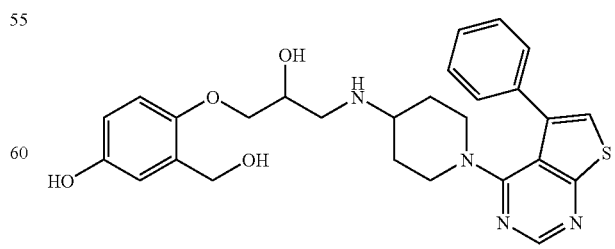

Product was obtained by ester reduction of example 32 according to SP9 (1.5 eq. LiAlH₄) with 17% yield.

Example 34 methyl 4-hydroxy-2-(2-hydroxy-3-(1-(5-phenylthieno[2,3-d]pyrimidin-4-yl)piperidin-4-ylamino)propoxy)benzoate

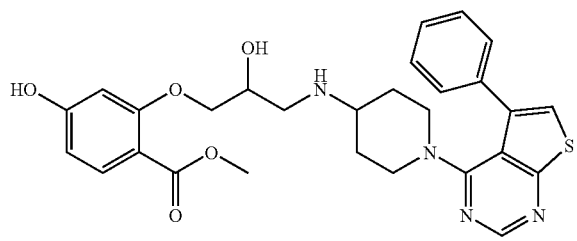

Synthesis followed SP6 (3 h), using 300 μmol methyl 4-(methoxymethoxy)-2-(oxiran-2-ylmethoxy)benzoate and 1-(5-phenylthieno[2,3-d]pyrimidin-4-yl)piperidin-4-amine to give MOM intermediate upon purification by prep. TLC (1 mm silica gel, PE/CH$_2$Cl$_2$/MeOH 10:6:1) with 51% yield. Product was obtained by MOM-removal according to SP8 with 32% yield upon purification by prep. TLC (1 mm silica gel, PE/CH$_2$Cl$_2$/MeOH 6:4:1) and subsequent prep. HPLC (reversed phase).

Example 35

4-hydroxy-2-(2-hydroxy-3-(1-(5-phenylthieno[2,3-d]pyrimidin-4-yl)piperidin-4-ylamino)propoxy)benzoic acid

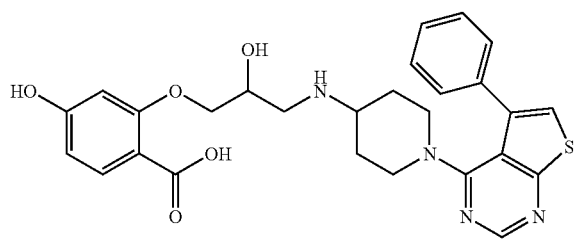

Product was obtained by ester saponification of example 34 (100 μmol) according to SP10 with 72% yield.

Example 36

1-(3-(hydroxymethyl)phenoxy)-3-(1-(5-phenylthieno[2,3-d]pyrimidin-4-yl)piperidin-4-ylamino)propan-2-ol

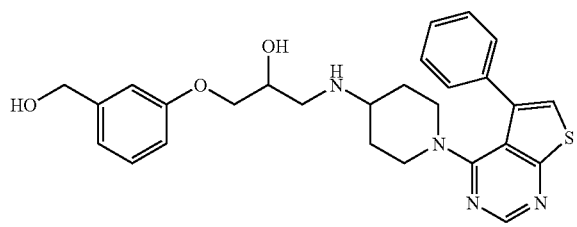

Synthesis followed SP6 (4 h), using 150 μmol (3-(oxiran-2-ylmethoxy)phenyl)methanol and 1-(5-phenylthieno[2,3-d]pyrimidin-4-yl)piperidin-4-amine to give the title compound with 64% yield upon purification by prep. HPLC (reversed phase).

Example 37

1-(3-(hydroxymethyl)phenoxy)-3-(1-(5-methylthieno[2,3-d]pyrimidin-4-yl)piperidin-4-ylamino)propan-2-ol

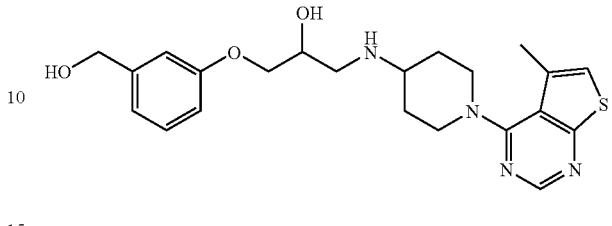

Synthesis followed SP6 (iPrOH:DMSO 1:1, 30 h at 80° C. and 20 h at 100° C.), using 220 μmol (3-(oxiran-2-ylmethoxy)phenyl)methanol and 1-(5-methylthieno[2,3-d]pyrimidin-4-yl)piperidin-4-amine to give the title compound with 26% yield upon purification by prep. HPLC (reversed phase) and subsequent by prep. TLC (1 mm silica gel, PE/CH$_2$Cl$_2$/MeOH 4:6:1).

Example 38

1-(3-(hydroxymethyl)phenoxy)-3-(1-(2-methylthieno[2,3-d]pyrimidin-4-yl)piperidin-4-ylamino)propan-2-ol

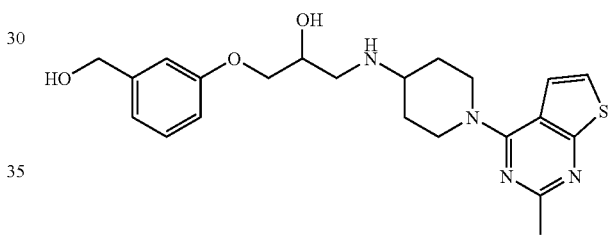

Synthesis followed SP6 (iPrOH:DMSO 1:1, 1.2 eq. DIEA, 120° C., 90 h), using 150 μmol (3-(oxiran-2-ylmethoxy)phenyl)methanol and 1-(2-methylthieno[2,3-d]pyrimidin-4-yl)piperidin-4-amine HCl-salt to give the title compound with 20% yield upon purification by prep. HPLC (reversed phase) and subsequent by prep. TLC (1 mm silica gel, PE/CH$_2$Cl$_2$/MeOH 4:6:1).

Example 39

1-(3-(hydroxymethyl)phenoxy)-3-(1-(5-methyl-6-phenylthieno[2,3-d]pyrimidin-4-yl)piperidin-4-ylamino)propan-2-ol

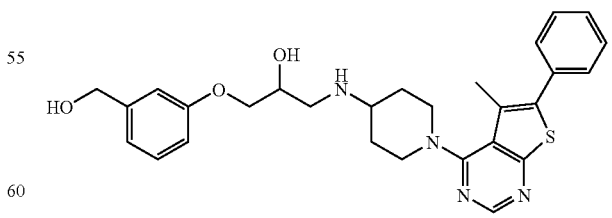

Synthesis followed SP6 (iPrOH:DMSO 1:1, 35 h), using 150 μmol (3-(oxiran-2-ylmethoxy)phenyl)methanol and 1-(5-methyl-6-phenylthieno[2,3-d]pyrimidin-4-yl)piperidin-4-amine to give the title compound with 36% yield upon purification by prep. HPLC (reversed phase).

Example 40

1-(1-(5-(4-fluorophenyl)thieno[2,3-d]pyrimidin-4-yl)piperidin-4-ylamino)-3-(3-(hydroxymethyl)phenoxy)propan-2-ol

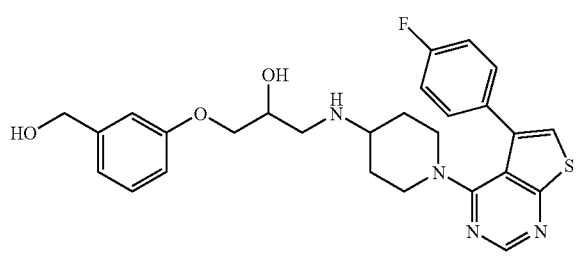

Synthesis followed SP6 (iPrOH:DMSO 1:1, 14 h), using 150 µmol (3-(oxiran-2-ylmethoxy)phenyl)methanol and 1-(5-(4-fluorophenyl)thieno[2,3-d]pyrimidin-4-yl)piperidin-4-amine to give the title compound with 35% yield upon purification by prep. HPLC (reversed phase).

Example 41

1-(3-(hydroxymethyl)phenoxy)-3-(methyl(1-(5-phenylthieno[2,3-d]pyrimidin-4-yl)piperidin-4-yl)amino)propan-2-ol

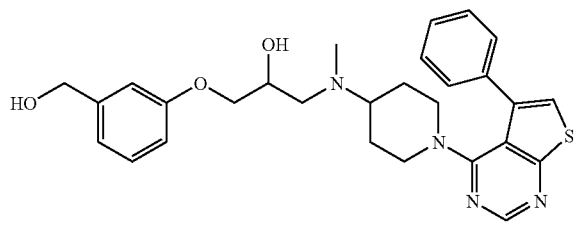

Product of example 36 (80 µmol) was converted into the title compound with 18% yield following SP11 (10 h).

Example 42

1-(3-(hydroxymethyl)phenoxy)-3-(methyl(1-(5-methyl-6-phenylthieno[2,3-d]pyrimidin-4-yl)piperidin-4-yl)amino)propan-2-ol

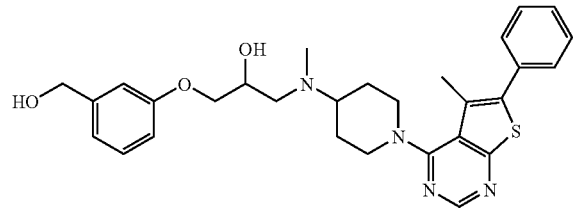

Product of example 39 (50 µmol) was converted into the title compound with 34% yield following SP11 (22 h).

Example 43

1-(4-(hydroxymethyl)phenoxy)-3-(1-(5-phenylthieno[2,3-d]pyrimidin-4-yl)piperidin-4-ylamino)propan-2-ol

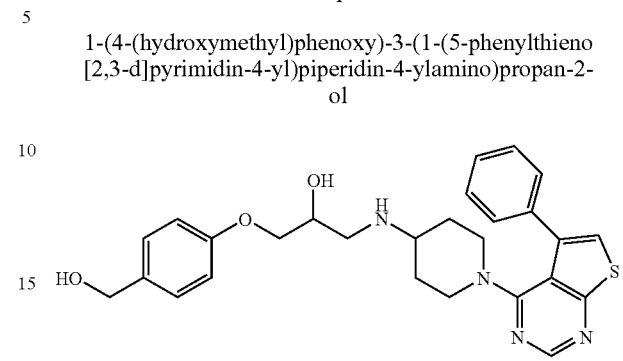

Synthesis followed SP6 (4 h), using 120 µmol (4-(oxiran-2-ylmethoxy)phenyl)methanol and 1-(5-phenylthieno[2,3-d]pyrimidin-4-yl)piperidin-4-amine to give the title compound with 19% yield upon purification by prep. HPLC (reversed phase).

Example 44

1-(1-(5-(4-fluorophenyl)thieno[2,3-d]pyrimidin-4-yl)piperidin-4-ylamino)-3-(4-(hydroxymethyl)phenoxy)propan-2-ol

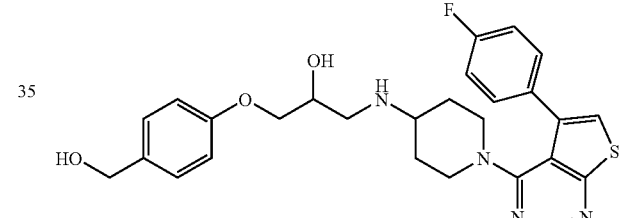

Synthesis followed SP6 (iPrOH:DMSO 1:1, 12 h), using 150 µmol (4-(oxiran-2-ylmethoxy)phenyl)methanol and 1-(5-(4-fluorophenyl)thieno[2,3-d]pyrimidin-4-yl)piperidin-4-amine to give the title compound with 29% yield upon purification by prep. HPLC (reversed phase) and subsequent by prep. TLC (1 mm silica gel, PE/CH$_2$Cl$_2$/MeOH 4:6:1).

Example 45

2,3-difluoro-4-(2-hydroxy-3-(1-(5-phenylthieno[2,3-d]pyrimidin-4-yl)piperidin-4-ylamino)propoxy)phenol

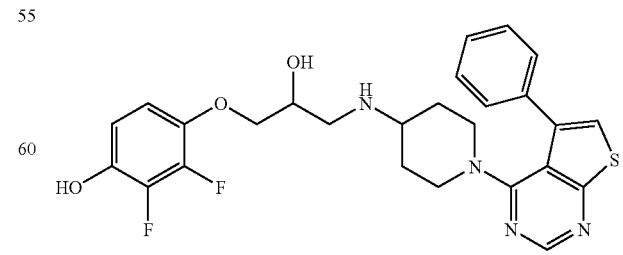

Synthesis followed SP6 (3 h), using 430 µmol 2-((2,3-difluoro-4-methoxyphenoxy)methyl)oxirane and 1-(5-phenylthieno[2,3-d]pyrimidin-4-yl)piperidin-4-amine to give O-methylated intermediate 1-(2,3-difluoro-4-methoxyphenoxy)-3-(1-(5-phenylthieno[2,3-d]pyrimidin-4-yl)piperidin-4-ylamino)propan-2-ol upon purification by prep. TLC (1 mm silica gel, PE/CH₂Cl₂/MeOH 4:6:1) with 49% yield. Product was obtained by O-demethylation according to SP12 (3 h) with 58% yield (LCMS: detected [M+1]=513.2).

Example 46

4-(2-hydroxy-3-(1-(5-phenylthieno[2,3-d]pyrimidin-4-yl)piperidin-4-ylamino)propoxy)benzene-1,2-diol

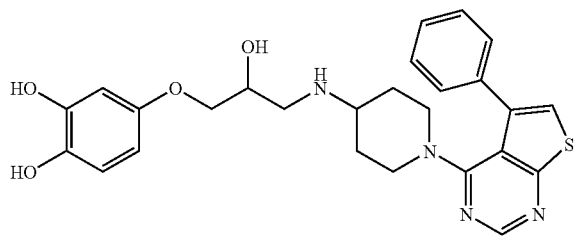

Synthesis followed SP6 (3 h), using 430 μmol 2-((3,4-dimethoxyphenoxy)methyl)oxirane and 1-(5-phenylthieno[2,3-d]pyrimidin-4-yl)piperidin-4-amine to give O-methylated intermediate 1-(3,4-dimethoxyphenoxy)-3-(1-(5-phenylthieno[2,3-d]pyrimidin-4-ylpiperidin-4-ylamino) propan-2-ol upon purification by prep. TLC (1 mm silica gel, PE/CH₂Cl₂/MeOH 4:6:1) with 31% yield. Product was obtained by double O-demethylation according to SP12 (4 h) with 23% yield (LCMS: detected [M+1]=493.2).

Example 47

3-fluoro-4-(2-hydroxy-3-(1-(5-phenylthieno[2,3-d]pyrimidin-4-yl)piperidin-4-ylamino)propoxy)phenol

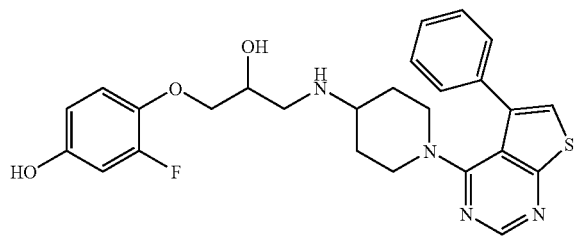

Synthesis followed SP6 (3 h), using 300 μmol 2-((2-fluoro-4-methoxyphenoxy)methyl)oxirane and 1-(5-phenylthieno[2,3-d]pyrimidin-4-yl)piperidin-4-amine to give O-methylated intermediate 1-(2-fluoro-4-methoxyphenoxy)-3-(1-(5-phenylthieno[2,3-d]pyrimidin-4-yl)piperidin-4-ylamino) propan-2-ol upon purification by prep. TLC (1 mm silica gel, PE/CH₂Cl₂/MeOH 4:6:1) with 40% yield. Product was obtained by O-demethylation according to SP12 (1 h) with 37% yield (LCMS: detected [M+1]=495.2).

Example 48

3-(3-(1-(4,6-dimethylpyrimidin-2-yl)piperidin-4-ylamino)-2-hydroxypropoxy)phenol

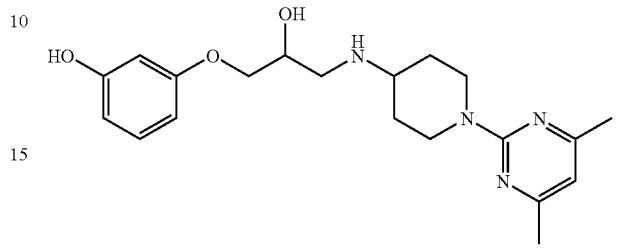

Synthesis followed SP6 (iPrOH:DMSO 1:1, 120° C., 24 h), using 200 μmol 3-(oxiran-2-ylmethoxy)phenyl benzoate and 1-(4,6-dimethylpyrimidin-2-yl)piperidin-4-amine to give O-benzoylated intermediate, which was directly treated according to SP10. Title product was obtained by purification by prep. HPLC (reversed phase) and prep. TLC (1 mm silica gel, PE/CH₂Cl₂/MeOH 4:6:1) with 14% yield (LCMS: detected [M+1]=373.2).

Example 49

1-(1-(4,6-dimethylpyrimidin-2-yl)piperidin-4-ylamino)-3-(3-(hydroxymethyl)phenoxy)propan-2-ol

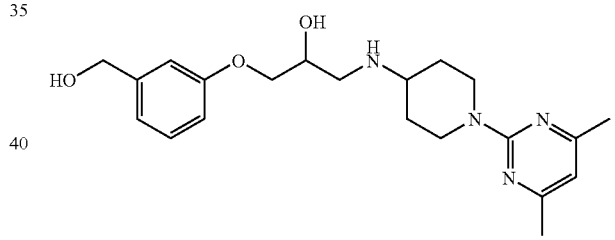

Synthesis followed SP6 (iPrOH:DMSO 1:1, 120° C., 24 h), using 200 μmol (3-(oxiran-2-ylmethoxy)phenyl)methanol and 1-(4,6-dimethylpyrimidin-2-yl)piperidin-4-amine to give the title compound with 9% yield upon purification by prep. HPLC (reversed phase) and subsequent by prep. TLC (1 mm silica gel, PE/CH₂Cl₂/MeOH 4:6:1) (LCMS: detected [M+1]=387.2).

Activity and Selectivity of Compounds according to the Present Invention

Agonistic Activity at β3-Adrenoceptor:

++++ $EC_{50}$=0.01-0.99 nM
+++ $EC_{50}$ 1-10 nM
++ $EC_{50}$ 11-100 nM
+ $EC_{50}$>100 nM

Selectivity Criteria:
for a definition of the criteria, see above
+++ A×B>1000
++ A×B=101-1000
+ A×B=10-100
0 A×B<10

TABLE I

| Example | [M + 1] found (LCMS) | activity [EC$_{50}$(β3)] | selectivity [A x B] |
|---|---|---|---|
| 1 | 477.2 | +++ | ++ |
| 2 | 477.2 | ++ | 0 |
| 3 | 477.2 | ++++ | ++ |
| 4 | 415.2 | ++ | ++ |
| 5 | 415.2 | ++ | ++ |
| 6 | 491.2 | +++ | + |
| 7 | 401.2 | ++ | ++ |
| 8 | 373.2 | ++ | 0 |
| 9 | 483.1 | +++ | + |
| 10 | 495.2 | +++ | ++ |
| 11 | 509.2 | + | 0 |
| 12 | 549.2 | + | 0 |
| 13 | 507.2 | ++++ | +++ |
| 14 | 509.2 | ++++ | +++ |
| 15 | 521.2 | ++++ | +++ |
| 16 | 521.2 | + | ++ |
| 17 | 487.2 | + | 0 |
| 18 | 445.2 | +++ | ++ |
| 19 | 445.2 | +++ | +++ |
| 20 | 563.2 | + | 0 |
| 21 | 521.2 | +++ | ++ |
| 22 | 473.2 | + | 0 |
| 23 | 431.2 | +++ | ++ |
| 24 | 403.2 | +++ | +++ |
| 25 | 555.2 | + | 0 |
| 26 | 513.2 | ++++ | ++ |
| 27 | 477.2 | ++++ | + |
| 28 | 535.2 | + | 0 |
| 29 | 507.2 | ++ | ++ |
| 30 | 505.2 | +++ | + |
| 31 | 505.2 | ++++ | +++ |
| 32 | 549.2 | +++ | + |
| 33 | 507.2 | +++ | ++ |
| 34 | 535.2 | + | 0 |
| 35 | 521.2 | + | + |
| 36 | 491.2 | ++ | ++ |
| 37 | 429.2 | ++ | 0 |
| 38 | 429.2 | + | 0 |
| 39 | 505.2 | + | 0 |
| 40 | 509.2 | ++ | + |
| 41 | 505.2 | + | + |
| 42 | 519.2 | + | 0 |
| 43 | 491.2 | +++ | ++ |
| 44 | 509.2 | + | + |

Some compounds displayed selectivities (A×B) even with a five digit selectivity factor; according to review M. Sawa et al., Curr. Med. Chem. 2006, 13, 25, one aryloxypropanolamine from Wyeth displayed a most promising selectivity profile for β3 over β1- and β2-adrenoceptors, which, however, could not be reproduced in our assay systems. Especially over β2, no selectivity was detectable.

The invention claimed is:
1. A compound of formula II formula II

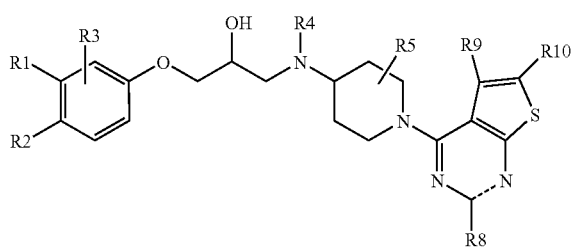

wherein
the dotted bond represents a single or a double bond;
R1 and R2 are selected from the group consisting of hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, provided that if R1 is different from hydroxyl or hydroxymethyl, then R2 must represent hydroxyl or hydroxymethyl;

R3 is selected from the group consisting of hydrogen, halogen, hydroxyl, carboxy, carbamoyl, sulfamoyl, cyano, nitro, NR6R7, alkyl, alkoxy, alkylcarbonyl, and alkoxycarbonyl;

R4 is hydrogen, alkylcarbonyl, or alkyl;

R5 is selected from the group consisting of hydrogen, and alkyl, wherein alkyl is unsubstituted or substituted with one or more residues, which are optionally selected from the group consisting of hydroxyl, alkoxy, fluoro, and NR6R7;

R6 and R7 are independently selected from the group consisting of hydrogen, alkyl, aryl, alkylsulfonyl, arylsulfonyl, heteroarylsulfonyl, alkylcarbonyl, alkoxycarbonyl, aminocarbonyl, alkylaminocarbonyl, arylcarbonyl, and heteroarylcarbonyl; wherein each alkyl is unsubstituted or substituted with one or more residues, which are optionally selected from the group consisting of hydroxyl, alkoxy, phenyl, fluoro, carboxy, and NR16R17; and wherein R6 and R7 optionally form a 5-7 membered cycle; and wherein each aryl or heteroaryl is a monocyclic aromatic or heteroaromatic ring, respectively, which can be unsubstituted or substituted with one or more residues, which are optionally selected from the group consisting of hydroxyl, alkoxy, halogen, alkyl, carboxy, NR16R17, cyano and nitro;

R8 is selected from the group consisting of hydrogen, alkyl, hydroxyl, and alkoxy;

R9 and R10 are independently selected from the group consisting of hydrogen, carboxy, NR6R7, alkyl and a mono- or bicyclic aromatic or heteroaromatic ring; and R16 and R17 are independently selected from the group consisting of hydrogen, C1-C8 alkyl, phenyl, thienyl, pyridyl, C1-C8 alkylsulfonyl, phenylsulfonyl, thienylsulfonyl, pyridylsulfonyl, C1-C8 alkylcarbonyl, C1-C8 alkoxycarbonyl, aminocarbonyl, C1-C8 alkylaminocarbonyl, thienylcarbonyl, pyridylcarbonyl, and phenylcarbonyl, and wherein R16 and R17 optionally form a 5-7 membered cycle;

or a pharmaceutically acceptable salt thereof.

2. A compound according to claim 1, wherein
the dotted bond represents a single or a double bond;
R1 and R2 are selected from the group consisting of hydrogen, halogen, hydroxyl, carboxy, carbamoyl, cyano, nitro, sulfamoyl, NR6R7, C1-C3 alkyl, C1-C3 alkoxy, C1-C3 alkylcarbonyl, C1-C3 alkoxycarbonyl, C1-C4 alkylaminocarbonyl, morpholinocarbonyl, and 2-thienylsulfonylaminomethyl, wherein each alkyl is unsubstituted or substituted with one or more residues optionally selected from the group consisting of hydroxyl, C1-C3 alkoxy, fluoro, and NR6R7; and wherein the thienyl is unsubstituted or substituted with one or more residues optionally selected from the group consisting of hydroxyl, C1-C3 alkoxy, halogen, C1-C3 alkyl, carboxy, NR6R7 and cyano, provided that if R1 is different from hydroxyl or hydroxymethyl, then R2 must represent hydroxyl or hydroxymethyl;

R3 is selected from the group consisting of hydrogen, halogen, hydroxyl, carboxy, carbamoyl, sulfamoyl, cyano, nitro, NR6R7, C1-C3 alkyl, C1-C3 alkoxy, C1-C3 alkylcarbonyl, and C1-C3 alkoxycarbonyl, wherein each alkyl is unsubstituted or substituted with one or more residues optionally selected from the group consisting of hydroxyl, C1-C3 alkoxy, fluoro, and NR6R7;

R4 is hydrogen or methyl;

R5 is selected from the group consisting of hydrogen and methyl, wherein methyl is unsubstituted or substituted with one or more residues selected from the group consisting of hydroxyl, methoxy, ethoxy, fluoro, and NR6R7;

R6 and R7 are independently selected from the group consisting of hydrogen, C1-C3 alkyl, C1-C8 alkylsulfonyl, 2-thienylsulfonyl, C1-C8 alkylcarbonyl, C1-C4 alkoxycarbonyl, aminocarbonyl, and C1-C8 alkylaminocarbonyl; wherein each alkyl is unsubstituted or substituted with one or more residues optionally selected from the group consisting of hydroxyl, C1-C3 alkoxy, carboxy, and NR16R17; and wherein R6 and R7 optionally form a 5-7 membered cycle; and wherein the thienyl is unsubstituted or substituted with one or more residues selected from the group consisting of hydroxyl, C1-C3 alkoxy, halogen, C1-C3 alkyl, carboxy, NR16R17 and cyano;

R8 is selected from the group consisting of hydrogen and methyl;

R9 and R10 are independently selected from the group consisting of hydrogen, NR6R7, C1-C6 alkyl, phenyl, thienyl, furanyl, and pyridinyl, wherein each alkyl is unsubstituted or substituted with one or more residues optionally selected from the group consisting of hydroxyl, C1-C3 alkoxy, fluoro, NR6R7, and carboxy; and wherein each monocyclic aromatic or heteroaromatic ring is unsubstituted or substituted with one or more residues optionally selected from the group consisting of C1-C3 alkyl, hydroxyl, C1-C4 alkoxy, C1-C4 alkoxycarbonyl, C1-C4 alkylaminocarbonyl, carboxy (C1-C2)alkoxy, C1-C3 alkoxycarbonyl(C1-C2)alkoxy, 2-alkoxy-2-oxoethoxy, halogen, carboxy, NR6R7 and cyano; wherein two of these residues optionally form a 5-7 membered non-aromatic ring;

R16 and R17 are independently selected from the group consisting of hydrogen, C1-C3 alkyl, C1-C4 alkylsulfonyl, 2-thienylsulfonyl, C1-C4 alkylcarbonyl, C1-C4 alkoxycarbonyl, aminocarbonyl, and C1-C4 alkylaminocarbonyl, wherein R16 and R17 optionally form a 5-7 membered cycle.

3. A compound according to claim 1, wherein the dotted bond represents a single or a double bond;

R1 is selected from the group consisting of hydrogen, halogen, hydroxyl, hydroxymethyl, methoxycarbonyl, ethoxycarbonyl, methyl, ethyl, carboxy, and methoxymethyl;

R2 is selected from the group consisting of hydrogen, hydroxyl, methoxycarbonyl, carboxy, and hydroxymethyl;

R3 is selected from the group consisting of hydrogen, halogen, methyl, ethyl, methoxycarbonyl, ethoxycarbonyl, carboxy, and hydroxymethyl;

R4 is hydrogen or methyl;

R5 is hydrogen or methyl;

R8 is hydrogen or methyl;

R9 is hydrogen, methyl, unsubstituted phenyl, halophenyl, para-fluorophenyl, or thienyl; and R10 is hydrogen, methyl, unsubstituted phenyl, or halophenyl.

4. A compound of formula III

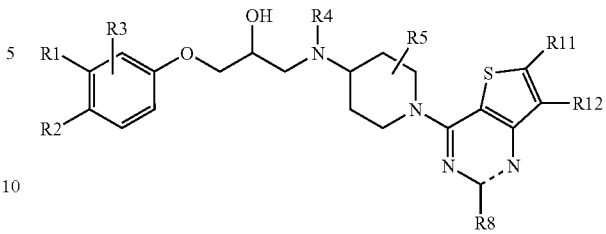

formula III wherein the dotted bond represents a single or a double bond;

R1 and R2 are selected from the group consisting of hydrogen, halogen, hydroxyl, carboxy, carbamoyl, sulfamoyl, cyano, nitro, NR6R7, alkyl, alkoxy, alkylcarbonyl, alkoxycarbonyl, alkylcarbonylamino, alkylaminocarbonyl, arylsulfonylaminomethyl, heteroarylsulfonylaminomethyl and alkylaminosulfonyl, provided that if R1 is different from hydroxyl or hydroxymethyl, then R2 must represent hydroxyl or hydroxymethyl;

R3 is selected from the group consisting of hydrogen, halogen, hydroxyl, carboxy, carbamoyl, sulfamoyl, cyano, nitro, NR6R7, alkyl, alkoxy, alkylcarbonyl, and alkoxycarbonyl;

R4 is hydrogen, alkylcarbonyl, or alkyl;

R5 is selected from the group consisting of hydrogen, and alkyl, wherein alkyl is unsubstituted or substituted with one or more residues, which are optionally selected from the group consisting of hydroxyl, alkoxy, fluoro, and NR6R7;

R6 and R7 are independently selected from the group consisting of hydrogen, alkyl, aryl, alkylsulfonyl, arylsulfonyl, heteroarylsulfonyl, alkylcarbonyl, alkoxycarbonyl, aminocarbonyl, alkylaminocarbonyl, arylcarbonyl, and heteroarylcarbonyl; wherein each alkyl is unsubstituted or substituted with one or more residues, which are optionally selected from the group consisting of hydroxyl, alkoxy, phenyl, fluoro, carboxy, and NR16R17; and wherein R6 and R7 optionally form a 5-7 membered cycle; and herein each aryl or heteroaryl is a monocyclic aromatic or heteroaromatic ring, which is optionally unsubstituted or substituted with one or more residues, which are optionally selected from the group consisting of hydroxyl, alkoxy, halogen, alkyl, carboxy, NR16R17, cyano and nitro;

R8 is selected from the group consisting of hydrogen, alkyl, hydroxyl, and alkoxy;

R11 and R12 are independently selected from the group consisting of hydrogen, carboxy, NR6R7, alkyl and a mono- or bicyclic aromatic or heteroaromatic ring, R16 and R17 are independently selected from the group consisting of hydrogen, C1-C8 alkyl, phenyl, thienyl, pyridyl, C1-C8 alkylsulfonyl, phenylsulfonyl, thienylsulfonyl, pyridylsulfonyl, C1-C8 alkylcarbonyl, C1-C8 alkoxycarbonyl, aminocarbonyl, C1-C8 alkylaminocarbonyl, thienylcarbonyl, pyridylcarbonyl, and phenylcarbonyl, and wherein R16 and R17 optionally form a 5-7 membered cycle or a pharmaceutically acceptable salt thereof.

5. A compound according to claim 4, wherein the dotted bond represents a single or a double bond;

R1 and R2 are selected from the group consisting of hydrogen, halogen, hydroxyl, carboxy, carbamoyl, cyano, nitro, sulfamoyl, NR6R7, C1-C3 alkyl, C1-C3 alkoxy, C1-C3 alkylcarbonyl, C1-C3 alkoxycarbonyl, C1-C4 alkylaminocarbonyl, morpholinocarbonyl, and 2-thienylsulfonylaminomethyl, wherein each alkyl is unsubstituted or substituted with one or more residues optionally selected from the group consisting of hydroxyl, C1-C3 alkoxy, fluoro, and NR6R7; and wherein the thienyl is unsubstituted or substituted with one or more residues optionally selected from the group consisting of hydroxyl, C1-C3 alkoxy, halogen, C1-C3 alkyl, carboxy, NR6R7 and cyano, provided that if R1 is different from hydroxyl or hydroxymethyl, then R2 must represent hydroxyl or hydroxymethyl;

R3 is selected from the group consisting of hydrogen, halogen, hydroxyl, carboxy, carbamoyl, sulfamoyl, cyano, nitro, NR6R7, C1-C3 alkyl, C1-C3 alkoxy, C1-C3 alkylcarbonyl, and C1-C3 alkoxycarbonyl, wherein each alkyl is unsubstituted or substituted with one or more residues optionally selected from the group consisting of hydroxyl, C1-C3 alkoxy, fluoro, and NR6R7;

R4 is hydrogen or methyl;

R5 is selected from the group consisting of hydrogen and methyl, wherein methyl is unsubstituted or substituted with one or more residues selected from the group consisting of hydroxyl, methoxy, ethoxy, fluoro, and NR6R7;

R6 and R7 are independently selected from the group consisting of hydrogen, C1-C3 alkyl, C1-C8 alkylsulfonyl, 2-thienylsulfonyl, C1-C8 alkylcarbonyl, C1-C4 alkoxycarbonyl, aminocarbonyl, and C1-C8 alkylaminocarbonyl; wherein each alkyl is unsubstituted or substituted with one or more residues optionally selected from the group consisting of hydroxyl, C1-C3 alkoxy, carboxy, and NR16R17; and wherein R6 and R7 optionally form a 5-7 membered cycle; and wherein the thienyl is unsubstituted or substituted with one or more residues selected from the group consisting of hydroxyl, C1-C3 alkoxy, halogen, C1-C3 alkyl, carboxy, NR16R17 and cyano;

R8 is selected from the group consisting of hydrogen and methyl;

R11 and R12 are independently selected from the group consisting of hydrogen, NR6R7, C1-C6 alkyl, phenyl, thienyl, furanyl, and pyridinyl, wherein each alkyl is unsubstituted or substituted with one or more residues optionally selected from the group consisting of hydroxyl, C1-C3 alkoxy, fluoro, NR6R7, and carboxy; and wherein each monocyclic aromatic or heteroaromatic ring is unsubstituted or substituted with one or more residues optionally selected from the group consisting of C1-C3 alkyl, hydroxyl, C1-C4 alkoxy, C1-C4 alkoxycarbonyl, C1-C4 alkylaminocarbonyl, carboxy (C1-C2)alkoxy, C1-C3 alkoxycarbonyl(C1-C2)alkoxy, 2-alkoxy-2-oxoethoxy, halogen, carboxy, NR6R7 and cyano; wherein two of these residues optionally form a 5-7 membered non-aromatic ring;

R16 and R17 are independently selected from the group consisting of hydrogen, C1-C3 alkyl, C1-C4 alkylsulfonyl, 2-thienylsulfonyl, C1-C4 alkylcarbonyl, C1-C4 787alkoxycarbonyl, aminocarbonyl, and C1-C4 alkylaminocarbonyl, wherein R16 and R17 optionally form a 5-7 membered cycle.

6. A compound according to claim 4, wherein
the dotted bond represents a single or a double bond;
R1 is selected from the group consisting of hydrogen, halogen, hydroxyl, hydroxymethyl, methoxycarbonyl, ethoxycarbonyl, methyl, ethyl, carboxy, and methoxymethyl;

R2 is selected from the group consisting of hydrogen, hydroxyl, methoxycarbonyl, carboxy, and hydroxymethyl;

R3 is selected from the group consisting of hydrogen, halogen, methyl, ethyl, methoxycarbonyl, ethoxycarbonyl, carboxy, and hydroxymethyl;

R4 is hydrogen or methyl;

R5 is hydrogen or methyl;

R8 is hydrogen or methyl;

R11 is hydrogen, methyl, unsubstituted phenyl, halophenyl, para-fluorophenyl, or thienyl; and R12 is hydrogen, methyl, unsubstituted phenyl, or halophenyl.

7. A compound according to claim 1, wherein R1 is hydroxyl or hydroxymethyl, and R2 is hydroxyl or hydrogen.

8. A compound according to claim 1, wherein R1 is hydrogen, hydroxyl or hydroxymethyl, R2 is hydroxyl, and R4 and R5 are both hydrogen.

9. A compound, which is 4-(2-hydroxy-3-(1-(5-phenylthieno[2,3-d]pyrimidin-4-yl)piperidin-4-ylamino)propoxy)phenol (R)-4-(2-hydroxy-3-(1-(5-phenylthieno[2,3-d]pyrimidin-4-yl)piperidin-4-ylamino)propoxy)phenol (S)-4-(2-hydroxy-3-(1-(5-phenylthieno[2,3-d]pyrimidin-4-yl)piperidin-4-ylamino)propoxy)phenol 4-(2-hydroxy-3-(1-(5-methylthieno[2,3-d]pyrimidin-4-yl)piperidin-4-ylamino)propoxy)phenol 4-(2-hydroxy-3-(1-(2-methylthieno[2,3-d]pyrimidin-4-yl)piperidin-4-ylamino)propoxy)phenol 4-(2-hydroxy-3-(1-(5-methyl-6-phenylthieno[2,3-d]pyrimidin-4-yl)piperidin-4-ylamino)propoxy)phenol 4-(2-hydroxy-3-(1-(5-(thiophen-2-yl)thieno[2,3-d]pyrimidin-4-yl)piperidin-4-ylamino)propoxy)phenol 4-(3-(1-(5-(4-fluorophenyl)thieno[2,3-d]pyrimidin-4-yl)piperidin-4-ylamino)-2-hydroxypropoxy)phenol 4-(3-((1-(5-(4-fluorophenyl)thieno[2,3-d]pyrimidin-4-yl)piperidin-4-yl)(methyl)amino)-2-hydroxypropoxy)phenol Ethyl 2-hydroxy-5-(2-hydroxy-3-(1-(5-phenylthieno[2,3-d]pyrimidin-4-yl)piperidin-4-ylamino)propoxy)benzoate 4-(2-hydroxy-3-(1-(5-phenylthieno[2,3-d]pyrimidin-4-yl)piperidin-4-ylamino)propoxy)-2-(hydroxymethyl)phenol 2-hydroxy-5-(2-hydroxy-3-(1-(5-phenylthieno[2,3-d]pyrimidin-4-yl)piperidin-4-ylamino)propoxy)benzoic acid Ethyl 2-hydroxy-5-(2-hydroxy-3-(1-(5-methylthieno[2,3-d]pyrimidin-4-yl)piperidin-4-ylamino)propoxy)benzoate 4-(2-hydroxy-3-(1-(5-methylthieno[2,3-d]pyrimidin-4-yl)piperidin-4-ylamino)propoxy)-2-(hydroxymethyl)phenol 4-(2-hydroxy-3-(1-(2-methylthieno[2,3-d]pyrimidin-4-yl)piperidin-4-ylamino)propoxy)-2-(hydroxymethyl)phenol Ethyl 2-hydroxy-5-(2-hydroxy-3-(1-(5-methyl-6-phenylthieno[2,3-d]pyrimidin-4-yl)piperidin-4-ylamino)propoxy)benzoate 4-(2-hydroxy-3-(1-(5-methyl-6-phenylthieno[2,3-d]pyrimidin-4-yl)piperidin-4-ylamino)propoxy)-2-(hydroxymethyl)phenol Ethyl 2-hydroxy-5-(2-hydroxy-3-(1-(5-(thiophen-2-yl)thieno[2,3-d]pyrimidin-4-yl)piperidin-4-ylamino)propoxy)benzoate 4-(2-hydroxy-3-(1-(5-(thiophen-2-yl)thieno[2,3-d]pyrimidin-4-yl)piperidin-4-ylamino)propoxy)-2-(hydroxymethyl)phenol
3-(2-Hydroxy-3-(1-(5-phenyl-thieno[2,3-d]pyrimidin-4-yl)-piperidin-4-ylamino)-propoxy)-phenol
Methyl 2-hydroxy-4-(2-hydroxy-3-(1-(5-phenylthieno[2,3-d]pyrimidin-4-yl)piperidin-4-ylamino)propoxy)benzoate
5-(2-hydroxy-3-(1-(5-phenylthieno[2,3-d]pyrimidin-4-yl)piperidin-4-ylamino)propoxy)-2-(hydroxymethyl)phenol
3-Ethyl-4-(2-hydroxy-3-(1-(5-phenylthieno[2,3-d]pyrimidin-4-yl)piperidin-4-ylamino)propoxy)phenol
2-Ethyl-4-(2-hydroxy-3-(1-(5-phenylthieno[2,3-d]pyrimidin-4-yl)piperidin-4-ylamino)propoxy)phenol
Ethyl 5-hydroxy-2-(2-hydroxy-3-(1-(5-phenylthieno[2,3-d]pyrimidin-4-yl)piperidin-4-ylamino)propoxy)benzoate
4-(2-hydroxy-3-(1-(5-phenylthieno[2,3-d]pyrimidin-4-yl)piperidin-4-ylamino)propoxy)-3-(hydroxymethyl)phenol
4-(2-hydroxy-3-(1-(thieno[3,2-d]pyrimidin-4-yl)piperidin-4-ylamino)propoxy)phenol
Ethyl 2-hydroxy-5-(2-hydroxy-3-(1-(thieno[3,2-d]pyrimidin-4-yl)piperidin-4-ylamino)propoxy)benzoate
4-(2-hydroxy-3-(1-(thieno[3,2-d]pyrimidin-4-yl)piperidin-4-ylamino)propoxy)-2-(hydroxymethyl)phenol
1-(4-(hydroxymethyl)phenoxy)-3-(1-(5-phenylthieno[2,3-d]pyrimidin-4-yl)piperidin-4-ylamino)propan-2-ol
1-(3-(hydroxymethyl)phenoxy)-3-(methyl(1-(5-methyl-6-phenylthieno[2,3-d]pyrimidin-4-yl)piperidin-4-yl)amino)propan-2-ol
1-(3-(hydroxymethyl)phenoxy)-3-(methyl(1-(5-phenylthieno[2,3-d]pyrimidin-4-yl)piperidin-4-yl)amino)propan-2-ol
1-(1-(5-(4-fluorophenyl)thieno[2,3-d]pyrimidin-4-yl)piperidin-4-ylamino)-3-(3-(hydroxymethyl)phenoxy)propan-2-ol
1-(3-(hydroxymethyl)phenoxy)-3-(1-(5-methyl-6-phenylthieno[2,3-d]pyrimidin-4-yl)piperidin-4-ylamino)propan-2-ol
1-(3-(hydroxymethyl)phenoxy)-3-(1-(2-methylthieno[2,3-d]pyrimidin-4-yl)piperidin-4-ylamino)propan-2-ol
1-(3-(hydroxymethyl)phenoxy)-3-(1-(5-methylthieno[2,3-d]pyrimidin-4-yl)piperidin-4-ylamino)propan-2-ol
1-(3-(hydroxymethyl)phenoxy)-3-(1-(5-phenylthieno[2,3-d]pyrimidin-4-yl)piperidin-4-ylamino)propan-2-ol
4-hydroxy-2-(2-hydroxy-3-(1-(5-phenylthieno[2,3-d]pyrimidin-4-yl)piperidin-4-ylamino)propoxy)benzoic acid
Methyl 4-hydroxy-2-(2-hydroxy-3-(1-(5-phenylthieno[2,3-d]pyrimidin-4-yl)piperidin-4-ylamino)propoxy)benzoate
4-(2-hydroxy-3-(1-(5-phenylthieno[2,3-d]pyrimidin-4-yl)piperidin-4-ylamino)propoxy)-2-(methoxymethyl)phenol
4-(2-hydroxy-3-(1-(5-phenyl-1,2-dihydrothieno[2,3-d]pyrimidin-4-yl)piperidin-4-ylamino)propoxy)-2-(hydroxymethyl)phenol
1-(1-(5-(4-fluorophenyl)thieno[2,3-d]pyrimidin-4-yl)piperidin-4-ylamino)-3-(4-(hydroxymethyl)phenoxy)propan-2-ol
2,3-difluoro-4-(2-hydroxy-3-(1-(5-phenylthieno[2,3-d]pyrimidin-4-yl)piperidin-4-ylamino)propoxy)phenol
4-(2-hydroxy-3-(1-(5-phenylthieno[2,3-d]pyrimidin-4-yl)piperidin-4-ylamino)propoxy)benzene-1,2-diol
or
3-fluoro-4-(2-hydroxy-3-(1-(5-phenylthieno[2,3-d]pyrimidin-4-yl)piperidin-4-ylamino)propoxy)phenol
or a pharmaceutically acceptable salt thereof.

10. A pharmaceutical composition comprising a compound according to claim 1 and a pharmaceutically acceptable excipient.

11. A method for the treatment of urinary incontinence, urinary stress incontinence, urinary urge incontinence or overactive bladder, comprising administering to a subject in need thereof an effective amount of a compound of claim 1.

12. A method according to claim 11, which is for the treatment of urinary stress incontinence.

13. A method according to claim 11, which is for the treatment of overactive bladder.

14. A compound according to claim 1, which has $EC_{50}$ ($\beta 3$)$\leqq$100 nM and selectivity A×B>100.

15. A compound according to claim 1, which has $EC_{50}$ ($\beta 3$)$\leqq$10 nM and selectivity A×B>100.

16. A method for preparing a compound according to claim 1, comprising
   1) treating a phenol derivative with a methylene oxirane derivative selected from the group consisting of epibromohydrin, epichlorohydrin and glycidyl tosylate under basic conditions
   2) treating a chloro-thieno[2,3-d]pyrimidine derivative with an amine
   3) nucleophilic ring opening of the oxirane obtained in 1) with the amine obtained in 2),
wherein the order of 1) or 2) is interchangeable.

17. A compound according to claim 4, wherein R1 is hydroxyl or hydroxymethyl, and R2 is hydroxyl or hydrogen.

18. A compound according to claim 4, wherein R1 is hydrogen, hydroxyl or hydroxymethyl, R2 is hydroxyl, and R4 and R5 are both hydrogen.

19. A method according to claim 11, which is for the treatment of urinary urge incontinence.

20. A pharmaceutical composition comprising a compound according to claim 4 and a pharmaceutically acceptable excipient.

21. A method for the treatment of urinary incontinence, urinary stress incontinence, urinary urge incontinence or overactive bladder, comprising administering to a subject in need thereof an effective amount of a compound of claim 4.

22. A method according to claim 21, which is for the treatment of urinary stress incontinence.

23. A method according to claim 21, which is for the treatment of overactive bladder.

24. A method according to claim 21, which is for the treatment of urinary urge incontinence.

25. A pharmaceutical composition comprising a compound according to claim 9 and a pharmaceutically acceptable excipient.

26. A method for the treatment of urinary incontinence, urinary stress incontinence, urinary urge incontinence or overactive bladder, comprising administering to a subject in need thereof an effective amount of a compound of claim 9.

27. A method according to claim 26, which is for the treatment of urinary stress incontinence.

28. A method for preparing a compound according to claim 6, comprising
   1) treating a phenol derivative with a methylene oxirane derivative selected from the group consisting of epibromohydrin, epichlorohydrin and glycidyl tosylate under basic conditions
   2) treating a chloro-thieno[2,3-d]pyrimidine derivative or a chloro-1,2-dihydrothieno[2,3-d]pyrimidine derivative with an amine 3) nucleophilic ring opening of the oxirane obtained in 1) with the amine obtained in 2), P1 wherein the order of 1) or 2) is interchangeable.

29. A method according to claim 26, which is for the treatment of urinary urge incontinence.

30. A compound according to claim 9, which is
4-(2-hydroxy-3-(1-(thieno[3,2-d]pyrimidin-4-yl)piperidin-4-ylamino)propoxy)phenol
ethyl 2-hydroxy-5-(2-hydroxy-3-(1-(thieno[3,2-d]pyrimidin-4-yl)piperidin-4-ylamino)propoxy)benzoate or
4-(2-hydroxy-3-(1-(thieno[3,2-d]pyrimidin-4-Apiperidin-4-ylamino)propoxy)-2-(hydroxymethyl)phenol
or a pharmaceutically acceptable salt thereof.

31. A method for preparing a compound according to claim 4, comprising
1) treating a phenol derivative with a methylene oxirane derivative selected from the group consisting of epibromohydrin, epichlorohydrin and glycidyl tosylate under basic conditions
2) treating a chloro-thieno[3,2-d]pyrimidine derivative or a chloro-1,2-dihydrothieno[3,2-d]pyrimidine derivative with an amine
3) nucleophilic ring opening of the oxirane obtained in 1) with the amine obtained in 2),
wherein the order of 1) or 2) is interchangeable.

* * * * *

UNITED STATES PATENT AND TRADEMARK OFFICE
CERTIFICATE OF CORRECTION

| | | |
|---|---|---|
| PATENT NO. | : 8,207,174 B2 | Page 1 of 1 |
| APPLICATION NO. | : 12/017724 | |
| DATED | : June 26, 2012 | |
| INVENTOR(S) | : Stefan Tasler et al. | |

It is certified that error appears in the above-identified patent and that said Letters Patent is hereby corrected as shown below:

Column 69, Line 2 reads: "1) with the amine obtained in 2), P1 wherein the order" should read --1) with the amine obtained in 2), wherein the order--.

Column 69, Line 11 reads: "4-(2-hydroxy-3-(1-thieno[3,2-d]pyrimidin-4-Apiperi-" should read --4-(2-hydroxy-3-(1-thieno[3,2-d]pyrimidin-4-yl)piperi- --.

Signed and Sealed this
Second Day of October, 2012

David J. Kappos
*Director of the United States Patent and Trademark Office*